(12) United States Patent
Rangaramanujam et al.

(10) Patent No.: US 11,918,657 B2
(45) Date of Patent: Mar. 5, 2024

(54) DENDRIMER DELIVERY SYSTEM AND METHODS OF USE THEREOF

(71) Applicant: The Johns Hopkins University, Baltimore, MD (US)

(72) Inventors: Kannan Rangaramanujam, Highland, MD (US); Rishi Sharma, Baltimore, MD (US); Anjali Sharma, Baltimore, MD (US); Sujatha Kannan, Highland, MD (US); Zhi Zhang, Towson, MD (US); Siva Pramodh Kambhampati, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 16/189,932

(22) Filed: Nov. 13, 2018

(65) Prior Publication Data
US 2019/0142964 A1    May 16, 2019

Related U.S. Application Data

(60) Provisional application No. 62/584,623, filed on Nov. 10, 2017.

(51) Int. Cl.
*A61K 9/00* (2006.01)
*A61K 45/06* (2006.01)
(Continued)

(52) U.S. Cl.
CPC ........ *A61K 47/6885* (2017.08); *A61K 9/0019* (2013.01); *A61K 45/06* (2013.01);
(Continued)

(58) Field of Classification Search
CPC .................................. A61K 47/6885
See application file for complete search history.

(56) References Cited

U.S. PATENT DOCUMENTS

| | | |
|---|---|---|
| 6,624,245 B2 | 9/2003 | Wallace |
| 6,726,918 B1 | 4/2004 | Wong |

(Continued)

FOREIGN PATENT DOCUMENTS

| | | |
|---|---|---|
| CN | 103804693 | 5/2014 |
| CN | 103999853 | 8/2014 |

(Continued)

OTHER PUBLICATIONS

Aguzzi, et al., Microglia: scapegoat, saboteur, or something else? Science. Jan. 11, 2013;339(6116):156-61 (2013).

(Continued)

*Primary Examiner* — Paul W Dickinson
(74) *Attorney, Agent, or Firm* — PABST PATENT GROUP LLP

(57) ABSTRACT

Low-generation dendrimers containing a high density of surface hydroxyl groups, and methods of synthesis thereof are provided. In particular, oligo ethylene glycol (OEG)-like dendrimers with a high surface functional groups at relatively low generations (e.g. ~120 hydroxyls in the third generation, with a size of just 1-2 nm) is described. Dendrimer formulations including one or more prophylactic, therapeutic, and/or diagnostic agents, and methods of use thereof are also described. The formulations are suitable for topical, enteral, and/or parenteral delivery for treating one or more diseases, conditions, and injuries in the eye, the brain and nervous system (CNS), particularly those associated with pathological activation of microglia and astrocytes.

28 Claims, 18 Drawing Sheets

Specification includes a Sequence Listing.

(51) Int. Cl.
*A61K 47/60* (2017.01)
*A61K 47/68* (2017.01)
*C08G 83/00* (2006.01)
*A61K 47/18* (2017.01)

(52) U.S. Cl.
CPC ............ *A61K 47/60* (2017.08); *C08G 83/003* (2013.01); *C08G 83/004* (2013.01); *A61K 47/183* (2013.01)

(56) References Cited

U.S. PATENT DOCUMENTS

| | | | |
|---|---|---|---|
| 6,790,437 | B2 | 9/2004 | Malik |
| 7,674,781 | B2 | 3/2010 | Sheardown |
| 8,889,101 | B2 | 11/2014 | Kannan |
| 9,345,781 | B2 | 5/2016 | El-Sayed |
| 2003/0180250 | A1 | 9/2003 | Abhay |
| 2003/0232968 | A1 | 12/2003 | Li |
| 2004/0180852 | A1 | 9/2004 | Schengrund |
| 2005/0214286 | A1 | 9/2005 | Epstein |
| 2007/0280902 | A1 | 12/2007 | Rabinovich-Guilatt |
| 2008/0031848 | A1 | 2/2008 | Andrei |
| 2010/0015231 | A1 | 1/2010 | Lu |
| 2010/0160299 | A1 | 6/2010 | Baker |
| 2011/0018929 | A1 | 1/2011 | Kawashima |
| 2011/0034422 | A1 | 2/2011 | Kannan |
| 2012/0003155 | A1 | 1/2012 | Kannan |
| 2012/0177593 | A1 | 7/2012 | Baker, Jr. |
| 2012/0263672 | A1 | 10/2012 | Artzi |
| 2013/0123330 | A1 | 5/2013 | Lu |
| 2013/0136697 | A1 | 5/2013 | Kannan |
| 2013/0165771 | A1 | 6/2013 | Ni |
| 2015/0352230 | A1 | 12/2015 | Mullen |
| 2017/0043027 | A1 | 2/2017 | Rangaramanujam |
| 2017/0119899 | A1 | 5/2017 | Kannan |
| 2018/0256480 | A1* | 9/2018 | Deng .................. A61K 8/11 |

FOREIGN PATENT DOCUMENTS

| | | |
|---|---|---|
| CN | 103804693 | 5/2015 |
| CN | 103999853 | 8/2015 |
| JP | 2014516627 | 7/2014 |
| JP | 2017529325 | 10/2017 |
| RU | 2093165 | 10/1997 |
| RU | 2367525 | 6/2007 |
| RU | 2521338 | 8/2012 |
| WO | 0018394 | 4/2000 |
| WO | 2002067908 | 9/2002 |
| WO | 2004/058272 | 7/2004 |
| WO | 2004058272 | 7/2004 |
| WO | 2005/055926 | 11/2004 |
| WO | 2005055926 | 11/2004 |
| WO | 2005063275 | 7/2005 |
| WO | 2006/069719 | 7/2006 |
| WO | 2006069719 | 7/2006 |
| WO | 2006/115547 | 11/2006 |
| WO | 2006115547 | 11/2006 |
| WO | 2009/046446 | 4/2009 |
| WO | 2009046446 | 4/2009 |
| WO | 2009/142754 | 1/2010 |
| WO | 2009142754 | 1/2010 |
| WO | 2010/147831 | 12/2010 |
| WO | 2010/147931 | 12/2010 |
| WO | 2010147831 | 12/2010 |
| WO | 2010147931 | 12/2010 |
| WO | 2011/011384 | 7/2011 |
| WO | 2011011384 | 7/2011 |
| WO | 2011/123591 | 10/2011 |
| WO | 2011123591 | 10/2011 |
| WO | 2012/037457 | 3/2012 |
| WO | 2012037457 | 3/2012 |
| WO | 2012/142470 | 10/2012 |
| WO | 2012142470 | 10/2012 |
| WO | 2014/026283 | 2/2014 |
| WO | 2014026283 | 2/2014 |
| WO | 2014/109927 | 7/2014 |
| WO | 2014109927 | 7/2014 |
| WO | 2014/197909 | 12/2014 |
| WO | 2014197909 | 12/2014 |
| WO | 2015/027068 | 2/2015 |
| WO | 2015027068 | 2/2015 |
| WO | 2015/038493 | 3/2015 |
| WO | 2015038493 | 3/2015 |
| WO | WO-2015168347 | A1 * 11/2015 ............. A61P 27/02 |
| WO | 2014/178892 | 12/2015 |
| WO | 2014178892 | 12/2015 |
| WO | 2016/025741 | 2/2016 |
| WO | 2016025741 | 2/2016 |
| WO | 2016026981 | 2/2016 |
| WO | 2016/025745 | 4/2016 |
| WO | 2016025745 | 4/2016 |
| WO | 2017074993 | 5/2017 |
| WO | 2017/139341 | 8/2017 |
| WO | 2017139341 | 8/2017 |

OTHER PUBLICATIONS

Ahishali, et al., "Effects of lipopolysaccharide on the blood-brain barrier permeability in prolonged nitric oxide blockade-induced hypertensive rats", International Journal of Neuroscience, 115(2):151-168 (2005).

Andiman, et al., "The cerebral cortex overlying periventricular leukomalacia: analysis of pyramidal neurons", Brain Pathology, 20(4):803-814 (2010).

Anraku, et al., "Glycaemic control boosts glucosylated nanocarrier crossing the BBB into the brain", Nature Communications, 8(1):1001 (2017).

Arseneault, et al., "Recent advances in click chemistry applied to dendrimer synthesis", Molecules, 20(5):9263-9294 (2015).

Bagul, et al., "Heterolayered hybrid dendrimers with optimized sugar head groups for enhancing carbohydrate-protein interactions", Polymer Chemistry, 8(35):5354-5366 (2017).

Banks, "From blood-brain barrier to blood-brain interface: new opportunities for CNS drug delivery", Nature Reviews Drug Discovery, 15(4):275-292 (2016).

Block, et al., "Microglia-mediated neurotoxicity: uncovering the molecular mechanisms", Nat Rev Neurosci., 8(1):57-69 (2007).

Caminade, et al., "Dendrimers for drug delivery", Journal of Materials Chemistry B, 26:4055 (2014).

Carlesi, et al., "Strategies for clinical approach to neurodegeneration in Amyotrophic lateral sclerosis", Archives Italiennes de Biologie, 149:151-167 (2011).

Chauhan, et al., "Unexpected in vivo anti-inflammatory activity observed for simple, surface functionalized poly(amidoamine) dendrimers", Biomacromolecules, 10(5):1195-1202 (2009).

Corraliza, "Recruiting specialized macrophages across the borders to restore brain functions", Frontiers in Cellular Neuroscience, 8:262 (2014).

Cunningham, et al., "Identification of a survival-promoting peptide in medium conditioned by oxidatively stressed cell lines of nervous system origin", J Neurosci., 18(18):7047-7060 (1998).

Dai, "Intrinsic targeting of inflammatory cells in the brain by polyamidoamine dendrimers upon subarachnoid administration", Nanomedicine, 5(9):1317-1329(2010).

Dammann, "Persistent neuro-inflammation in cerebral palsy: a therapeutic window of opportunity?", Acta Paediatrica, 96(1):6-7 (2007).

Dommergues, et al., "Early microglial activation following neonatal excitotoxic brain damage in mice: a potential target for neuroprotection", Neuroscience, 121(3):619-628 (2003).

Esfand, et al., "Poly(amidoamine) (PAMAM) dendrimers: from biomimicry to drug delivery and biomedical applications", Drug Discovery Today, 6(8):427-436 (2001).

Faustino, et al., "Microglial cells contribute to endogenous brain defenses after acute neonatal focal stroke", J Neurosci., 31(36):12992-13001 (2011).

Giulian, et al., "Brain glia release factors with opposing actions upon neuronal survival", J Neurosci., 13(1):29-37 (1993).

(56) References Cited

OTHER PUBLICATIONS

Gordon, "Amyotrophic Lateral Sclerosis: An update for 2013 Clinical Features, Pathophysiology, Management and Therapeutic Trials", Aging and Disease, 4(5):295-310 (2013).
Guo, et al., "Dendrimers Target the Ischemic Lesion in Rodent and Primate Models of Nonarteritic Anterior Ischemic Optic Neuropathy", PLOS ONE, 11(4):e0154437 (2016).
Hagberg, et al., "Inflammation during fetal and neonatal life: implications for neurologic and neuropsychiatric disease in children and adults", Annals of Neurology, 71(4):444-457 (2012).
Han, et al., "Convergent Synthesis of PAMAM Dendrimers Containing Tetra(ethyleneoxide) at Core Using Click Chemistry", Bull. Korean Chem. Soc. 33(10):3501-3504 (2012).
Hardy, et al., "Genetic classification of primary neurodegenerative disease", Science, 282(5391):1075-1079 (1998).
Hayder, et al., "A phosphorus-based dendrimer targets inflammation and osteoclastogenesis in experimental arthritis", Science Translational Medicine, 3(81):81ra35 (2011).
Haynes, et al., "Nitrosative and oxidative injury to premyelinating oligodendrocytes in periventricular leukomalacia", Journal of Neuropathology & Experimental Neurology, 62(5):441-450 (2003).
Heneka, et al., "Innate immune activation in neurodegenerative disease", Nature Reviews, 14(7):463-477 (2014).
Hervas-Stubbs, et al., "CD8 T cell priming in the presence of IFN-$\alpha$ renders CTLs with improved responsiveness to homeostatic cytokines and recall antigens: important traits for adoptive T cell therapy", J. Immunol., 189(7):3299-3310 (2012).
Hoyle, et al., "Thiol-ene click chemistry", Angewandte Chemie International Edition, 49(9):1540 (2010).
Iezzi, et al., "Dendrimer-based targeted intravitreal therapy for sustained attenuation of neuroinflammation in retinal degeneration", Biomaterials, 33(3):979-988 (2012).
Inapagolla, et al., "In vivo efficacy of dendrimer-methylprednisolone conjugate formulation for the treatment of lung inflammation", International Journal of Pharmaceutics, 399(1-2):140-147 (2010).
International Search Report for corresponding PCT application PCT/US018/060795 dated Mar. 1, 2019.
Jacobs, et al., "Current review of in vivo GBM rodent models: emphasis on the CNS-1 tumour model", ASN Neuro 2011, 3(3):e00063 (2011).
Kambhampati, et al., "Intracellular delivery of dendrimer triamcinolone acetonide conjugates into microglial and human retinal pigment epithelial cells", European Journal of Pharmaceutics and Biopharmaceutics, 95(B):239-249 (2015a).
Kambhampati, et al., "Systemic and Intravitreal Delivery of Dendrimers to Activated Microglia/Macrophage in Ischemia/Reperfusion Mouse Retina", Invest Ophthalmol Vis Sci., 56(8):4413-4424 (2015b).
Kannan, et al., "Decreased Cortical Serotonin in Neonatal Rabbits Exposed to Endotoxin in Utero", Journal of Cerebral Blood Flow and Metabolism: Official Journal Of The International Society Of Cerebral Blood Flow And Metabolism, 31:738-749 (2011a).
Kannan, et al., "Dendrimer-based postnatal therapy for neuroinflammation and cerebral palsy in a rabbit model", Sci Transl Med., 4(130):130ra46 (2012).
Kannan, et al., "Emerging concepts in dendrimer-based nanomedicine: from design principles to clinical applications", Journal of Internal Medicine, 276:579-617 (2014).
Kannan, et al., "Magnitude of [(11)C]PK11195 binding is related to severity of motor deficits in a rabbit model of cerebral palsy induced by intrauterine endotoxin exposure.", Developmental Neuroscience, 33(3-4):231-240 (2011b).
Kannan, et al., "Systemic dendrimer-drug treatment of ischemia-induced neonatal white matter injury", J. Control. Release, 214:112-120 (2015).
Karlstetter, et al., "Retinal microglia: just bystander or target for therapy", Progress in Retinal and Eye Research, 45:30-57 (2015).
Kirby, et al., "Prevalence and functioning of children with cerebral palsy in four areas of the United States in 2006: a report from the Autism and Developmental Disabilities Monitoring Network", Research in Developmental Disabilities, 32(2):462-469 (2011).
Kreutzberg, "Microglia: a sensor for pathological events in the CNS", Trends in Neurosciences, 19(8):312-318 (1996).
Kwon, et al., "Neuron-Targeted Nanoparticle for siRNA Delivery to Traumatic Brain Injuries", ACS Nano 2016, 10(8):7926 (2016).
Lawson, et al., "Heterogeneity in the distribution and morphology of microglia in the normal adult mouse brain", Neuroscience, 39(1):151-70 (1990).
Ledford, et al., "Therapeutic cancer vaccine survives biotech bust", Nature, 519(7541):17-18 (2015).
Lesniak, et al., "Biodistribution of fluorescently labeled PAMAM dendrimers in neonatal rabbits: effect of neuroinflammation", Mol Pharm., 10(12):4560-4571 (2013).
Macijauskiene, et al., "Dementia with Lewy bodies: the principles of diagnostics, treatment, and management", Medicina (Kaunas), 48(1):1-8 (2012).
Mallard, et al., "Astrocytes and microglia in acute cerebral injury underlying cerebral palsy associated with preterm birth", Pediatric Research, 75(1-2):234-40 (2014).
Mignani, et al., "Bench-to-bedside translation of dendrimers: Reality or utopia? A concise analysis" Advanced Drug Delivery Reviews, 136-137:73-81 (2017).
Mishra, et al., "Dendrimer brain uptake and targeted therapy for brain injury in a large animal model of hypothermic circulatory arrest", ACS Nano, 8(3):2134-2147 (2014).
Moses, et al., "The growing applications of click chemistry", Chemical Society Reviews 2007, 36, 1249).
Nance, et al., "Nanoscale effects in dendrimer-mediated targeting of neuroinflammation", Biomaterials, 101:96-107 (2016).
Nance, et al., "Systemic dendrimer-drug treatment of ischemia-induced neonatal white matter injury", J. Control. Release, 214:112-120 (2015).
Neal, et al., "Discovery and validation of a new class of small molecule Toll-like receptor 4 (TLR4) inhibitors ", PLoS One. 2013, 8(6): e65779 (2013).
Neibert, et al., "Click dendrimers as anti-inflammatory agents: with insights into their binding from molecular modeling studies", Molecular Pharmaceutics, 10(6):2502-2508 (2013).
Nguyen, et al., "Low generation anionic dendrimers modulate islet amyloid polypeptide self-assembly and inhibit pancreatic $\beta$-cell toxicity ", RSC Adv., 80(6) 76360-76369 (2016).
O'Shea, et al., "Intraventricular hemorrhage and developmental outcomes at 24 months of age in extremely preterm infants", Journal of child neurology, 27(1):22-29 (2012).
Palucka, et al., "Cancer immunotherapy via dendritic cells", Nature Reviews Cancer, 12(4):265-277 (2012).
Paolicelli, et al., "Synaptic pruning by microglia is necessary for normal brain development", Science, 333(6048):1456-1458 (2011).
Pardo, et al., "Immunity, neuroglia and neuroinflammation in autism", International Review of Psychiatry, 17(6):485-495 (2005).
Pardridge, "Blood-brain barrier delivery", Drug Discovery Today, 12(1-2):54-61 (2007).
Perry, et al., "Microglia in neurodegenerative disease", Nat Rev Neurol. 6(4):193-201 (2010).
Pierson, et al., "Gray matter injury associated with periventricular leukomalacia in the premature infant", Acta Neuropathologica, 114(6):619-631 (2007).
Polazzi, et al., "Microglial cells protect cerebellar granule neurons from apoptosis: evidence for reciprocal signaling", Glia, 36(3):271-80 (2001).
Posadas, et al., "Neutral high-generation phosphorus dendrimers inhibit macrophage-mediated inflammatory response in vitro and in vivo", Proceedings of the National Academy of Sciences, 114(37): E7660-E7669 (2017).
Ransohoff, "How neuroinflammation contributes to neurodegeneration", Science, 353(6301):777-783 (2016).
Reid, et al., "Grey matter injury patterns in cerebral palsy: associations between structural involvement on MRI and clinical outcomes", Developmental Medicine & Child Neurology, 57(12): 1159 (2015).
Ribeiro-Viana et al., "BODIPY-Labeled DC-SIGN-Targeting Glycodendrons Efficiently Internalize and Route to Lysosomes in Human Dendritic Cells", Biomacromolecules, 13(10):3209-3219 (2012).

(56) References Cited

OTHER PUBLICATIONS

Rosenbaum, et al., "A report: the definition and classification of cerebral palsy Apr. 2006", Developmental Medicine & Child Neurology, 109:8-14 (2007).
Rostovtsev, et al., "A stepwise huisgen cycloaddition process: copper(I)-catalyzed regioselective "ligation" of azides and terminal alkynes", Angewandte Chemie International Edition, 41(14):2596-2599 (2002).
Saadani-Makki, et al., "Intrauterine administration of endotoxin leads to motor deficits in a rabbit model: a link between prenatal infection and cerebral palsy", American Journal of Obstetrics and Gynecology, 199(6):651 (2008).
Sharma, et al., "Design and synthesis of multifunctional traceable dendrimers for visualizing drug delivery", RSC Advances, 4:19242-19245 (2014b).
Sharma, et al., ""Onion peel" dendrimers: a straightforward synthetic approach towards highly diversified architectures", Polymer Chemistry, 5:4321-4366 (2014d).
Sharma, et al., "A fast track strategy toward highly functionalized dendrimers with different structural layers: an "onion peel approach"", Polym. Chem., 6:1436-1444 (2015).
Sharma, et al., "A highly versatile convergent/divergent "onion peel" synthetic strategy toward potent multivalent glycodendrimers", Chemical Communications, 87(50):13300-13303 (2014c).
Sharma, et al., "Combined A3 Coupling and Click Chemistry Approach for the Synthesis of Dendrimer-Based Biological Tools", ACS Macro Letters, 3(10):1079-1083 (2014a).
Sharma, et al., "Effect of mannose targeting of hydroxyl PAMAM dendrimers on cellular and organ biodistribution in a neonatal brain injury model", Journal of Controlled Release,283:175-189 (2018).
Sharma, et al., "Facile Construction of Multifunctional Nanocarriers Using Sequential Click Chemistry for Applications in Biology", Macromolecules, 44(3):521-529 (2011).
Sharma, et al., "Low generation polyamine dendrimers bearing flexible tetraethylene glycol as nanocarriers for plasmids and siRNA", Nanoscale, 8(9):5106-5119 (2016).
Shiao, et al., Synthesis of Dense and Chiral Dendritic Polyols Using Glyconanosynthon Scaffolds, Molecules Online, 21(4):448 (2016).
Soliman, et al., "Dendrimers and miktoarm polymers based multivalent nanocarriers for efficient and targeted drug delivery", Chem. Commun., 47:9752-9587 (2011).
Stolp, et al., "Effects of Neonatal Systemic Inflammation on Blood-Brain Barrier Permeability and Behaviour in Juvenile and Adult Rats", Cardiovascular Psychiatry and Neurology, 11(469046): 1-10 (2011).
Tabas, et al., "Anti-inflammatory therapy in chronic disease: challenges and opportunities", Science, 339(6116):166-72 (2013).
Tomalia, et al., "A New Class of Polymers: Starburst-Dendritic Macromolecules", Polymer Journal, 17(1):117-132 (1985).
Tomalia, et al., "Dendrimers as multi-purpose nanodevices for oncology drug delivery and diagnostic imaging", Biochemical Society Transactions, 35(Pt.1):61-7 (2007).
Upadhyay, et al., Drug delivery systems, CNS protection, and the blood brain barrier, Biomed Res Int., 2014:869269 (2014).
Vargas, et al., "Neuroglial activation and neuroinflammation in the brain of patients with autism", Ann Neurol., 57(1):67-81 (2005).
Wang, et al., "Adoptive transfer of tumor-primed, in vitro-activated, CD4+ T effector cells (TEs) combined with CD8+ TEs provides intratumoral TE proliferation and synergistic antitumor response", Blood, 109(11):4865-4876 (2007).
Watanabe, et al., "Protective effect of microglial conditioning medium on neuronal damage induced by glutamate", Neuroscience Letters, 289(1):53-56 (2000).
Wegener, et al., "The current development of CNS drug research", International Journal of Neuropsychopharmacology, 16(7):1687-1693 (2013).
Yang, et al., "Surface-engineered dendrimers in gene delivery", Chemical Reviews, 115(11):5274-5300 (2015).
Yang, et al., "Tumor-associated macrophages: from basic research to clinical application", Hematol Oncol, 10:58-70 (2017).
Yoon, et al., "Fetal exposure to an intra-amniotic inflammation and the development of cerebral palsy at the age of three years," American Journal of Obstetrics and Gynecology, 182(3):675-681 (2000).
Zhang, et al., "Generation-6 hydroxyl PAMAM dendrimers improve CNS penetration from intravenous administration in a large animal brain injury model", Journal of Controlled Release, 249:173-182 (2017).
Zhang, et al., "Maternal inflammation leads to impaired glutamate homeostasis and up-regulation of glutamate carboxypeptidase II in activated microglia in the fetal/newborn rabbit brain", Neurobiology of Disease, 94:116-128 (2016).
Zietlow, et al., "The effect of microglia on embryonic dopaminergic neuronal survival in vitro: diffusible signals from neurons and glia change microglia from neurotoxic to neuroprotective", The European Journal of Neuroscience, 11(5):1657-67 (1999).
Anonymous, "Poly (amidoamine)" Wikipedia, 1-11 (Mar. 27, 2018).
Berger, et al., "Current and future pharmacological treatment strategies in x-linked adrenoleukodystrophy", Brain Pathol., 20(4):845-56 (2010).
Berk, et al., "The promise of N-acetylcysteine in neuropsychiatry", Trends in Pharmacological Sciences, 34(3):167-177 (2013).
Cerqueira, et al., "Microglia response and in vivo therapeutic potential of methylprednisolone-loaded dendrimer nanoparticles in spinal cord injury", Nanoparticles, 5:738-49 (2013).
Dodd, et al., "Putative neuroprotective agents in neuropsychiatric disorders", Progress in Neuro-Psychopharmacology & Biological Psychiatry, 42:135-45 (2003).
Engelen, et al., "Bezafibrate lowers very long-chain fatty acids in X-linked adrenoleukodystrophy fibroblasts by inhibiting fatty acid elongation", J. Inherit. Metab. Dis., 35(6):1137-45 (2012).
Fang, et al., "Host—guest chemistry of dendrimer-drug complexes: 7. Formation of stable inclusions between acetylated dendrimers and drugs bearing multiple charges", J. Phys. Chem. B, 116:3075-82 (2012).
Hossain, et al., "Comparative study of microtubule inhibitors-Estramustine and natural podophyllotoxin conjugated PAMAM dendrimer on glioma cell proliferation", European Journal of Medicinal Chemistry, 68:47-57 (2013).
Islam, et al., "Controlling the cytokine storm in severe bacterial diarrhea with an oral toll-like receptor 4 antagonist", Immunology, 147:178-89 (2015).
Jaszberenyi, et al., "Physicochemical and MRI characterization of Gd3+-loaded polyamidoamine and hyperbranched dendrimers", J. Bol. Inorg. Chem., 12(3):406-420 (2007).
Jonas, et al., "Intravitreal triamcinolone acetonide for exudative age related macular degeneration", Br. J. Ophthalmol., 87(4):462-8 (2003).
Kurtoglu, et al., "Drug release characteristics of PAMAM dendrimer-drug conjugates with different linkers", Intl. J. Pharma., 384(1-2):189-94 (2010).
Lee, et al., "Synthesis of symmetrical and unsymmetrical PAMAM dendrimers by fusion between azide- and alkyne-functionalized PAMAM dendrons", Bioconjugate Chem., 18:579-84 (2007).
Leukodystropy, National Organization for Rare Disorders, pp. 1-20, https://rarediseases.org/rare-diseases/leukodystrophy/, retrieved from the internet Sep. 5, 2017.
Li, et al., "Poly (vinyl alcohol) nanoparticles prepared by freezing-thawing process for protein/peptide drug delivery", J. Controlled Release, 56:117-26 (1998).
Lintas, et al., "Genome-wide expression studies in autism spectrum disorder, Rett syndrome, and down syndrome", Neurobiol. Disease, 45:57-68 (2012).
Madaan, et al., "Dendrimers in drug delivery and targeting: Drug-dendrimer interactions and toxicity issues", J. Pharm. Bioallied. Sci., 6(3): 139-150 (2014).
Mignani, et al., "Expand classical drug administration ways by emerging routes using dendrimer drug delivery systems: a concise overview", Adv. Drug Delivery Rev., 65(10):1316-30 (2013).
Navath, et al., "Dendrimer-drug conjugates for tailored intracellular drug release based on glutathione levels", Bioconjugate Chem., 19(12):2446-53 (2008).

(56) References Cited

OTHER PUBLICATIONS

Navath, et al., "Stimuli-responsive star polyethylene glycol) drug conjugates for improved intracellular delivery of the drug in neuroinflammation", *J. Controlled Release*, 142(3):447-56 (2010).
Oelker, et el., "Ophthalmic adhesives: a materials chemistry perspective", *Journal of Materials Chemistry*, 18(22):2521 (2008).
Polam, "Effect of Chorioamnionitis on Neurodevelopmental Outcome in Preterm Infants", *Arch Pediatrics Adolesc. Med.*, 159(11):1004-1085 (2005).
Qian, et al., "Synergistic inhibition of human glioma cell line by temozolomide and PAMAM-mediated miR-21i", *Journal of Applied Polymer Science*, 127(1):570-576 (2012).
Resident, "Injection Methods", Standard Clinical Technique, 2(6): 128-129 (2009). (Japanese Language Document with English Summary).
Sadekar, et al., "Transepithelial transport and toxicity of PAMAM dendrimers for oral drug delivery", *Adv. Drug Del. Rev.*, 64:571-88 (2012).
Sarin, et al., "Effective transvascular delivery of nanoparticles across the blood-brain tumor barrier into malignant glioma cells", *J. Trans. Med.*, 80(6):1-15 (2008).
Sk, et al., "Comparative study of microtubule inhibitors—Estramustine and natural podophyllotoxin conjugated PAMAM dendrimer on glioma cell proliferation", *Eu. J. Med. Chem.*, 68:47-57 (2013b).
Teo, et al., "Preventing acute gut wall damage in infectious diarrhoeas with glycosylated dendrimers", *EMBO Mol Med.*, 4:866-81 (2012).
Tolar, et al., "N-acetyl-L-cysteine improves outcome of advanced cerebral adrenoleukodystrophy", *Bone Marrow Transplant*, 39(4):211-215 (2007).
Vandamme, et al., "Poly (amidoamine) dendrimers as ophthalmic vehicles for ocular delivery of pilocarpine nitrate and tropicamide", *J. Control. Rel.*, 102:23-28 (2005).
Yiyun, et al., "Polyamidoamine dendrimers used as solubility enhancers of ketoprofen", *Eu. J. Med. Chem.*, 40:1390-3 (2005).
Zhang, et al., "Uniform brain tumor distribution and tumor associated macrophage targeting of systemically administered dendrimers", *Biomaterials*, 52:507-16 (2015).
Sarin, et al., "Effective transvascular delivery of nanoparticles across the blood-brain tumor barrier into malignant glicoma cells", J Trans Med., 80(6):1-15 (2008).
Bi, et al., "Thiol-ene crosslinking polyamidoamine dendrimer-hyaluronic acid hyrdogel systemfor biomedical applications", Journal of Biomaterials Science, Polymer Edition, 27(8):743-57 (2016).
Cheng, et al., "The effect of dendrimers on the pharmacodynamic and pharmacokinetic behaviors of non-covalently or covalently attached drugs", European journal of Medicinal Chemistry., 43 ( 11) :2291-7 (2008).
Gondcaille, et al., "Phenylbutyrate up-regulates the adrenoleukodystrophy-related gene as a nonclassical peroxisome proliferator", J Cell Biol., 169(1):93-104 (2005).
Kemp, et al., "Gene redundancy and pharmacological gene therapy: Implications for X-linked adrenoleukodystrophy", Nature America Inc., 4(11):1261-1268 (1998).
Nanoglue(R) Technical Data Sheet, accessed Aug. 17, 2020 (Year: 2020).
Soiberman, et al., "Subconjunctival injectable dendrimer-dexamethasone gel for the treatment of corneal inflammation", Biomaterials, 40:38-53 (2017).
Alizadeh, et al., "Tumor-associated macrophages are predominant carriers of cyclodextrin-based nanoparticles into gliomas", *Nanomedicine*, 6:382-90 (2010).
Van Handel, et al., "Selective uptake of multi-walled carbon nanotubes by tumor macrophages in a murine glioma model", *Journal of Neuroimmunology*, 208(1-2):3-9 (2009).
Abcouwer, "Neural inflammation and the microglial in response to diabetic retinopathy", Journal of Ocular Biology, Diseases, and Informatics, 4:25-33 (2011).
Disabato, et al., "Neuroinflammation: The Devil is in the Details", J. Neurochem., 139(Supp2):136-153 (2016).
Fu, et al., "Experimental Methods and Transport Models for Drug Delivery across the Blood-Brain Barrier", Curr. Pharm. Biotechnol., 13(7):1346-1359 (2012).
Saettone, et al., "Evaluation of muco-adhesive properties and in vivo activity of ophthalmic vehicles based on hyaluronic acid", Int. J. Pharm., 51(3):203-212 (1989).
Dutta, et al., "Poly (propyleneimine) dendrimer based nanocontainers for targeting of efavirenz to human monocytes/macrophages in vitro", Journal of Drug Targeting, 15: 89-98 (2007).
El-Sayed, et al., "Transepithelial transport of poly(amidoamine) dendrimers across Caco-2 cell monolayers", Journal of Contr. Rel., 81(3):355-365 (2002).
Garris, Therapeutically reeducating macrophages to treat GBM, Nature Medicine, 19(10):1207-1208 (2013).
Klajnert, et al., "Interactions between PAMAM dendrimers and bovine serum albumin", Biochimica et Biophysica Acta, 1648:115-126 (2003).
Kolb, et al., "The therapeutic effects of 4-phenylbutyric acid in maintaining proteostasis", The Int. J. of Biochem. & Cell Biol., 51:45-52 (2015).
Liu, "Endoplasmic reticulum stress modulates liver inflammatory immune response in the pathogenesis of liver ischemia and reperfusion injusry", Transplantation, 94(3):211 (2012).
Majoros, et al., "PAMAM dendrimer-based multifunctional conjugate for cancer therapy: synthesis, chracterization, and functionality", Biomacromoelcules, 7(2):572-579 (2006).
Mishra, et al., "Surface-Engineered Dendrimers: a Solution for Toxicity Issues", Journal of Biomaterials Science, 20:141-166 (2009).
Trehin, et al., "Fluorescent Nanoparticle Uptake for brain Tumor Visulization", Neoplasia, 8: 302-311 (2006).
Wang, et al. "The decrease of PAMAM dendrimer-induced cytotoxicity by PEGylation via attenuation of oxidative stress", Nanotechnology, 20:105103 (2009).
Wiener, et al. "Dendrimer-based metal chelates: a new class of magnetic resonance imaging contrast agents." Magnetic resonance in medicine, 31.1: 1-8 (1994).
Xu, et al., "Dendrimer advances for the central nervous system delivery of therapeutics", ACS chem. neuro., 5(1):2-13 (2014).
Yang, et al., "In-situ-forming injectable hydrogels for regnerative medicine", Progress in Polymer Science, 39:1973-1986 (2014).
Bhutto, et al., "Transport and microglia uptake of dendrimers in normal and ischemia/reperfusion injury retina", Investigative Ophthalmology & Visual Science, 66-67 (2014).

\* cited by examiner

Formula I

DENDRIMER DELIVERY SYSTEM AND METHODS OF USE THEREOF

CROSS-REFERENCE TO RELATED APPLICATIONS

This application claims the benefit of and priority to U.S. Application No. 62/584,623 filed Nov. 10, 2017, and which is incorporated by reference in its entirety.

STATEMENT REGARDING FEDERALLY SPONSORED RESEARCH

This invention was made with government support under Grant NIBIB-1R01EB018306-01, NICHD-1R01HD-076901-01A1, and 5R01EY025304-04 awarded by the National Institutes of Health. The government has certain rights in the invention.

REFERENCE TO SEQUENCE LISTING

The Sequence Listing submitted as a text file named "JHU_C_14798_ST25.txt," created on Nov. 12, 2018, and having a size of 3,792 bytes is hereby incorporated by reference pursuant to 37 C.F.R. § 1.52(e)(5).

FIELD OF THE INVENTION

The invention generally relates to the field of molecular delivery systems, and more specifically, to dendrimers for the delivery of prophylactic, therapeutic, and/or diagnostic agents to the central nervous system of a subject to prevent, treat, and/or diagnose diseases and/or conditions.

BACKGROUND OF THE INVENTION

Central nervous system (CNS) disorders affect an estimated 1 billion people around the globe and are expected to become a more serious threat to the human population in the future. CNS diseases are often associated with an alteration or degradation of highly complex human brain and pose formidable challenges to scientists and clinicians. CNS disorders have some of the fastest growing disparities between current clinical care and patient needs among leading causes of death. This is in large part due to increased longevity, resulting in a surge in the number of patients suffering with neurological diseases and leading to increased socioeconomic and healthcare burdens worldwide (W. M. Pardridge, Drug Discovery Today, 12, 54 (2007)). From a commercial prospective, one should expect aggressive efforts from pharmaceutical organizations towards the discovery, development, and translation of neurotherapeutics, but contrary to this, many have either suspended or reduced their investments in CNS projects due to the high risk of failure in late stage clinical trials (G. Wegener, et al., International Journal of Neuropsychopharmacology, 16, 1687 (2013)). The primary clinical challenge in developing therapies for CNS diseases, such as autoimmune diseases, brain tumors, and ocular disorders, is achieving clinically relevant exposure of therapeutics to the site of injury, which is difficult to access due to CNS transport barriers. Poor transport of neuropharmaceutics through nearly impermeable CNS barriers limits the development of effective treatments for CNS disorders, from primary brain tumors to neurological, and retinal diseases. The blood brain barrier (BBB), the primary impediment to neuro-drug development, is a dynamic and highly selective physical barrier that maintains brain tissue homeostasis by regulating the intake of chemicals and restricting the entry of the toxins and blood-borne pathogens (W. A. Banks, Nature Reviews Drug Discovery, 15, 275 (2016)). Drug delivery to other parts of the CNS faces similar challenges, such as the blood-retinal barrier (BRB) for treating eye diseases, and pathology-dependent barriers, such as traditional solid tumor barrier.

Although there have been astonishing advancements in the field of neuroscience in understanding the constitution, role and functions of the brain, the therapeutic development in the areas of neurological disorders still lags behind treatment of other disease areas such as infectious diseases, cancer and cardiovascular disorders. Most of the brain related disorders are in the orphan or rare disorders categories identified by the U.S. Food and Drug Administration ("FDA"). Discovery and clinical development of CNS drugs pose huge challenges to pharmaceutical companies in terms of targeting, safety, efficacy, cost, and risk of failures, both pre-clinically and clinically, as compared to any other disease area. As a result, the past decade has witnessed discontinuation of CNS drug discovery and development projects by various large pharmaceutical companies (Wegener, G. et al., International Journal of Neuropsychopharmacology, 16, 1687 (2013)). Moreover, the poor transport of drugs through the blood brain barrier ("BBB") limits the development of effective treatments toward CNS related disorders (Upadhyay, R. K. BioMed Research International, 869269 (2014)). There is a great need to develop innovative approaches based on disease pathology to competently deliver the therapeutics across BBB to treat neurological disorders.

The majority of treatments for neurological disorders require administration at high doses, resulting in systemic side effects and toxicities. Conventional methods to circumvent CNS barriers are highly invasive, thereby causing further collateral damage and limiting the number of doses possible in a repeat treatment scheme due to the high risk of complications. Therapies administered locally also often exhibit poor diffusion through the brain parenchyma, resulting in limited brain distribution and necessitating high dosages leading to toxicity. Recent strategies focusing on temporary disruption of the BBB using chemical or mechanical methods are often spatially non-specific, also allows in undesired potentially detrimental molecules, and can induce deleterious immune responses (X. Dong, Theranostics, 8, 1481 (2018)). The clinically significant gaps in existing therapies for neurological disorders pose an urgent need to develop innovative, less-invasive, specialized drug delivery vehicles that can enhance the delivery of therapeutics across CNS barriers and target the key diseased cells at the site of injury.

Neuroinflammation mediated by activated microglia/macrophages (mi/ma) is a major hallmark of many neurological disorders (M. T. Heneka, et al., Nature Reviews 2014, 14, 463 (2014); R. M. Ransohoff, Science, 353, 777 (2016)). Pro-inflammatory mi/ma activation disrupts the BBB/BRB and can cause secondary damage through release of apoptotic signals to neurons and glia. Anti-inflammatory activation promotes vascularization and cell growth while suppressing the immune response. Therefore, targeting both pro- and anti-inflammatory mi/ma phenotypes with immune-modulating agents is a potent therapeutic strategy specific to the disease pathology. Nanocarriers that can efficiently penetrate the CNS barriers upon systemic administration, diffuse freely through brain tissue, and localize to key pathological cells at the site of CNS injury are incredibly rare (S. Kannan, et al., Science translational medicine, 4, 130ra46E (2012); J. Kwon, et al., ACS Nano 2016, 10, 7926; Y. Anraku, et al., Nature Communications, 8, 1001 (2017)). In addition to favorable brain transport properties, a key goal in the development of nanomedicine-based therapeutics for CNS disorders is designing nano-constructs that can be conveniently translated to the clinic. The primary criterion for a potential nanoparticle to be used in a clinical setup is its safety profile; other desired features include water solubility, synthetic reproducibility, and feasibility for large scale production towards successful commercialization (S. Mignani, et al., Advanced Drug Delivery Reviews (2017)).

Based on their unique structural and physical features, dendrimers have shown unprecedented potential as nanocarriers for various biomedical applications including targeted drug/gene delivery, imaging and diagnosis (Sharma, A., et al., RSC Advances, 4, 19242 (2014); Caminade, A.-M., et al., Journal of Materials Chemistry B, 2, 4055 (2014); Esfand, R., et al., Drug Discovery Today, 6, 427 (2001); and Kannan, R. M., et al., Journal of Internal Medicine, 276, 579 (2014)).

However, despite large numbers of scientific reports published on the development of facile and rapid strategies to construct dendrimers, there are still significant challenges. Thus, there remains a need for improved nanomaterial for targeted delivery system to target to the CNS.

Therefore, it is an object of the present invention to provide dendrimer compositions and methods of use thereof for improved molecular delivery to the CNS.

It is also an object of the present invention to provide means of treating diseases, disorders, and injury of the brain and central nervous system, particularly those associated with activated microglia and/or astrocytes.

It is a further object of the present invention to provide biocompatible and inexpensive nanomaterials for targeted drug delivery to the central nervous system with little to no local or systemic toxicity.

SUMMARY OF THE INVENTION

Dendrimers having a high density of hydroxyl groups of at least 1 OH group/nm$^3$ (number of hydroxyl groups/volume in nm$^3$), preferably of at least 5 OH group/nm$^3$, are described. Generally, these dendrimers have a molecular weight between about 500 Daltons to about 100,000 Daltons, preferably between about 500 Daltons to about 50,000 Daltons, most preferably between about 1,000 Daltons to about 10,000 Dalton. Typically, the dendrimers have an average diameter between about 1 nm and about 15 nm, preferably between about 1 nm and about 5 nm, most preferably between about 1 nm and about 2 nm.

Dendrimers including (a) a central core; (b) one or more branching units; and (c) terminal functional groups are described. Exemplary chemical moieties for (a), (b), and (c) are independently selected from dipentaerythritol, pentaerythritol, 2-(aminomethyl)-2-(hydroxymethyl) propane-1,3-diol, 2-ethyl-2-(hydroxymethyl) propane-1,3-diol, 3,3',3'',3'''-silanetetrayltetrakis (propane-1-thiol), 3,3-divinylpenta-1,4-diene, 3,3',3''-nitrilotripropionic acid, 3,3',3''-nitrilotris(N-(2-aminoethyl)propanamide), 3,3',3'',3'''-(ethane-1,2-diylbis(azanetriyl)) tetrapropanamide, 3-(carboxymethyl)-3-hydroxypentanedioic acid, 2,2'-((2,2-bis((2-hydroxyethoxy)methyl) propane-1,3-diyl)bis(oxy)) bis(ethan-1-ol), tetrakis(3-(trichlorosilyl) propyl)silane, 1-Thioglycerol, 2,2,4,4,6,6-hexachloro-1,3,5,215,415,615-triazatriphosphinine, 3-(hydroxymethyl)-5,5-dimethylhexane-2,4-diol, 4,4',4''-(ethane-1,1,1-triyl)triphenol, 2,4,6-trichloro-1,3,5-triazine, 5-(hydroxymethyl) benzene-1,2,3-triol, 5-(hydroxymethyl)benzene-1,3-diol, 1,3,5-tris (dimethyl(vinyl)silyl)benzene, Carbosiloxane core, nitrilotrimethanol, ethylene diamine, propane-1,3-diamine, butane-1,4-diamine, 2,2',2''-nitrilotris(ethan-1-ol), alpha cyclodextrin, beta cyclodextrin, gamma cyclodextrin, benzene-1,2,3,4,5,6-hexathiol, monosaccharide, disaccharides, trisaccharides, oligosaccharides, chitosan, and derivatives thereof. In some embodiments, the dendrimers are generation 1 (G1), G2, G3, G4, G5, G6, G7, G8, G9, or G10 dendrimers. The dendrimers have a surface hydroxyl group density between about 1 and 15 hydroxyl (—OH) groups/nm$^2$, between about 3 and 15 OH groups/nm$^2$, between about 4 and 15 OH groups/nm$^2$, between about 4 and 10 OH groups/nm$^2$, at least 1 OH groups/nm$^2$; at least 2 OH groups/nm$^2$; at least 3 OH groups/nm$^2$; at least 4 OH groups/nm$^2$; at least 5 OH groups/nm$^2$; and a molecular weight between about 500 Daltons and about 100,000 Dalton, between about 500 Daltons and about 50,000 Dalton, between about 1,000 Daltons and about 20,000 Dalton, between about 1000 Daltons and about 10,000 Dalton.

Methods of calculating surface hydroxyl group are known in the art. Surface area of dendrimers is first calculated. In the case of PAMAM dendrimers, surface area can be calculated assuming a spherical shape. A G4 hydroxyl-terminated PAMAM dendrimer has a molecular weight of about 14,215 Dalton, measured diameter of 45 Å (i.e., 4.5 nm), and 64 surface hydroxyl groups. The estimated surface area of G4 PAMAM dendrimer is calculated assuming a spherical shape by formula $A=4\pi r^2$, thus it is about 63.62 nm$^2$. Accordingly, the surface density of hydroxyl groups on a G4 PAMAM dendrimer is about 1.01 OH groups/nm$^2$. Likewise, a G5 hydroxyl-terminated PAMAM dendrimer, which has a molecular weight of about 28,826 Dalton, measured diameter of 54 Å (i.e., 5.4 nm) and 128 surface hydroxyl groups, has a surface density of hydroxyl groups about 1.4 OH groups/nm$^2$ (based on the estimated surface area of 91.61 nm$^2$). A G6 hydroxyl-terminated PAMAM dendrimer, which has a molecular weight of about 58,048 Dalton, measured diameter of 67 Å (i.e., 6.7 nm) and 256 surface hydroxyl groups, has a surface density of hydroxyl groups about 1.82 OH groups/nm$^2$ (based on the estimated surface area of 141.03 nm$^2$)

Compositions of dendrimer complexes including one or more prophylactic, therapeutic, and/or diagnostic agents encapsulated, associated, and/or conjugated in the dendrimers are also provided. Generally, one or more prophylactic, therapeutic, and/or diagnostic agent are encapsulated, associated, and/or conjugated in the dendrimer complex at a concentration of about 0.01% to about 30%, preferably about 1% to about 20%, more preferably about 5% to about 20% by weight. Preferably, prophylactic, therapeutic, and/or diagnostic agent are covalently conjugated to the dendrimer via one or more linkages selected from the group consisting of disulfide, ester, ether, thioester, carbamate, carbonate, hydrazine, and amide, optionally via one or more spacers. In some embodiments, the spacer is a prophylactic, therapeutic, and/or diagnostic agent, such as N-acetyl cysteine. Exemplary active agents include anti-inflammatory drugs, chemotherapeutics, anti-seizure agents, vasodilators, and anti-infective agents.

Methods of using the dendrimers with high density surface hydroxyl groups for treating, preventing, and/or imaging one or more symptoms of one or more diseases, conditions, and/or injuries of the eye, the brain and/or the central nervous system (CNS) by administering to a subject in need thereof are also described. Generally, these conditions are associated with pathological activation of microglia and astrocytes. The compositions target the activated microglia and astrocytes; and are effective to alleviate or prevent or image one or more symptoms of the one or more diseases, conditions, and/or injuries of the eye, the brain and/or the nervous system associated with the activated microglia and astrocytes. Typically, the dendrimer complexes are administered intravenously.

BRIEF DESCRIPTION OF THE DRAWINGS

FIGS. 6A-6D showing fold changes in mRNA levels of TNFα (FIG. 6A), INOS (FIG. 6B), IL10 (FIG. 6C), and IL6 (FIG. 6D) in BV-2 cells treated with control, LPS, or 10, 50, 100, 500 µg/ml PEGOL-60 for 24 hrs; FIGS. 6E-6G showing fold changes in mRNA levels of CD206 (FIG. 6E), Arg1 (FIG. 6F), and IL4 (FIG. 6G) in BV-2 cells treated with control, LPS, or 10, 50, 100, 500 µg/ml PEGOL-60 for 24 hrs; FIGS. 6H-6I showing amount of secreted TNFα (FIG. 6H), and production of reactive species nitrite (FIG. 6I) in BV-2 cells treated with control, LPS, or 10, 50, 100, 500 µg/ml PEGOL-60 for 24 hrs; FIG. 6J showing cell viability of BV-2 cells treated with control, $H_2O_2$, or 10, 50, 100, 500 µg/ml PEGOL-60 for 24 hrs.

FIG. 8B showing quantitative biodistribution of PEGOL-60-Cy5 in the major organs and blood plasma of neonatal cerebral palsy rabbit kits at different time points post-injection (1, 4, and 24 hrs, n=6).

DETAILED DESCRIPTION OF THE INVENTION

I. Definitions

Figures 1A, 1B, 1C, 1D, 1E, 1F:
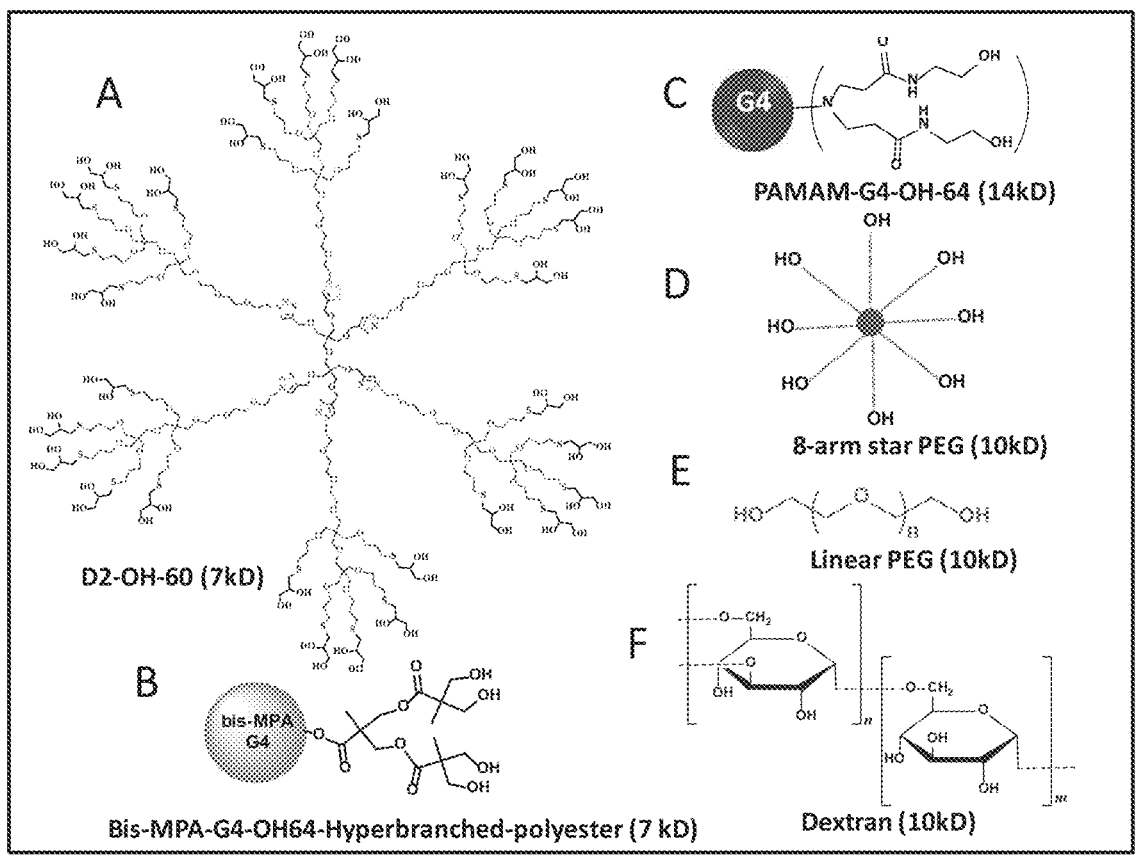
FIGS. 1A-1E are structural representations of (FIG. 1A) low generation highly dense PEG based dendrimer (D2-OH-60), (FIG. 1B) commercially available bis-MPA-G4-OH-64-hyperbranched-polyester, (FIG. 1C) generation 4 PAMAM dendrimer, (FIG. 1D) 8-arm star PEG (8-OH groups), (FIG. 1E) linear PEG (2-OH groups), and (FIG. 1F) branched polysaccharide dextran with multiple OH groups.

The term "pharmaceutically acceptable," refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration. The term "carrier" or "excipient" refers to an organic or inorganic, natural or synthetic inactive ingredient in a formulation, with which one or more active ingredients are combined. In some embodiments, a carrier or an excipient is an inert substance added to a pharmaceutical composition to facilitate administration of a compound, and/or does not cause significant irritation to an organism and does not abrogate the biological activity and properties of the administered compound.

The terms "biocompatible" and "biologically compatible," generally refer to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

The term "effective amount," or "therapeutically effective amount" refers to a nontoxic but sufficient amount of the compound to provide a desired or referenced result. For example, an effective amount can refer to a dosage sufficient to reduce or inhibit one or more symptoms of a disorder, disease, or condition being treated, or to otherwise provide a desired pharmacologic and/or physiologic effect. The precise dosage will vary according to a variety of factors such as subject-dependent variables (e.g., age, immune system health, etc.), the severity of the disease or disorder being treated, as well as the route of administration and the pharmacokinetics of the agent being administered. The exact amount required will vary from subject to subject, depending on the species, age, and general condition of the subject, the severity of the disease that is being treated, the particular compound used, and its mode of administration. An appropriate effective amount can be determined by one of ordinary skill in the art.

The term "molecular weight," generally refers to the relative average chain length of the bulk polymer, unless otherwise specified. In practice, molecular weight can be estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

The term "derivative" refers to a modification including, but not limited to, hydrolysis, reduction, or oxidation products, of the disclosed compounds. Hydrolysis, reduction, and oxidation reactions are known in the art.

The term "hydrophilic," refers to the property of having affinity for water. For example, hydrophilic polymers (or hydrophilic polymer segments) are polymers (or polymer segments) which are primarily soluble in aqueous solutions and/or have a tendency to absorb water. In general, the more hydrophilic a polymer is, the more that polymer tends to dissolve in, mix with, or be wetted by water.

The term "hydrophobic," refers to the property of lacking affinity for or repelling water. For example, the more hydrophobic a polymer (or polymer segment), the more that polymer (or polymer segment) tends to not dissolve in, not mix with, or not be wetted by water.

The term "therapeutic agent" refers to an agent that can be administered to prevent or treat a disease or disorder. Therapeutic agents can be a nucleic acid, a nucleic acid analog, a small molecule, a peptidomimetic, a protein, peptide, carbohydrate or sugar, lipid, or surfactant, or a combination thereof.

The term "treating" or "preventing" one or more symptoms of a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

The term "targeting moiety" refers to a moiety that localizes to or away from a specific locale. The moiety may be, for example, a protein, nucleic acid, nucleic acid analog, carbohydrate, or small molecule. The locale may be a tissue, a particular cell type, or a subcellular compartment.

The terms "incorporated" and "encapsulated" refers to incorporating, formulating, or otherwise including an agent into and/or onto a composition, regardless of the manner by which the agent or other material is incorporated.

II. Compositions

A. Dendrimers

Dendrimers are three-dimensional, hyperbranched, monodispersed, globular and polyvalent macromolecules including surface end groups (Tomalia, D. A., et al., Biochemical Society Transactions, 35, 61 (2007); and Sharma, A., et al., ACS Macro Letters, 3, 1079 (2014)). Due to their unique structural and physical features, dendrimers have shown unprecedented potential as nano-carriers for various biomedical applications including targeted drug/gene delivery, imaging and diagnosis (Sharma, A., et al., RSC Advances, 4, 19242 (2014); Caminade, A.-M., et al., Journal of Materials Chemistry B, 2, 4055 (2014); Esfand, R., et al., Drug Discovery Today, 6, 427 (2001); and Kannan, R. M., et al., Journal of Internal Medicine, 276, 579 (2014)).

Dendrimers are emerging as potential candidates for various biomedical applications including drug/gene delivery, targeting, imaging and diagnosis (oliman, G M et al., *Chem. Commun.* 2011, 47, 9572; and Tomalia, D A et al., *Biochem. Soc. Trans.* 2007, 35, 61). Among several different types of dendrimers, polyamidoamine (PAMAM) dendrimers have been widely explored for drug delivery applications due to their commercial availability, aqueous solubility and biocompatibility (Tomalia, D A et al., *Polym J* 1985, 17, 117). The small size and the presence of easily tunable multiple surface groups make these nanoparticles excellent carriers for the transport of drugs to CNS. Earlier studies show that noncytotoxic, hydroxyl terminated generation 4 PAMAM dendrimers (~4 nm size, without any targeting ligand) can cross the impaired BBB and target activated microglia at the site of injury in the brain several fold more than the healthy control (Lesniak, W G et al., *Mol Pharm* 2013, 10). These dendrimers are nontoxic even at intravenous doses >500 mg/kg, and are cleared intact through the kidneys. These findings were validated in various small and large animal models (Kannan, S et al., *Sci. Transl. Med.* 2012, 4, 130ra46; Kambhampati, S P et al., *Invest Ophthalmol Vis Sci* 2015, 56; Nance, E et al., *J. Control. Release* 2015, 214, 112; Mishra, M K et al., *ACS Nano* 2014, 8, 2134; and Nanomedicine 2010, 5, 1317). The selective uptake and localization of these neutral dendrimers in activated microglia might attribute to their ability to cross the impaired BBB and diffuse rapidly in the brain parenchyma followed by the uptake by constantly phagocytic activated glial cells.

Recent studies have shown that dendrimer surface groups can have a significant impact on their biodistribution (Nance, E., et al., Biomaterials, 101, 96 (2016)). More specifically, hydroxyl terminating generation 4 PAMAM dendrimers (~~4 nm size) without any targeting ligand have been shown to cross the impaired BBB upon systemic administration in a rabbit model of cerebral palsy (CP) significantly more (>20 fold) as compared to healthy controls, and selectively target activated microglia and astrocytes (Lesniak, W. G., et al., Mol Pharm, 10 (2013)). See Kannan, S., et al., Science Translational Medicine, 4, 130ra46 (2012); Iezzi, R., et al., Biomaterials, 33, 979 (2012); Mishra, M. K., et al., ACS Nano, 8, 2134 (2014); Kambhampati, S. P., et al., European Journal of Pharmaceutics and Biopharmaceutics, 95, Part B, 239 (2015); Zhang, F., et al., Journal of Controlled Release, 249, 173 (2017); Guo, Y., et al., PLOS ONE, 11, e0154437 (2016); and Inapagolla, R., et al., International Journal of Pharmaceutics, 399, 140 (2010).

The term "dendrimer" includes, but is not limited to, a molecular architecture with an interior core and layers (or "generations") of repeating units which are attached to and extend from this interior core, each layer having one or more branching points, and an exterior surface of terminal groups attached to the outermost generation. In some embodiments, dendrimers have regular dendrimeric or "starburst" molecular structures.

Generally, dendrimers have a diameter from about 1 nm up to about 50 nm, more preferably from about 1 nm to about 20 nm, from about 1 nm to about 10 nm, or from about 1 nm to about 5 nm. In some embodiments, the diameter is between about 1 nm to about 2 nm. In preferred embodiments, the dendrimers have a diameter effective to cross the blood brain barrier ("BBB") and to be retained in target cells for a prolonged period of time.

In preferred embodiments, the dendrimers include a plurality of hydroxyl groups. Some exemplary high-density hydroxyl groups-containing dendrimers include commercially available polyester dendritic polymer such as hyperbranched 2,2-Bis(hydroxyl-methyl)propionic acid polyester polymer (for example, hyperbranched bis-MPA polyester-64-hydroxyl, generation 4), dendritic polyglycerols.

Figure 9:
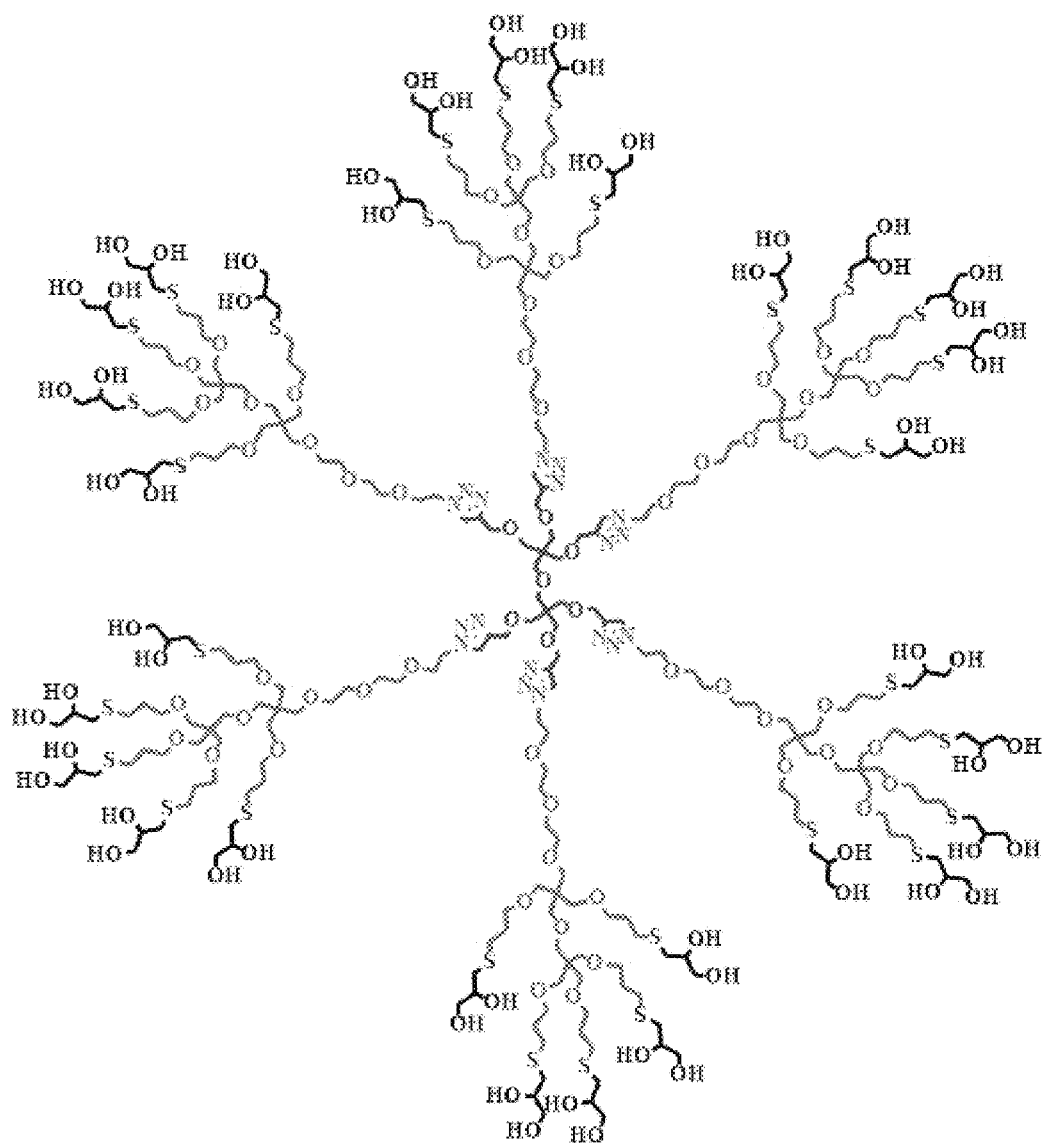
FIG. 9 (formula I).

In some embodiments, the high-density hydroxyl groups-containing dendrimers are oligo ethylene glycol (OEG)-like dendrimers. For example, a generation 2 OEG dendrimer (D2-OH-60) can be synthesized using highly efficient, robust and atom economical chemical reactions such as Cu (I) catalyzed alkyne-azide click and photo catalyzed thiol-ene click chemistry. Highly dense polyol dendrimer at very low generation in minimum reaction steps can be achieved by using an orthogonal hypermonomer and hypercore strategy. This dendrimer backbone has non-cleavable polyether bonds throughout the structure to avoid the disintegration of dendrimer in vivo and to allow the elimination of such dendrimers as a single entity from the body (non-biodegradable). In preferred embodiments, the dendrimer is as shown in Formula I (FIG. 9).

Exemplary dendrimers include, but are not limited to, polyamidoamine (PAMAM), polyester, polylysine, polypropylamine (POPAM), poly(propylene imine) (PPI), iptycene, aliphatic poly(ether), and/or aromatic polyether dendrimers. The dendrimers can have carboxylic, amine and/or hydroxyl terminations. Dendrimers can be any generation including, but not limited to, generation 1, generation 2, generation 3, generation 4, generation 5, generation 6, generation 7, generation 8, generation 9, or generation 10. In some embodiments, dendrimers are PAMAM dendrimers used as a platform and modified with surface groups for increased number of hydroxyl groups.

Each dendrimer of a dendrimer complex may be of similar or different chemical nature than the other dendrimers (e.g., the first dendrimer may include a PAMAM dendrimer, while the second dendrimer may include a POPAM dendrimer). In some embodiments, the first or second dendrimer may further include an additional agent. The multi-arm PEG polymer includes a polyethylene glycol having at least two branches bearing sulfhydryl or thiopyridine terminal groups; however, PEG polymers bearing other terminal groups such as succinimidyl or maleimide terminations can be used. The PEG polymers in the molecular weight range of 10 kDa to 80 kDa can be used.

Generally, the complete architecture of dendrimers can be distinguished into the inner core moiety followed by radially attached branching units (i.e., generations) which are further decorated with chemical functional groups carrying desired terminal groups at the exterior surface of the dendrimers.

In some embodiments, the dendrimers are in nanoparticle form and are described in detail in U.S. Published Application Nos. US 2011/0034422, US 2012/0003155, and US 2013/0136697.

The molecular weight of the dendrimers can be varied to prepare polymeric nanoparticles that form particles having properties, such as drug release rate, optimized for specific applications. The dendrimers can have a molecular weight of between about 150 Da and 1 MDa. In certain embodiments, the polymer has a molecular weight of between about 500 Da and about 100 kDa, more preferably between about 1 kDa and about 50 kDa, most preferably between about 1 kDa and about 20 kDa.

In some embodiments, different variations of dendrimers are used as a delivery vehicle to deliver one or more active agents, including, but not limited to, dendrons and tectodendrimers. Dendrons are dendritic wedges that comprise one type of functionality at the core (functional groups, f=1) and another at the periphery (f=8, 16, 32, etc. . . . ). Tectodendrimers are generally composed of a central dendrimer with multiple dendrimers attached at its periphery. In some embodiments, the active agents such as N-acetyl cysteine is conjugated to dendrons or tectodendrimers.

1. Central Core

A multifunctional core moiety allows stepwise addition of branching units (i.e., generations) around the core. The core of PAMAM is a diamine (commonly ethylenediamine), which is reacted with methyl acrylate, and then another ethylenediamine to make the generation-0 (G-0) PAMAM. Core moiety can be replaced with a different chemical moiety as appropriate. For example, PAMAM dendrimers can contain tetra(ethylene oxide) at core using click chemistry (Han S C et al., *Bull. Korean Chem. Soc.* 33, 3501-3504(2012)).

Exemplary chemical structures suitable as core moieties are listed in Table 1 including dipentaerythritol, pentaerythritol, 2-(aminomethyl)-2-(hydroxymethyl) propane-1,3-diol, 2-ethyl-2-(hydroxymethyl) propane-1,3-diol, 3,3',3'',3'''-silanetetrayltetrakis (propane-1-thiol), 3,3-divinylpenta-1,4-diene, 3,3',3''-nitrilotripropionic acid, 3,3',3''-nitrilotris(N-(2-aminoethyl)propanamide), 3,3',3'',3'-(ethane-1,2-diylbis(azanetriyl)) tetrapropanamide, 3-(carboxymethyl)-3-hydroxypentanedioic acid, 2,2'-((2,2-bis((2-hydroxyethoxy)methyl) propane-1,3-diyl)bis(oxy))bis(ethan-1-ol), tetrakis(3-(trichlorosilyl) propyl)silane, 1-Thioglycerol, 2,2,4,4,6,6-hexachloro-1,3,5,215,415,615-triazatriphosphinine, 3-(hydroxymethyl)-5,5-dimethylhexane-2,4-diol, 4,4',4''-(ethane-1,1,1-triyl)triphenol, 2,4,6-trichloro-1,3,5-triazine, 5-(hydroxymethyl) benzene-1,2,3-triol, 5-(hydroxymethyl)benzene-1,3-diol, 1,3,5-tris(dimethyl(vinyl)silyl)benzene, Carbosiloxane core, nitrilotrimethanol, ethylene diamine, propane-1,3-diamine, butane-1,4-diamine, 2,2',2''-nitrilotris(ethan-1-ol), alpha cyclodextrin, beta cyclodextrin, gamma cyclodextrin, Cucurbituril, benzene-1,2,3,4,5,6-hexathiol, monosaccharide, disaccharides, trisaccharides, oligosaccharides, or azide-, alkyne-modified moieties thereof. In some embodiments, the core moiety is chitosan. Thus, azide-modified chitosan, or alkyne-modified chitosan are suitable for conjugating to branching units using click chemistry. In some embodiments, the core moiety is ethylenediamine, or tetra(ethylene oxide).

In some embodiments, the core moiety is polyethylene glycerol linear or branched as shown in Formula II:

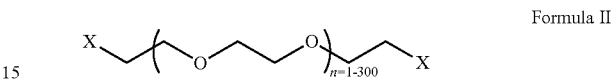

Formula II

X can be amine, acid, aldehyde, alcohol, acetylene, allyl, acrylate, azide, tosyl, mesylate, thiol, N-hydroxy succinimide activated acids, maleimide.

TABLE 1

Structural representation of various building blocks (cores, branching units, surface groups, monomers) for the synthesis of hydroxyl terminating dendrimers

| Building blocks | Structure |
| --- | --- |
| Dipentaerythritol | ![structure] |
| Pentaerythritol | ![structure] |
| 2-(aminomethyl)-2-(hydroxymethyl) propane-1,3-diol | ![structure] |
| 2-ethyl-2-(hydroxymethyl) propane-1,3-diol | ![structure] |
| 3,3',3'',3'''-silanetetrayltetrakis (propane-1-thiol) | ![structure] |
| 3,3-divinylpenta-1,4-diene | ![structure] |
| 3,3',3''-nitrilotripropionic acid | ![structure] |

TABLE 1-continued

Structural representation of various building blocks (cores, branching units, surface groups, monomers) for the synthesis of hydroxyl terminating dendrimers

| Building blocks | Structure |
|---|---|
| 3,3',3''-nitrilotris(N-(2-aminoethyl)propanamide) | 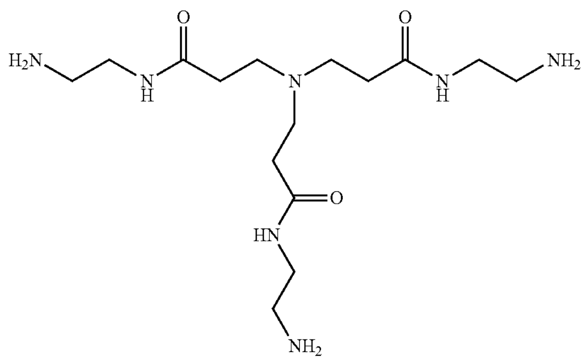 [SMILES: NCCNC(=O)CCN(CCC(=O)NCCN)CCC(=O)NCCN] |
| 3,3',3'',3'''-(ethane-1,2-diylbis(azanetriyl))tetrapropanamide | 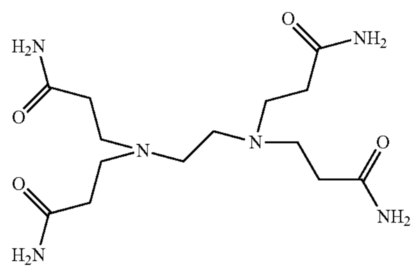 [SMILES: NC(=O)CCN(CCC(N)=O)CCN(CCC(N)=O)CCC(N)=O] |
| 3-(carboxymethyl)-3-hydroxypentanedioic acid | 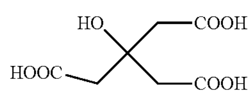 |
| 2,2'-((2,2-bis((2-hydroxyethoxy)methyl)propane-1,3-diyl)bis(oxy))bis(ethan-1-ol) | 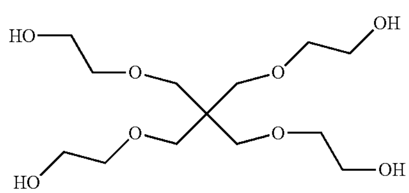 [SMILES: OCCOCC(COCCO)(COCCO)COCCO] |
| tetrakis(3-(trichlorosilyl)propyl)silane | 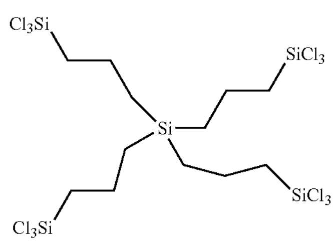 |
| 1-Thioglycerol | 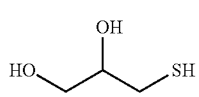 |
| All the sugar based scaffolds including mono, di, tri, or oligomers | 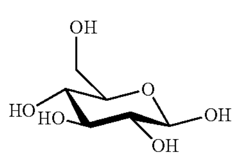 |

TABLE 1-continued

Structural representation of various building blocks (cores, branching units, surface groups, monomers) for the synthesis of hydroxyl terminating dendrimers

| Building blocks | Structure |
|---|---|
| 2,2,4,4,6,6-hexachloro-1,3,5,2l5, 4l5,6l5-triazatriphosphinine | 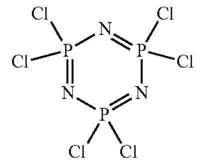 [SMILES: ClP1(Cl)=NP(Cl)(Cl)=NP(Cl)(Cl)=N1] |
| 3-(hydroxymethyl)-5,5-dimethylhexane-2,4-diol | 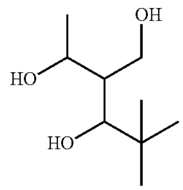 |
| 4,4',4''-(ethane-1,1,1-triyl)triphenol | 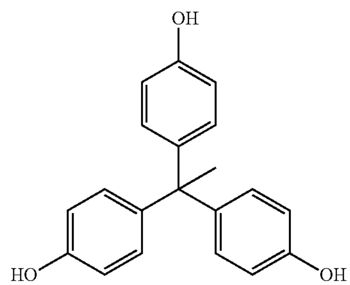 [SMILES: CC(c1ccc(O)cc1)(c1ccc(O)cc1)c1ccc(O)cc1] |
| 2,4,6-trichloro-1,3,5-triazine | 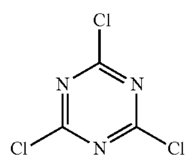 |
| 5-(hydroxymethyl)benzene-1,2,3-triol | 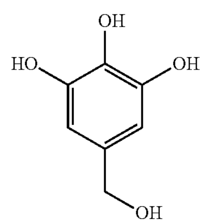 |
| 5-(hydroxymethyl)benzene-1,3-diol | 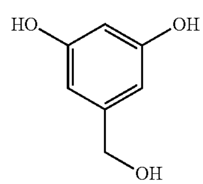 |
| 1,3,5-tris(dimethyl(vinyl)silyl)benzene | 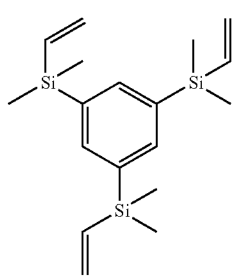 [SMILES: C=C[Si](C)(C)c1cc([Si](C)(C)C=C)cc([Si](C)(C)C=C)c1] |

TABLE 1-continued

Structural representation of various building blocks (cores, branching units, surface groups, monomers) for the synthesis of hydroxyl terminating dendrimers

| Building blocks | Structure |
| --- | --- |
| Carbosiloxane core | (structure shown) |
| nitrilotrimethanol | (structure shown) |
| ethylene diamine | (structure shown) |
| propane-1,3-diamine | (structure shown) |
| butane-1,4-diamine | (structure shown) |
| 2,2',2''-nitrilotris(ethan-1-ol) | (structure shown) |

TABLE 1-continued

Structural representation of various building blocks (cores, branching units, surface groups, monomers) for the synthesis of hydroxyl terminating dendrimers

| Building blocks | Structure |
| --- | --- |
| | [tris(piperazinyl)triazine structure] |
| benzene-1,2,3,4,5,6-hexathiol | [structure] |
| alpha cyclodextrin | [structure] |
| beta cyclodextrin | [structure] |

TABLE 1-continued

Structural representation of various building blocks (cores, branching units, surface groups, monomers) for the synthesis of hydroxyl terminating dendrimers

| Building blocks | Structure |
| --- | --- |
| gamma cyclodextrin | 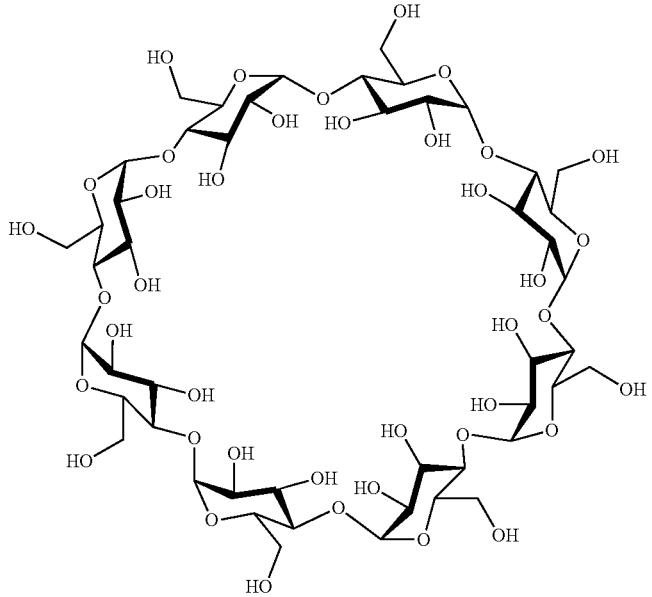 [SMILES: OCC1O[C@@H]2O[C@@H]3C(CO)O[C@H](O[C@@H]4C(CO)O[C@H](O[C@@H]5C(CO)O[C@H](O[C@@H]6C(CO)O[C@H](O[C@@H]7C(CO)O[C@H](O[C@@H]8C(CO)O[C@H](O[C@@H]9C(CO)O[C@H](O[C@H]1[C@H](O)C2O)C(O)[C@H]9O)C(O)[C@H]8O)C(O)[C@H]7O)C(O)[C@H]6O)C(O)[C@H]5O)C(O)[C@H]4O)C(O)[C@H]3O] |
| Cucurbituril | 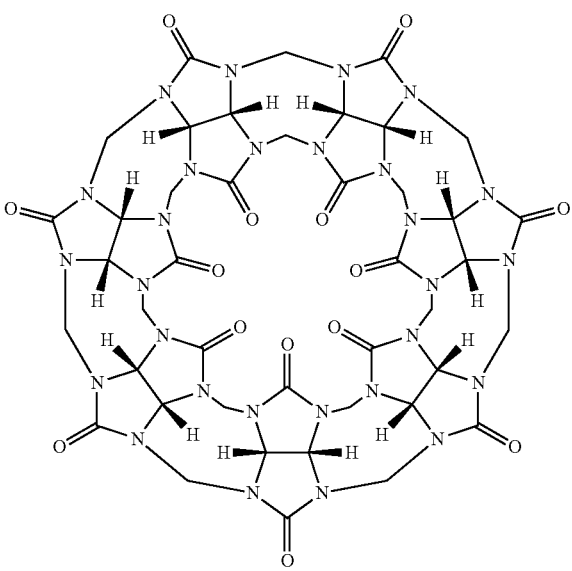 [SMILES: NCN1C(=O)N2CN3C(=O)N4CN5C(=O)N6CN7C(=O)N8CN9C(=O)N%10CN%11C(=O)N%12CN%13C(=O)N[C@@H]%14[C@H]%13N%13CN%15C(=O)N(CN%16C(=O)N(CN%17C(=O)N(CN%18C(=O)N(CN%19C(=O)N(CN%20C(=O)N(CN%14C%13=O)[C@@H]1[C@@H]2%20)[C@@H]3[C@@H]4%19)[C@@H]5[C@@H]6%18)[C@@H]7[C@@H]8%17)[C@@H]9[C@@H]%10%16)[C@@H]%11[C@@H]%12%15] |

2. Branching Units

Exemplary chemical structures suitable as branching units are listed in Table 1 including dipentaerythritol, pentaerythritol, 2-(aminomethyl)-2-(hydroxymethyl) propane-1,3-diol, 2-ethyl-2-(hydroxymethyl) propane-1,3-diol, 3,3',3",3"'-silanetetrayltetrakis (propane-i-thiol), 3,3-divinylpenta-1,4-diene, 3,3',3"-nitrilotripropionic acid, 3,3',3"-nitrilotris(N-(2-aminoethyl)propanamide), 3,3',3",3'''-(ethane-1,2-diylbis(azanetriyl)) tetrapropanamide, 3-(carboxymethyl)-3-hydroxypentanedioic acid, 2,2'-((2,2-bis((2-hydroxyethoxy)methyl) propane-1,3-diyl)bis(oxy))bis(ethan-1-ol), tetrakis (3-(trichlorosilyl) propyl)silane, 1-Thioglycerol, 2,2,4,4,6,6-hexachloro-1,3,5,2l5,4l5,6l5-triazatriphosphinine, 3-(hydroxymethyl)-5,5-dimethylhexane-2,4-diol, 4,4',4"-(ethane-1,1,1-triyl)triphenol, 2,4,6-trichloro-1,3,5-triazine, 5-(hydroxymethyl) benzene-1,2,3-triol, 5-(hydroxymethyl)benzene-1,3-diol, 1,3,5-tris(dimethyl(vinyl)silyl)benzene, Carbosiloxane core, nitrilotrimethanol, ethylene diamine, propane-1,3-diamine, butane-1,4-diamine, 2,2',2"-nitrilotris (ethan-1-ol), alpha cyclodextrin, beta cyclodextrin, gamma cyclodextrin, Cucurbituril, benzene-1,2,3,4,5,6-hexathiol, monosaccharide, disaccharides, trisaccharides, oligosaccharides, or azide-, alkyne-modified moieties thereof. In some embodiments, the branching unit is chitosan. Thus, azide-modified chitosan, or alkyne-modified chitosan are suitable for conjugating to the core moiety or additional same or different branching units using click chemistry. In some embodiments, the branching unit is methyl acrylate, or ethylenediamine.

In some embodiments, the branching unit is polyethylene glycerol linear or branched as shown in Formula II.

In some embodiments, the branching units are hyper-monomers i.e., $AB_n$ building blocks. Exemplary hyper-monomers include AB4, AB5, AB6, AB7, AB8 building blocks. Hyper-monomer strategy drastically increases the number of available end groups. An exemplary hypermonomer is AB5 orthogonal hypermonomer including one azide functional group and five allyl groups prepared from dipentaerythritol with five allyl groups reacted with mono tosylated triethylene glycol azide (Scheme 2).

3. Surface Groups

Surface groups, or terminal functional groups are not limited to a primary amine end group, a hydroxyl end group, a carboxylic acid end group, a thiol end. In some embodiments, the desired surface groups can be added via one of the conjugation methods for the core and branching unit.

Any of the chemical moieties listed in Table I can be used as surface groups to be conjugated one or more branching units via any of the common conjugation methods described above. In preferred embodiments, the surface group is 1-thioglycerol, conjugated to one or more branching unit via photochemical thiol-ene reaction.

In some embodiments, the dendrimer is able to specifically target a particular tissue region and/or cell type, preferably the cells and tissues of the central nervous system (CNS) and the eye. In some embodiments, the dendrimer is able to specifically target a site of inflammation in the body, preferably inflammation of the CNS and the eye. Linear and star polymers with hydroxyl end groups do not target the injured cells of brain and retina. However, dendrimers and dendritic polymers with a high density of hydroxyl functional groups effectively target the injured cells in a generation independent and also building block independent manner. Examples are described on how the newly synthesized dendrimers appear to target not only microglia and microphages but also other cells implicated in the brain injuries.

In preferred embodiments, the dendrimers have a plurality of hydroxyl (—OH) groups on the peripheral of the dendrimers. The preferred surface density of hydroxyl (—OH) groups is at least 1 OH group/nm$^2$ (number of hydroxyl surface groups/surface area in nm$^2$). For example, in some embodiments, the surface density of hydroxyl groups is more than 2, 3, 4, 5, 6, 7, 8, 9, 10; preferably at least 10, 15, 20, 25, 30, 35, 40, 45, 50, or more than 50. In further embodiments, the surface density of hydroxyl (—OH) groups is between about 1 and about 50, preferably 5-20 OH group/nm$^2$ (number of hydroxyl surface groups/surface area in nm$^2$) while having a molecular weight of between about 500 Da and about 10 kDa.

In some embodiments, the dendrimers may have a fraction of the hydroxyl groups exposed on the outer surface, with the others in the interior core of the dendrimers. In preferred embodiments, the dendrimers have a volumetric density of hydroxyl (—OH) groups of at least 1 OH group/nm$^3$ (number of hydroxyl groups/volume in nm$^3$). For example, in some embodiments, the volumetric density of hydroxyl groups is 2, 3, 4, 5, 6, 7, 8, 9, 10, or more than 10, 15, 20, 25, 30, 35, 40, 45, and 50. In some embodiments, the volumetric density of hydroxyl groups is between about 4 to about 50 groups/nm$^3$, preferably between about 5 to about 30 groups/nm$^3$, more preferably between about 10 to about 20 groups/nm$^3$. In the case of a generation 2 highly dense polyhydroxy dendrimer (D2-OH-60), the volumetric density of hydroxyl groups is about 14 groups/nm$^3$.

In preferred embodiments, the dendrimers include an effective number of hydroxyl groups for targeting to activated microglial and/or astrocytes associated with a disease, disorder, or injury of the CNS, or the eye.

B. Coupling Agents and Spacers

Dendrimer complexes can be formed of therapeutically active agents or compounds conjugated or attached to a dendrimer, a dendritic polymer or a hyperbranched polymer. Optionally, the active agents are conjugated to the dendrimers via one or more spacers/linkers via different linkages such as disulfide, ester, carbonate, carbamate, thioester, hydrazine, hydrazides, and amide linkages. In some embodiments, the attachment occurs via an appropriate spacer that provides a disulfide bridge between the agent and the dendrimer. In this case, the dendrimer complexes are capable of rapid release of the agent in vivo by thiol exchange reactions, under the reduced conditions found in body.

The term "spacers" include compounds used for linking a therapeutically prophylactically or diagnostically active agent to the dendrimer. The spacer can be either a single chemical entity or two or more chemical entities linked together to bridge the polymer and the therapeutic agent or imaging agent. The spacers can include any small chemical entity, peptide or polymers having sulfhydryl, thiopyridine, succinimidyl, maleimide, vinylsulfone, and carbonate terminations.

The spacer can be chosen from among compounds terminating in sulfhydryl, thiopyridine, succinimidyl, maleimide, vinylsulfone and carbonate group. The spacer can include thiopyridine terminated compounds such as dithiodipyridine, N-Succinimidyl 3-(2-pyridyldithio)-propionate (SPDP), succinimidyl 6-(3-[2-pyridyldithio]-propionamido) hexanoate (LC-SPDP) or sulfosuccinimidyl 6-(3-[2-pyridyl-dithio]-propionamido)hexanoate (Sulfo-LC-SPDP). The spacer can also include peptides wherein the peptides are linear or cyclic essentially having sulfhydryl groups such as glutathione, homocysteine, cysteine and its derivatives, arg-gly-asp-cys (RGDC), cyclo(Arg-Gly-Asp-d-Phe-Cys) (c(RGDfC)), cyclo(Arg-Gly-Asp-D-Tyr-Cys), cyclo(Arg-Ala-Asp-d-Tyr-Cys). The spacer can be a mercapto acid derivative such as 3 mercapto propionic acid, mercapto acetic acid, 4 mercapto butyric acid, thiolan-2-one, 6 mercaptohexanoic acid, 5 mercapto valeric acid and other mercapto derivatives such as 2 mercaptoethanol and 2 mercaptoethylamine. The spacer can be thiosalicylic acid and its derivatives, (4-succinimidyloxycarbonyl-methyl-alpha-2-pyridylthio)toluene, (3-[2-pyridithio]propionyl hydrazide, The spacer can have maleimide terminations wherein the spacer includes polymer or small chemical entities such as bis-maleimido diethylene glycol and bis-maleimido triethylene glycol, Bis-Maleimidoethane, bismaleimidohexane. The spacer can include vinylsulfone such as 1,6-Hexane-bis-vinylsulfone. The spacer can include thioglycosides such as thioglucose. The spacer can be reduced proteins such as bovine serum albumin and human serum albumin, any thiol terminated compound capable of forming disulfide bonds. The spacer can include polyethylene glycol having maleimide, succinimidyl and thiol terminations.

In some embodiments, the spacer/linker is Gamma-aminobutyric acid (GABA) linker, allyl linker, propargyl linker, ethane thiol linker, pyridine disulfide linker. In preferred embodiments, the spacer/linker is conjugated to the dendrimers via one or more of ether, thioester, carbamate, carbonate, hydrazine, or amide bonds for improved stability under physiological conditions, for example, compared to ester linkages.

In other embodiments, the ligation of different linkers e.g. allyl, propargyl etc. on dendrimer surface through different linkages e.g. ether, ester, carbamate, carbonate etc., which can participate in click chemistry for the conjugation of the active agent such as NAC. In further embodiments, the dendrimer is conjugated to a first active agent via one linker, whilst a second active agent via a different linker.

C. Therapeutic, Prophylactic and Diagnostic Agents

A wide range of agents may be included in the particles to be delivered. The agents can be proteins or peptides, sugars or carbohydrate, nucleic acids or oligonucleotides, lipids, small molecules, or combinations thereof. The nucleic acid can be an oligonucleotide encoding a protein, for example, a DNA expression cassette or an mRNA. Representative oligonucleotides include siRNAs, microRNAs, DNA, and RNA. In some embodiments, the active agent is a therapeutic antibody. One or more types of active agents can be encapsulated, complexed or conjugated to the dendrimer. For example, the dendrimer is conjugated to one or more NAC molecules via disulfide bridge and one or more antibodies via amide linkages.

Exemplary therapeutic agents include anti-inflammatory drugs, antiproliferatives, chemotherapeutics, vasodilators, neuroactive agents and anti-infective agents. In some embodiments, the dendrimer is linked to the targeting moiety, imaging agents, and/or therapeutic agents via a spacer ending in disulfide, ester, ether, thioester, carbamate, carbonate, hydrazine, or amide bonds.

In some embodiments, the active agent is a targeting agent. Targeting moieties include folic acid, RGD peptides either linear or cyclic, TAT peptides, LHRH and BH3.

1. Therapeutic Agents

The term "dendrimer complexes" refers to the dendrimer conjugated to or complexed with one or more therapeutic, prophylactic, or diagnostic agent. One or more therapeutic agents can be complexed with, covalently attached to or intra-molecularly dispersed or encapsulated within the dendrimer. In some embodiments, two or more different therapeutic agents can be associated, via covalent and/or non-covalent interactions, with the dendrimer.

The dendrimer complex, when administered by intravenous injection, can preferentially cross the blood brain barrier (BBB) only under diseased conditions and not under normal conditions. Preferably the agent(s) is attached or conjugated to the dendrimers, which are capable of preferentially releasing the drug at the target site i.e., site of disease, and/or injury. For example, some drugs can be released intracellularly under the reduced conditions found in vivo. The dendrimer complexes linked to an agent can be used to perform several functions including targeting, localization at a diseased site, releasing the drug, and imaging purposes. The dendrimer complexes can be tagged with or without targeting moieties. In some embodiments, a disulfide bond between the dendrimer and the agent or imaging agent is formed via a spacer or linker molecule.

In some embodiments, the molecules include antibodies, for example, daclizumab, bevacizumab (AVASTIN®), ranibizumab (LUCENTIS®), basiliximab, ranibizumab, and pegaptanib sodium or peptides like SN50, and antagonists of NF.

In some embodiments, one or more therapeutic agents targeting the underlying cause of the disease or condition, and one or more therapeutic agents relieving one or more symptoms of the disease or condition. Thus, for treating leukodystrophy, the dendrimers can be conjugated to an agent that prevents or reduces very long chain fatty acid production, an agent that promotes peroxisome proliferation, an agent that promotes very long chain fatty acid removal, an agent that increases ABCD2 expression, or a combination thereof. An example is VBP15, a dissociative steroid drug.

Preferred active agents include, but are not limited to, agents that prevent or reduce very long chain fatty acid production, agents that promote peroxisome proliferation, agents that promote very long chain fatty acid removal (e.g., 4-phenyl butyrate), agents that increase ABCD2 expression (e.g., benzafibrate), thyromimetics (e.g., eprotirome, sobetirome), enzymes (e.g. Galactosylceramidase and Arylsulfatase A, Aspartoacylase), agents that reduce neuroinflammation (e.g., N-acetyl cysteine, Pioglitazone, Vitamin E) and RNA oligonucleotides that interfere with gene transcription or translation. In particularly preferred embodiments, the agent is N-acetylcysteine, 4-phenylbutyrate, bezafibrate, thyroid hormone (T3), sobetirome, pioglitazone, resveratrol, VBP15, Vitamin E, erucic acid, Coenzyme Q10, clemastine, galactosylceramidase (GALC), Aspartoacylase (ASPA), or Arylsulfatase A (ARSA). Other suitable active agents, including, but not limited to, anti-inflammatory, neuroactive and imaging agents. The dendrimer can be conjugated to more than one agent and more than one type of agent.

In some embodiments, the compositions include one or more anti-excitotoxic and/or D-anti-glutamate agents. Exemplary compounds are MK801, Memantine, Ketamine, 1-MT.

a. Anti-Inflammatory Agents

In some embodiments, the compositions include one or more anti-inflammatory agents. Anti-inflammatory agents reduce inflammation and include steroidal and non-steroidal drugs.

A preferred antiinflammatory is an antioxidant drug including N-acetylcysteine. Preferred NSAIDS include mefenamic acid, aspirin, Diflunisal, Salsalate, Ibuprofen, Naproxen, Fenoprofen, Ketoprofen, Deacketoprofen, Flurbiprofen, Oxaprozin, Loxoprofen, Indomethacin, Sulindac, Etodolac, Ketorolac, Diclofenac, Nabumetone, Piroxicam, Meloxicam, Tenoxicam, Droxicam, Lornoxicam, Isoxicam, Meclofenamic acid, Flufenamic acid, Tolfenamic acid, elecoxib, Rofecoxib, Valdecoxib, Parecoxib, Lumiracoxib, Etoricoxib, Firocoxib, Sulphonanilides, Nimesulide, Niflumic acid, and Licofelone.

Representative small molecules include steroids such as methyl prednisone, dexamethasone, non-steroidal anti-inflammatory agents including COX-2 inhibitors, corticosteroid anti-inflammatory agents, gold compound anti-inflammatory agents, immunosuppressive, anti-inflammatory and anti-angiogenic agents, anti-excitotoxic agents such as valproic acid, D-aminophosphonovalerate, D-aminophosphonoheptanoate, inhibitors of glutamate formation/release, such as baclofen, NMDA receptor antagonists, salicylate anti-inflammatory agents, ranibizumab, anti-VEGF agents, including aflibercept, and rapamycin. Other anti-inflammatory drugs include nonsteroidal drug such as indomethacin, aspirin, acetaminophen, diclofenac sodium and ibuprofen. The corticosteroids can be fluocinolone acetonide and methylprednisolone.

Exemplary immune-modulating drugs include cyclosporine, tacrolimus and rapamycin. In some embodiments, anti-inflammatory agents are biologic drugs that block the action of one or more immune cell types such as T cells, or block proteins in the immune system, such as tumor necrosis factor-alpha (TNF-alpha), interleukin 17-A, interleukins 12 and 23.

In some embodiments, the anti-inflammatory drug is a synthetic or natural anti-inflammatory protein. Antibodies specific to select immune components can be added to immunosuppressive therapy. In some embodiments, the anti-inflammatory drug is an anti-T cell antibody (e.g., anti-thymocyte globulin or Anti-lymphocyte globulin), anti-IL-2Ra receptor antibody (e.g., basiliximab or daclizumab), or anti-CD20 antibody (e.g.., rituximab).

Many inflammatory diseases may be linked to pathologically elevated signaling via the receptor for lipopolysaccharide (LPS), toll-like receptor 4 (TLR4). There has thus been great interest in the discovery of TLR4 inhibitors as potential anti-inflammatory agents. Recently, the structure of TLR4 bound to the inhibitor E5564 was solved, enabling design and synthesis of new TLR4 inhibitors that target the E5564-binding domain. These are described in U.S. Pat. No. 8,889,101, the contents of which are incorporated by reference. As reported by Neal, et al., PLoS One. 2013; 8(6): e65779e, a similarity search algorithm used in conjunction with a limited screening approach of small molecule libraries identified compounds that bind to the E5564 site and inhibit TLR4. The lead compound, C34, is a 2-acetamidopyranoside (MW 389) with the formula $C_{17}H_{27}NO_9$, which inhibits TLR4 in enterocytes and macrophages in vitro, and reduces systemic inflammation in mouse models of endotoxemia and necrotizing enterocolitis. Thus, in some embodiments, the active agents are one or more TLR4 inhibitors. In preferred embodiments, the active agents are C34, and derivatives, analogues thereof.

In preferred embodiments, the one or more anti-inflammatory drugs are released from the dendrimeric nanoparticles after administration to a mammalian subject in an amount effective to inhibit inflammation for at least 1 day, 2 days, 3 days, 4 days, 5 days, 6 days, preferably at least a week, 2 weeks, or 3 weeks, more preferably at least a month, two months, three months, four months, five months, six months.

b. Chemotherapeutic Agents

Chemotherapeutic agents generally include pharmaceutically or therapeutically active compounds that work by interfering with DNA synthesis or function in cancer cells. Based on their chemical action at a cellular level, chemotherapeutic agents can be classified as cell-cycle specific agents (effective during certain phases of cell cycle) and cell-cycle nonspecific agents (effective during all phases of cell cycle). Examples of chemotherapeutic agents include alkylating agents, angiogenesis inhibitors, aromatase inhibitors, antimetabolites, anthracyclines, antitumor antibiotics, platinum drugs, topoisomerase inhibitors, radioactive isotopes, radiosensitizing agents, checkpoint inhibitors, PD1 inhibitors, plant alkaloids, glycolytic inhibitors and prodrugs thereof.

Examples of PD-1 inhibitors include, for example, MDX-1106 is a genetically engineered, fully human immunoglobulin G4 (IgG4) monoclonal antibody specific for human PD-1, and pembrolizumab, recently approved by the US FDA.

Representative chemotherapeutic agents include, but are not limited to, amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epipodophyllotoxins, epirubicin, etoposide, etoposide phosphate, fludarabine, fluorouracil, gemcitabine, hydroxycarb amide, idarubicin, ifosfamide, innotecan, leucovorin, liposomal doxorubicin, liposomal daunorubici, lomustine, mechlorethamine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, teniposide, tegafur-uracil, temozolomide, teniposide, thiotepa, tioguanine, topotecan, treosulfan, vinblastine, vincristine, vindesine, vinorelbine, taxol and derivatives thereof, trastuzumab (HERCEPTIN®), cetuximab, and rituximab (RITUXAN® or MABTHERA®), bevacizumab (AVASTIN®), and combinations thereof.

Representative pro-apoptotic agents include, but are not limited to, fludarabinetaurosporine, cycloheximide, actinomycin D, lactosylceramide, 15d-PGJ(2)5 and combinations thereof.

Dendrimer complexes including one or more chemotherapeutic agents can be used prior to, or in conjunction with an immunotherapy such inhibition of checkpoint proteins such as PD-1 or CTLA-4, adoptive T cell therapy, and/or a cancer vaccine. Methods of priming and activating T cells in vitro for adaptive T cell cancer therapy are known in the art. See, for example, Wang, et al, Blood, 109(11):4865-4872 (2007) and Hervas-Stubbs, et al, J. Immunol., 189(7):3299-310 (2012). Examples of cancer vaccine include, for example, PROVENGE® (sipuleucel-T), which is a dendritic cell-based vaccine for the treatment of prostate cancer (Ledford, et al., Nature, 519, 17-18 (5 Mar. 2015). Such vaccines and other compositions and methods for immunotherapy are reviewed in Palucka, et al., Nature Reviews Cancer, 12, 265-277 (April 2012).

In some embodiments, the dendrimer complexes are effective to treat, image, and/or prevent inflammation of the microglia of the brain in neurodevelopmental disorders, including, for example Rett syndrome. In a preferred embodiment, the dendrimer complex would be used to deliver an anti-inflammatory agent (D-NAC) and anti-excitotoxic and D-anti-glutamate agents. Preferred candidates are: MK801, Memantine, Ketamine, 1-MT.

c. Neuroactive Agents

A number of drugs have been developed and used in an attempt to interrupt, influence, or temporarily halt the glutamate excitotoxic cascade toward neuronal injury. One strategy is the "upstream" attempt to decrease glutamate release. This category of drugs includes riluzole, lamotrigine, and lifarizine, which are sodium channel blockers. The commonly used nimodipine is a voltage-dependent channel (L-type) blocker. Attempts have also been made to affect the various sites of the coupled glutamate receptor itself. Some of these drugs include felbamate, ifenprodil, magnesium, memantine, and nitroglycerin. These "downstream" drugs attempt to influence such intracellular events as free radical formation, nitric oxide formation, proteolysis, endonuclease activity, and ICE-like protease formation (an important component in the process leading to programmed cell death, or apoptosis).

Active agents for the treatment of neurodegenerative diseases are well known in the art and can vary based on the symptoms and disease to be treated. For example, conventional treatment for Parkinson's disease can include levodopa (usually combined with a dopa decarboxylase inhibitor or COMT inhibitor), a dopamine agonist, or an MAO-B inhibitor.

Treatment for Huntington's disease can include a dopamine blocker to help reduce abnormal behaviors and movements, or a drug such as amantadine and tetrabenazine to control movement, etc. Other drugs that help to reduce chorea include neuroleptics and benzodiazepines. Compounds such as amantadine or remacemide have shown preliminary positive results. Hypokinesia and rigidity, especially in juvenile cases, can be treated with antiparkinsonian drugs, and myoclonic hyperkinesia can be treated with valproic acid. Psychiatric symptoms can be treated with medications similar to those used in the general population. Selective serotonin reuptake inhibitors and mirtazapine have been recommended for depression, while atypical antipsychotic drugs are recommended for psychosis and behavioral problems.

Riluzole (RILUTEK®) (2-amino-6-(trifluoromethoxy) benzothiazole), an antiexcitotoxin, has yielded improved survival time in subjects with ALS. Other medications, most used off-label, and interventions can reduce symptoms due to ALS. Some treatments improve quality of life and a few appear to extend life. Common ALS-related therapies are reviewed in Gordon, *Aging and Disease,* 4(5):295-310 (2013), see, e.g., Table 1 therein. A number of other agents have been tested in one or more clinical trials with efficacies ranging from non-efficacious to promising. Exemplary agents are reviewed in Carlesi, et al., *Archives Italiennes de Biologie,* 149:151-167 (2011). For example, therapies may include an agent that reduces excitotoxicity such as talampanel (8-methyl-7H-1,3-dioxolo(2,3)benzodiazepine), a cephalosporin such as ceftriaxone, or memantine; an agent that reduces oxidative stress such as coenzyme Q10, manganoporphyrins, KNS-760704 [(6R)-4,5,6,7-tetrahydro-N6-propyl-2,6-benzothiazole-diamine dihydrochloride, RPPX], or edaravone (3-methyl-1-phenyl-2-pyrazolin-5-one, MCI-186); an agent that reduces apoptosis such as histone deacetylase (HDAC) inhibitors including valproic acid, TCH346 (Dibenzo(b,f)oxepin-10-ylmethyl-methylprop-2-ynylamine), minocycline, or tauroursodeoxycholic Acid (TUDCA); an agent that reduces neuroinflammation such as thalidomide and celastol; a neurotropic agent such as insulin-like growth factor 1 (IGF-1) or vascular endothelial growth factor (VEGF); a heat shock protein inducer such as arimoclomol; or an autophagy inducer such as rapamycin or lithium.

Treatment for Alzheimer's Disease can include, for example, an acetylcholinesterase inhibitor such as tacrine, rivastigmine, galantamine or donepezil; an NMDA receptor antagonist such as memantine; or an antipsychotic drug.

Treatment for Dementia with Lewy Bodies can include, for example, acetylcholinesterase inhibitors such as tacrine, rivastigmine, galantamine or donepezil; the N-methyl d-aspartate receptor antagonist memantine; dopaminergic therapy, for example, levodopa or selegiline; antipsychotics such as olanzapine or clozapine; REM disorder therapies such as clonazepam, melatonin, or quetiapine; anti-depression and antianxiety therapies such as selective serotonin reuptake inhibitors (citalopram, escitalopram, sertraline, paroxetine, etc.) or serotonin and noradrenaline reuptake inhibitors (venlafaxine, mirtazapine, and bupropion) (see, e.g., Macijauskiene, et al., *Medicina* (Kaunas), 48(1):1-8 (2012)).

Exemplary neuroprotective agents are also known in the art in include, for example, glutamate antagonists, antioxidants, and NMDA receptor stimulants. Other neuroprotective agents and treatments include caspase inhibitors, trophic factors, anti-protein aggregation agents, therapeutic hypothermia, and erythropoietin.

Other common active agents for treating neurological dysfunction include amantadine and anticholinergics for treating motor symptoms, clozapine for treating psychosis, cholinesterase inhibitors for treating dementia, and modafinil for treating daytime sleepiness.

d. Anti-Infective Agents

Antibiotics include beta-lactams such as penicillin and ampicillin, cephalosporins such as cefuroxime, cefaclor, cephalexin, cephydroxil, cepfodoxime and proxetil, tetracycline antibiotics such as doxycycline and minocycline, macrolide antibiotics such as azithromycin, erythromycin, rapamycin and clarithromycin, fluoroquinolones such as ciprofloxacin, enrofloxacin, ofloxacin, gatifloxacin, levofloxacin and norfloxacin, tobramycin, colistin, or aztreonam as well as antibiotics which are known to possess anti-inflammatory activity, such as erythromycin, azithromycin, or clarithromycin.

2. Diagnostic Agents

Dendrimer nanoparticles can include diagnostic agents useful for determining the location of administered particles. These agents can also be used prophylactically. Exemplary diagnostic materials include paramagnetic molecules, fluorescent compounds, magnetic molecules, and radionuclides. Suitable diagnostic agents include, but are not limited to, x-ray imaging agents and contrast media. Radionuclides also can be used as imaging agents.

Exemplary radioactive label include $^{14}C$, $^{36}Cl$, $^{57}Co$, $^{58}Co$, $^{51}Cr$, $^{125}I$, $^{131}I$, $^{111}Ln$, $^{152}Eu$, $^{59}Fe$, $^{67}Ga$, $^{32}P$, $^{186}Re$, $^{35}S$, $^{75}Se$, $^{175}Yb$. Examples of other suitable contrast agents include gases or gas emitting compounds, which are radioopaque. In some embodiments, the imaging agent to be incorporated into the dendrimer nanoparticles is a fluorophore (e.g., fluorescein isothiocyanate (FITC), phycoerythrin (PE)), an enzyme (e.g., alkaline phosphatase, horseradish peroxidase), element particles (e.g., gold particles).

D. Excipients and Devices

The compositions can be administered in combination with an excipient. In a preferred embodiment, the composition is administered via systemic route such as injection. Typical carriers are sterile water, saline, phosphate buffered saline, and other injectable carriers.

Pharmaceutical compositions formulated for administration by parenteral (intramuscular, intraperitoneal, intravenous (IV) or subcutaneous injection), enteral, and topical routes of administration are described.

1. Parenteral Administration

The dendrimers can be administered parenterally by subdural, intravenous, intrathecal, intraventricular, intraarterial, intra-amniotic, intraperitoneal, or subcutaneous routes.

For liquid formulations, pharmaceutically acceptable carriers may be, for example, aqueous or non-aqueous solutions, suspensions, emulsions or oils. Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media. The dendrimers can also be administered in an emulsion, for example, water in oil. Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Formulations suitable for parenteral administration can include antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Intravenous vehicles can include fluid and nutrient replenishers, electrolyte replenishers such as those based on Ringer's dextrose. In general, water, saline, aqueous dextrose and related sugar solutions, and glycols such as propylene glycols or polyethylene glycol are preferred liquid carriers, particularly for injectable solutions.

Injectable pharmaceutical carriers for injectable compositions are well-known to those of ordinary skill in the art (see, e.g., Pharmaceutics and Pharmacy Practice, J. B. Lippincott Company, Philadelphia, PA, Banker and Chalmers, eds., pages 238-250 (1982), and ASHP Handbook on Injectable Drugs, Trissel, 15th ed., pages 622-630 (2009)).

Formulations for convection enhanced delivery ("CED") include solutions of low molecular weight sales and sugars such as mannitol.

2. Enteral Administration

The dendrimers can be administered enterally. The carriers or diluents may be solid carriers or diluents for solid formulations, liquid carriers or diluents for liquid formulations, or mixtures thereof.

For liquid formulations, pharmaceutically acceptable carriers may be, for example, aqueous or non-aqueous solutions, suspensions, emulsions or oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Vehicles include, for example, sodium chloride solution, Ringer's dextrose, dextrose and sodium chloride, lactated Ringer's and fixed oils. Formulations include, for example, aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Vehicles can include, for example, fluid and nutrient replenishers, electrolyte replenishers such as those based on Ringer's dextrose. In general, water, saline, aqueous dextrose and related sugar solutions are preferred liquid carriers. These can also be formulated with proteins, fats, saccharides and other components of infant formulas.

3. Topical Administration

The active agent and optional delivery vehicle can be applied topically. Topical administration can include application directly to exposed tissue, vasculature or to tissues or prostheses, for example, during surgery. The preferred tissue for topical administration is the eye.

III. Methods for Making Dendrimer Nanoparticles

Methods of synthesizing dendrimers and making dendrimer nanoparticles are also described.

A. Dendrimers

Dendrimers can be prepared via a variety of chemical reaction steps. Dendrimers are usually synthesized according to methods allowing controlling their structure at every stage of construction. The dendritic structures are mostly synthesized by two main different approaches: divergent or convergent.

In some embodiments, dendrimers are prepared using divergent methods, in which the dendrimer is assembled from a multifunctional core, which is extended outward by a series of reactions, commonly a Michael reaction. The strategy involves the coupling of monomeric molecules that possesses reactive and protective groups with the multifunctional core moiety which leads to stepwise addition of generations around the core followed by removal of protecting groups. For example, PAMAM-$NH_2$ dendrimers were firstly synthesized by coupling N-(2-aminoethyl) acryl amide monomers to an ammonia core.

In other embodiments, dendrimers are prepared using convergent methods, in which dendrimers are built from small molecules that end up at the surface of the sphere, and reactions proceed inward building inward and are eventually attached to a core.

Many other synthetic pathways exist for the preparation of dendrimers, such as the orthogonal approach, accelerated approaches the Double-stage convergent method or the hypercore approach, the hypermonomer method or the branched monomer approach, the Double exponential method; the Orthogonal coupling method or the two-step approach, the two monomers approach, $AB_2$-$CD_2$ approach.

In some embodiments, the core of the dendrimer, one or more branching units, one or more linkers/spacers, and/or one or more surface groups can be modified to allow conjugation to further functional groups (branching units, linkers/spacers, surface groups, etc.), monomers, and/or active agents via click chemistry, employing one or more Copper-Assisted Azide-Alkyne Cycloaddition (CuAAC), Diels-Alder reaction, thiol-ene and thiol-yne reactions, and azide-alkyne reactions (Arseneault M et al., Molecules. 2015 May 20; 20(5):9263-94). In some embodiments, pre-made dendrons are clicked onto high-density hydroxyl polymers. 'Click chemistry' involves, for example, the coupling of two different moieties (e.g., a core group and a branching unit; or a branching unit and a surface group) via a 1,3-dipolar cycloaddition reaction between an alkyne moiety (or equivalent thereof) on the surface of the first moiety and an azide moiety (e.g., present on a triazine composition) (or equivalent thereof) (or any active end group such as, for example, a primary amine end group, a hydroxyl end group, a carboxylic acid end group, a thiol end group, etc.) on the second moiety.

In some embodiments, dendrimer synthesis replies upon one or more reactions selected from the group consisting of thiol-ene click reactions, thiol-yne click reactions, CuAAC, Diels-Alder click reactions, azide-alkyne click reactions, Michael Addition, epoxy opening, esterification, silane chemistry, and a combination thereof.

In further embodiments, the PEG-based dendrimers are synthesized rapidly in gram scale quantities, employing fewer reaction steps using orthogonal chemistries and present similar surface density (~60 terminal hydroxyl groups) at generation 2 compared to generation 4 of widely studied PAMAM dendrimer.

Any existing dendritic platforms can be used to make dendrimers of desired functionalities, i.e., with a high-density of surface hydroxyl groups by conjugating high-hydroxyl containing moieties such as 1-thio-glycerol or pentaerythritol. Exemplary dendritic platforms such as polyamidoamine (PAMAM), poly (propylene imine) (PPI), poly-L-lysine, melamine, poly (etherhydroxylamine) (PEHAM), poly (esteramine) (PEA) and polyglycerol can be synthesized and explored.

B. Dendrimer Complexes

Dendrimer complexes can be formed of therapeutically active agents or compounds conjugated or attached to a dendrimer, a dendritic polymer or a hyperbranched polymer. Conjugation of one or more active agents to a dendrimer are known in the art, and are described in detail in U.S. Published Application Nos. US 2011/0034422, US 2012/0003155, and US 2013/0136697.

In some embodiments, one or more active agents are covalently attached to the dendrimers. In some embodiments, the active agents are attached to the dendrimer via a linking moiety that is designed to be cleaved in vivo. The linking moiety can be designed to be cleaved hydrolytically, enzymatically, or combinations thereof, so as to provide for the sustained release of the active agents in vivo. Both the composition of the linking moiety and its point of attachment to the active agent, are selected so that cleavage of the linking moiety releases either an active agent, or a suitable prodrug thereof. The composition of the linking moiety can also be selected in view of the desired release rate of the active agents.

In some embodiments, the attachment occurs via one or more of disulfide, ester, ether, thioester, carbamate, carbonate, hydrazine, or amide linkages. In preferred embodiments, the attachment occurs via an appropriate spacer that provides a disulfide bridge between the agent and the dendrimer. In this case, the dendrimer complexes are capable of rapid release of the agent in vivo by thiol exchange reactions, under the reduced conditions found in body. Some suitable spacers for forming are a disulfide bridge between the agent and the dendrimer described earlier.

Linking moieties generally include one or more organic functional groups. Examples of suitable organic functional groups include secondary amides (—CONH—), tertiary amides (—CONR—), secondary carbamates (—OCONH—; —NHCOO—), tertiary carbamates (—OCONR—; —NRCOO—), ureas (—NHCONH—; —NRCONH—; —NHCONR—, —NRCONR—), carbinols (—CHOH—, —CROH—), disulfide groups, hydrazones, hydrazides, ethers (—O—), and esters (—COO—, —CH$_2$O$_2$C—, CHRO$_2$C—), wherein R is an alkyl group, an aryl group, or a heterocyclic group. In general, the identity of the one or more organic functional groups within the linking moiety can be chosen in view of the desired release rate of the active agents. In addition, the one or more organic functional groups can be chosen to facilitate the covalent attachment of the active agents to the dendrimers. In preferred embodiments, the attachment can occur via an appropriate spacer that provides a disulfide bridge between the agent and the dendrimer. The dendrimer complexes are capable of rapid release of the agent in vivo by thiol exchange reactions, under the reduced conditions found in body.

In certain embodiments, the linking moiety includes one or more of the organic functional groups described above in combination with a spacer group. The spacer group can be composed of any assembly of atoms, including oligomeric and polymeric chains; however, the total number of atoms in the spacer group is preferably between 3 and 200 atoms, more preferably between 3 and 150 atoms, more preferably between 3 and 100 atoms, most preferably between 3 and 50 atoms. Examples of suitable spacer groups include alkyl groups, heteroalkyl groups, alkylaryl groups, oligo- and polyethylene glycol chains, and oligo- and poly(amino acid) chains. Variation of the spacer group provides additional control over the release of the anti-inflammatory agents in vivo. In embodiments where the linking moiety includes a spacer group, one or more organic functional groups will generally be used to connect the spacer group to both the anti-inflammatory agent and the dendrimers.

Reactions and strategies useful for the covalent attachment of active agents to dendrimers are known in the art. See, for example, March, "Advanced Organic Chemistry," 5h Edition, 2001, Wiley-Interscience Publication, New York) and Hermanson, "Bioconjugate Techniques," 1996, Elsevier Academic Press, U.S.A. Appropriate methods for the covalent attachment of a given active agent can be selected in view of the linking moiety desired, as well as the structure of the active agents and dendrimers as a whole as it relates to compatibility of functional groups, protecting group strategies, and the presence of labile bonds.

The optimal drug loading will necessarily depend on many factors, including the choice of drug, dendrimer structure and size, and tissues to be treated. In some embodiments, the one or more active drugs are encapsulated, associated, and/or conjugated to the dendrimer at a concentration of about 0.01% to about 45%, preferably about 0.1% to about 30%, about 0.1% to about 20%, about 0.1% to about 10%, about 1% to about 10%, about 1% to about 5%, about 3% to about 20% by weight, and about 3% to about 10% by weight. However, optimal drug loading for any given drug, dendrimer, and site of target can be identified by routine methods, such as those described.

In some embodiments, conjugation of active agents and/or linkers occurs through one or more surface and/or interior hydroxyl groups. Thus, in some embodiments, the conjugation of active agents/linkers occurs via about 1%, 2%, 3%, 4%, 5% of the total available hydroxyl groups of the dendrimers prior to the conjugation. In other embodiments, the conjugation of active agents/linkers occurs on less than 5%, less than 10%, less than 15%, less than 20%, less than 25%, less than 30%, less than 35%, less than 40%, less than 45% of, less than 50%, less than 55%, less than 60%, less than 65%, less than 70%, less than 75% total available hydroxyl groups of the dendrimers prior to the conjugation. In preferred embodiments, dendrimer complexes retain an effective amount of hydroxyl groups for targeting to microglial and/or astrocytes, whilst conjugated to an effective amount of active agents for treat, prevent, and/or image the disease, disorder, and/or injury of the eye, and/or the CNS.

IV. Methods of Use

Methods of using the dendrimer complex compositions are also described. In preferred embodiments, the dendrimer complexes cross impaired or damaged BBB and target activated microglia and astrocytes.

A. Methods of Treatment

The formulations can be administered to treat disorders associated with infection, inflammation, or cancer, particular those having systemic inflammation that extends to the nervous system, especially the CNS.

Typically, an effective amount of dendrimer complexes including a combination of a dendrimer with one or more therapeutic, prophylactic, and/or diagnostic active agents are administered to an individual in need thereof. The dendrimers may also include a targeting agent, but as demonstrated by the examples, these are not required for delivery to injured tissue in the spinal cord and the brain.

In some embodiments, the dendrimer complexes include an agent that is attached or conjugated to dendrimers, which are capable of preferentially releasing the drug intracellularly under the reduced conditions found in vivo. The agent can be either covalently attached or intra-molecularly dispersed or encapsulated. The amount of dendrimer complexes administered to the subject is selected to deliver an effective amount to reduce, prevent, or otherwise alleviate one or more clinical or molecular symptoms of the disease or disorder to be treated compared to a control, for example, a subject treated with the active agent without dendrimer.

B. Conditions to be Treated

The compositions are suitable for treating one or more diseases, conditions, and injuries in the eye, the brain, and the nervous system, particularly those associated with pathological activation of microglia and astrocytes. The compositions can also be used for treatment of other diseases, disorders and injury including gastrointestinal disorders, ocular diseases and treatment of other tissues where the nerves play a role in the disease or disorder. The compositions and methods are also suitable for prophylactic use.

The dendrimer complex composition, preferably with a diameter under 15 nm and a hydroxyl group surface density at least 3 OH groups/nm$^2$, preferably under 10 nm and a hydroxyl group surface density of at least 4 OH groups/nm$^2$, more preferably under 5 nm and a hydroxyl group surface density of at least 5 OH groups/nm$^2$, and most preferably between 1-2 nm and a hydroxyl group surface density at least 4 OH groups/nm$^2$, delivering a therapeutic, prophylactic or diagnostic agent, selectively targets microglia and astrocytes, which play a key role in the pathogenesis of many disorders and conditions including neurodevelopmental, neurodegenerative diseases, necrotizing enterocolitis, and brain cancer. Thus, the dendrimer complexes are administered in a dosage unit amount effective to treat or alleviate conditions associated with the pathological conditions of microglia and astrocytes. Generally, by targeting these cells, the dendrimers deliver agent specifically to treat neuroinflammation.

Microglia are a type of neuroglia (glial cell) located throughout the brain and spinal cord. Microglia account for 10-15% of all cells found within the brain. As the resident macrophage cells, they act as the first and main form of active immune defense in the central nervous system (CNS). Microglia play a key role after CNS injury, and can have both protective and deleterious effects based on the timing and type of insult (Kreutzberg, G. W. Trends in Neurosciences, 19, 312 (1996); Watanabe, H., et al., Neuroscience Letters, 289, 53 (2000); Polazzi, E., et al., Glia, 36, 271 (2001); Mallard, C., et al., Pediatric Research, 75, 234 (2014); Faustino, J. V., et al., The Journal of Neuroscience: The Official Journal Of The Society For Neuroscience, 31, 12992 (2011); Tabas, I., et al., Science, 339, 166 (2013); and Aguzzi, A., et al., Science, 339, 156 (2013)). Changes in microglial function also affect normal neuronal development and synaptic pruning (Lawson, L. J., et al., Neuroscience, 39, 151 (1990); Giulian, D., et al., The Journal Of Neuroscience: The Official Journal Of The Society For Neuroscience, 13, 29 (1993); Cunningham, T. J., et al., The Journal of Neuroscience: The Official Journal Of The Society For Neuroscience, 18, 7047 (1998); Zietlow, R., et al., The European Journal Of Neuroscience, 11, 1657 (1999); and Paolicelli, R. C., et al., Science, 333, 1456 (2011)). Microglia undergo a pronounced change in morphology from ramified to an amoeboid structure and proliferate after injury. The resulting neuroinflammation disrupts the blood-brain-barrier at the injured site, and cause acute and chronic neuronal and oligodendrocyte death. Hence, targeting pro-inflammatory microglia should be a potent and effective therapeutic strategy. The impaired BBB in neuroinflammatory diseases can be exploited for transport of drug carrying nanoparticles into the brain.

In preferred embodiments, the dendrimers are administered in an amount effective to treat microglial-mediated pathology in the subject in need thereof without any associated toxicity.

In some embodiments, the subject to be treated is a human. In some embodiments, the subject to be treated is a child, or an infant. All the methods can include the step of identifying and selecting a subject in need of treatment, or a subject who would benefit from administration with the described compositions.

1. Ocular Diseases and Injuries

The compositions and methods are suitable for treatment of discomfort, pain, dryness, excessive tearing, injuries, infections, burns associated with the eye.

Examples of eye disorders that may be treated include amoebic keratitis, fungal keratitis, bacterial keratitis, viral keratitis, onchorcercal keratitis, bacterial keratoconjunctivitis, viral keratoconjunctivitis, corneal dystrophic diseases, Fuchs' endothelial dystrophy, meibomian gland dysfunction, anterior and posterior blepharitis, conjunctival hyperemia, conjunctival necrosis, cicatrical scaring and fibrosis, punctate epithelial keratopathy, filamentary keratitis, corneal erosions, thinning, ulcerations and perforations, Sjogren's syndrome, Stevens-Johnson syndrome, autoimmune dry eye diseases, environmental dry eye diseases, corneal neovascularization diseases, post-corneal transplant rejection prophylaxis and treatment, autoimmune uveitis, infectious uveitis, anterior uveitis, posterior uveitis (including toxoplasmosis), pan-uveitis, inflammatory disease of the vitreous or retina, endophthalmitis prophylaxis and treatment, macular edema, macular degeneration, age-related macular degeneration, proliferative and non-proliferative diabetic retinopathy, hypertensive retinopathy, an autoimmune disease of the retina, primary and metastatic intraocular melanoma, other intraocular metastatic tumors, open angle glaucoma, closed angle glaucoma, pigmentary glaucoma and combinations thereof. Other disorders include injury, burn, or abrasion of the cornea, cataracts and age related degeneration of the eye or vision associated therewith.

In preferred embodiments, the eye disorder to be treated is age-related macular degeneration (AMD). Age-related macular degeneration (AMD) is a neurodegenerative, neuroinflammatory disease of the macula, which is responsible for central vision loss. The pathogenesis of age-related macular degeneration involves chronic neuroinflammation in the choroid (a blood vessel layer under the retina), the retinal pigment epithelium (RPE), a cell layer under the neurosensory retina, Bruch's membrane and the neurosensory retina, itself.

2. Neurological and Neurodegenerative Diseases

Neurodegenerative diseases are chronic progressive disorders of the nervous system that affect neurological and behavioral function and involve biochemical changes leading to distinct histopathologic and clinical syndromes (Hardy H, et al., Science. 1998; 282:1075-9). Abnormal proteins resistant to cellular degradation mechanisms accumulate within the cells. The pattern of neuronal loss is selective in the sense that one group gets affected, whereas others remain intact. Often, there is no clear inciting event for the disease. The diseases classically described as neurodegenerative are Alzheimer's disease, Huntington's disease, and Parkinson's disease.

Neuroinflammation, mediated by activated microglia and astrocytes, is a major hallmark of various neurological disorders making it a potential therapeutic target (Hagberg, H et al., *Annals of Neurology* 2012, 71, 444; Vargas, D L et al., *Annals of Neurology* 2005, 57, 67; and Pardo, C A et al.,

*International Review of Psychiatry* 2005, 17, 485). Multiple scientific reports suggest that mitigating neuroinflammation in early phase by targeting these cells can delay the onset of disease and can in turn provide a longer therapeutic window for the treatment (Dommergues, M A et al., *Neuroscience* 2003, 121, 619; Perry, V H et al., *Nat Rev Neurol* 2010, 6, 193; Kannan, S et al., *Sci. Transl. Med.* 2012, 4, 130ra46; and Block, M L et al., *Nat Rev Neurosci* 2007, 8, 57). The delivery of therapeutics across blood brain barrier is a challenging task. The neuroinflammation causes disruption of blood brain barrier (BBB). The impaired BBB in neuroinflammatory disorders can be utilized to transport drug loaded nanoparticles across the brain (Stolp, H B et al., *Cardiovascular Psychiatry and Neurology* 2011, 2011, 10; and Ahishali, B et al., *International Journal of Neuroscience* 2005, 115, 151).

The compositions and methods can also be used to deliver active agents for the treatment of a neurological or neurodegenerative disease or disorder or central nervous system disorder. In preferred embodiments, the compositions and methods are effective in treating, and/or alleviating neuroinflammation associated with a neurological or neurodegenerative disease or disorder or central nervous system disorder. The methods typically include administering to the subject an effective amount of the composition to increase cognition or reduce a decline in cognition, increase a cognitive function or reduce a decline in a cognitive function, increase memory or reduce a decline in memory, increase the ability or capacity to learn or reduce a decline in the ability or capacity to learn, or a combination thereof.

Neurodegeneration refers to the progressive loss of structure or function of neurons, including death of neurons. For example, the compositions and methods can be used to treat subjects with a disease or disorder, such as Parkinson's Disease (PD) and PD-related disorders, Huntington's Disease (HD), Amyotrophic Lateral Sclerosis (ALS), Alzheimer's Disease (AD) and other dementias, Prion Diseases such as Creutzfeldt-Jakob Disease, Corticobasal Degeneration, Frontotemporal Dementia, HIV-Related Cognitive Impairment, Mild Cognitive Impairment, Motor Neuron Diseases (MND), Spinocerebellar Ataxia (SCA), Spinal Muscular Atrophy (SMA), Friedreich's Ataxia, Lewy Body Disease, Alpers' Disease, Batten Disease, Cerebro-Oculo-Facio-Skeletal Syndrome, Corticobasal Degeneration, Gerstmann-Straussler-Scheinker Disease, Kuru, Leigh's Disease, Monomelic Amyotrophy, Multiple System Atrophy, Multiple System Atrophy With Orthostatic Hypotension (Shy-Drager Syndrome), Multiple Sclerosis (MS), Neurodegeneration with Brain Iron Accumulation, Opsoclonus Myoclonus, Posterior Cortical Atrophy, Primary Progressive Aphasia, Progressive Supranuclear Palsy, Vascular Dementia, Progressive Multifocal Leukoencephalopathy, Dementia with Lewy Bodies (DLB), Lacunar syndromes, Hydrocephalus, Wernicke-Korsakoff's syndrome, post-encephalitic dementia, cancer and chemotherapy-associated cognitive impairment and dementia, and depression-induced dementia and pseudodementia.

In some embodiments, the disorder is a peroxisomal disorder or leukodystrophy characterized by detrimental effects on the growth or maintenance of the myelin sheath that insulates nerve cells. The leukodystrophy can be, for example, 18q Syndrome with deficiency of myelin basic protein, Acute Disseminated Encephalomyeolitis (ADEM), Acute Disseminated Leukoencephalitis, Acute Hemorrhagic Leukoencephalopathy, X-Linked Adrenoleukodystrophy (ALD), Adrenomyeloneuropathy (AMN), Aicardi-Goutieres Syndrome, Alexander Disease, Adult-onset Autosomal Dominant Leukodystrophy (ADLD), Autosomal Dominant Diffuse Leukoencephalopathy with neuroaxonal spheroids (HDLS), Autosomal Dominant Late-Onset Leukoencephalopathy, Childhood Ataxia with diffuse CNS Hypomyelination (CACH or Vanishing White Matter Disease), Canavan Disease, Cerebral Autosomal Dominant Arteropathy with Subcortical Infarcts and Leukoencephalopathy (CADASIL), Cerebrotendinous Xanthomatosis (CTX), Craniometaphysical Dysplasia with Leukoencephalopathy, Cystic Leukoencephalopathy with RNASET2, Extensive Cerebral White Matter abnormality without clinical symptoms, Familial Adult-Onset Leukodystrophy manifesting as cerebellar ataxia and dementia, Familial Leukodystrophy with adult onset dementia and abnormal glycolipid storage, Globoid Cell Leukodystrophy (Krabbe Disease), Hereditary Adult Onset Leukodystrophy simulating chronic progressive multiple sclerosis, Hypomyelination with Atrophy of the Basal Ganglia and Cerebellum (HABC), Hypomyelination, Hypogonadotropic, Hypogonadism and Hypodontia (4H Syndrome), Lipomembranous Osteodysplasia with Leukodystrophy (Nasu Disease), Metachromatic Leukodystrophy (MLD), Megalencephalic Leukodystrophy with subcortical Cysts (MLC), Neuroaxonal Leukoencephalopathy with axonal spheroids (Hereditary diffuse leukoencephalopathy with spheroids—HDLS), Neonatal Adrenoleukodystrophy (NALD), Oculodetatoldigital Dysplasia with cerebral white matter abnormalities, Orthochromatic Leukodystrophy with pigmented glia, Ovarioleukodystrophy Syndrome, Pelizaeus Merzbacher Disease (X-linked spastic paraplegia), Refsum Disease, Sjogren-Larssen Syndrome, Sudanophilic Leukodystrophy, Van der Knaap Syndrome (Vacuolating Leukodystrophy with Subcortical Cysts or MLC), Vanishing White Matter Disease (VWM) or Childhood ataxia with diffuse central nervous system hypomyelination, (CACH), X-linked Adrenoleukodystrophy (X-ALD), and Zellweger Spectrum disorders including Zellweger Syndrome, Neonatal Adrenoleukodystrophy, Infantile Refsum Disease, Leukoencephalopathy with brainstem and spinal cord involvement and lactate elevation (LBSL), or DARS2 Leukoencephalopathy. In preferred embodiments, the leukodystrophy is adrenoleukodystrophy (ALD) (including X-linked ALD), metachromatic leukodystrophy (MLD), Krabbe disease (globoid leukodystrophy), or DARS2 Leukoencephalopathy.

In some embodiments, the subject has an excitotoxicity disorder. Excitotoxicity is a process through which nerve cells become damaged because they are overstimulated. A number of conditions are linked with excitotoxicity including stroke, traumatic brain injury, multiple sclerosis, amyotrophic lateral sclerosis, Alzheimer's disease, and spinal injuries. Damage to the nerve cells results in corresponding neurological symptoms which can vary depending on which cells are damaged and how extensive the damage is. Once damaged, nerve cells cannot be repaired and the patient can experience permanent impairment. A number of drugs have been developed and used in an attempt to interrupt, influence, or temporarily halt the glutamate excitotoxic cascade toward neuronal injury. One strategy is the "upstream" attempt to decrease glutamate release. This category of drugs includes riluzole, lamotrigine, and lifarizine, which are sodium channel blockers. The commonly used nimodipine is a voltage-dependent channel (L-type) blocker. Attempts have also been made to affect the various sites of the coupled glutamate receptor itself. Some of these drugs include felbamate, ifenprodil, magnesium, memantine, and nitroglycerin. These "downstream" drugs attempt to influence such intracellular events as free radical formation, nitric oxide formation, proteolysis, endonuclease activity, and ICE-like protease formation (an important component in the process leading to programmed cell death, or apoptosis). Thus, in some embodiments, the dendrimer complexes include one or more active agent for treating excitotoxicity disorder.

In some embodiments, the subject has a nervous system disorder or is in need of neuroprotection. Exemplary conditions and/or subjects include, but are not limited to, subjects having had, subjects with, or subjects likely to develop or suffer from a stroke, a traumatic brain injury, a spinal cord injury, Post-Traumatic Stress syndrome, or a combination thereof.

In some embodiments, the compositions and methods are administered to a subject in need thereof in an effective amount to reduce, or prevent one or more molecular or clinical symptoms of a neurodegenerative disease, or one or more mechanisms that cause neurodegeneration.

Active agents for the treatment of neurodegenerative diseases are well known in the art and can vary based on the symptoms and disease to be treated. For example, conventional treatment for Parkinson's disease can include levodopa (usually combined with a dopa decarboxylase inhibitor or COMT inhibitor), a dopamine agonist, or an MAO-B inhibitor.

Treatment for Huntington's disease can include a dopamine blocker to help reduce abnormal behaviors and movements, or a drug such as amantadine and tetrabenazine to control movement, etc. Other drugs that help to reduce chorea include neuroleptics and benzodiazepines. Compounds such as amantadine or remacemide have shown preliminary positive results. Hypokinesia and rigidity, especially in juvenile cases, can be treated with antiparkinsonian drugs, and myoclonic hyperkinesia can be treated with valproic acid. Psychiatric symptoms can be treated with medications similar to those used in the general population. Selective serotonin reuptake inhibitors and mirtazapine have been recommended for depression, while atypical antipsychotic drugs are recommended for psychosis and behavioral problems.

Riluzole (RILUTEK®) (2-amino-6-(trifluoromethoxy) benzothiazole), an antiexcitotoxin, has yielded improved survival time in subjects with ALS. Other medications, most used off-label, and interventions can reduce symptoms due to ALS. Some treatments improve quality of life and a few appear to extend life. Common ALS-related therapies are reviewed in Gordon, *Aging and Disease*, 4(5):295-310 (2013), see, e.g., Table 1 therein. A number of other agents have been tested in one or more clinical trials with efficacies ranging from non-efficacious to promising. Exemplary agents are reviewed in Carlesi, et al., *Archives Italiennes de Biologie*, 149:151-167 (2011). For example, therapies may include an agent that reduces excitotoxicity such as talampanel (8-methyl-7H-1,3-dioxolo(2,3)benzodiazepine), a cephalosporin such as ceftriaxone, or memantine; an agent that reduces oxidative stress such as coenzyme Q10, manganoporphyrins, KNS-760704 [(6R)-4,5,6,7-tetrahydro-N6-propyl-2,6-benzothiazole-diamine dihydrochloride, RPPX], or edaravone (3-methyl-1-phenyl-2-pyrazolin-5-one, MCI-186); an agent that reduces apoptosis such as histone deacetylase (HDAC) inhibitors including valproic acid, TCH346 (Dibenzo(b,f)oxepin-10-ylmethyl-methylprop-2-ynylamine), minocycline, or tauroursodeoxycholic Acid (TUDCA); an agent that reduces neuroinflammation such as thalidomide and celastol; a neurotropic agent such as insulin-like growth factor 1 (IGF-1) or vascular endothelial growth factor (VEGF); a heat shock protein inducer such as arimoclomol; or an autophagy inducer such as rapamycin or lithium.

Treatment for Alzheimer's Disease can include, for example, an acetylcholinesterase inhibitor such as tacrine, rivastigmine, galantamine or donepezil; an NMDA receptor antagonist such as memantine; or an antipsychotic drug.

Treatment for Dementia with Lewy Bodies can include, for example, acetylcholinesterase inhibitors such as tacrine, rivastigmine, galantamine or donepezil; the N-methyl d-aspartate receptor antagonist memantine; dopaminergic therapy, for example, levodopa or selegiline; antipsychotics such as olanzapine or clozapine; REM disorder therapies such as clonazepam, melatonin, or quetiapine; anti-depression and antianxiety therapies such as selective serotonin reuptake inhibitors (citalopram, escitalopram, sertraline, paroxetine, etc.) or serotonin and noradrenaline reuptake inhibitors (venlafaxine, mirtazapine, and bupropion) (see, e.g., Macijauskiene, et al., *Medicina* (Kaunas), 48(1):1-8 (2012)).

Exemplary neuroprotective agents are also known in the art in include, for example, glutamate antagonists, antioxidants, and NMDA receptor stimulants. Other neuroprotective agents and treatments include caspase inhibitors, trophic factors, anti-protein aggregation agents, therapeutic hypothermia, and erythropoietin.

Other common active agents for treating neurological dysfunction include amantadine and anticholinergics for treating motor symptoms, clozapine for treating psychosis, cholinesterase inhibitors for treating dementia, and modafinil for treating daytime sleepiness.

3. Neurodevelopmental Disorder

Neurodevelopmental disorder generally implies that the brain is not formed normally from the beginning. Abnormal regulation of fundamental neurodevelopmental processes may occur, or there may be disruption by insult that may take various forms. Autism and attention deficit hyperactivity disorder have been classically described as neurodevelopmental disorders.

Cerebral palsy (CP) is one of the most common pediatric neurological/neurodevelopmental disorder, currently estimated to affect approximately 2 to 3 per thousand live births (Kirby, R S et al., Research in Developmental Disabilities, 32, 462 (2011)). CP is recognized in early childhood and the condition persists throughout the life. The most common causes of CP include prematurity, hypoxia-ischemia and placental insufficiency, birth asphyxia and maternal-fetal inflammation (Dammann, O. *Acta Padiatrica* 2007, 96, 6; Yoon, B H et al., *American Journal of Obstetrics and Gynecology* 2000, 182, 675; and O'Shea, T M et al., *Journal of child neurology* 2012, 27, 22).

Although CP is heterogeneous in etiology and mechanism of disease is very complex, however, neuroinflammation is a common pathophysiologic mechanism that is involved irrespective of the etiology. Targeting neuroinflammation and delivering drugs directly at the injured site can be beneficial.

The compositions and methods can also be used to deliver active agents for the treatment of a neurodevelopmental disorder, such as cerebral palsy. In preferred embodiments, the compositions and methods are effective in treating, and/or alleviating neuroinflammation associated with a neurodevelopmental disorder, such as cerebral palsy.

In some embodiments, the dendrimer complexes are effective to treat, image, and/or prevent inflammation of the microglia of the brain in neurodevelopmental disorders, including, for example Rett syndrome. In a preferred embodiment, the dendrimer complex would be used to deliver an anti-inflammatory agent (D-NAC) and anti-excitotoxic and D-anti-glutamate agents. Preferred candidates are: MK801, Memantine, Ketamine, 1-MT.

In some embodiments, the dendrimer complexes are effective to treat, image, and/or prevent inflammation of the microglia of the brain in autism spectrum disorders. The term "spectrum" refers to the wide range of symptoms, skills, and levels of impairment or disability that children with ASD can have. Some children are mildly impaired by their symptoms, while others are severely disabled. The latest edition of the Diagnostic and Statistical Manual of Mental Disorders (DSM-5) no longer includes Asperger's syndrome; although the characteristics of Asperger's syndrome are included within the broader category of ASD.

At this time, the only medications approved by the FDA to treat aspects of ASD are the antipsychotics risperidone (Risperdal) and aripripazole (Abilify). Some medications that may be prescribed off-label for children with ASD include the following:

Antipsychotic medications are more commonly used to treat serious mental illnesses such as schizophrenia. These medicines may help reduce aggression and other serious behavioral problems in children, including children with ASD. They may also help reduce repetitive behaviors, hyperactivity, and attention problems.

Antidepressant medications, such as fluoxetine or sertraline, are usually prescribed to treat depression and anxiety but are sometimes prescribed to reduce repetitive behaviors. Some antidepressants may also help control aggression and anxiety in children with ASD.

Stimulant medications, such as methylphenidate (RITALIN®), are safe and effective in treating people with attention deficit hyperactivity disorder (ADHD). Methylphenidate has been shown to effectively treat hyperactivity in children with ASD as well. But not as many children with ASD respond to treatment, and those who do have shown more side effects than children with ADHD and not ASD.

The dendrimer conjugates should have efficacy for treatment and diagnosis of such individuals, particularly in view of recent studies showing that patients with autism have evidence of neuroinflammation as seen by increased presence of activated microglia and astocytes in post-mortem brain specimems and in CSF levels of cytokines. Vargas, et al., Ann Neurol. 2005 January; 57(1):67-81. Erratum in: Ann Neurol. 2005 February; 57(2):304.

4. Brain Tumors

Effective blood-brain tumor barrier (BBTB) penetration and uniform solid tumor distribution of the disclosed dendrimer can significantly enhance therapeutic delivery to brain tumors. High density hydroxyl surface groups with their small size, near neutral surface charge, selectively localize in cells associated with inflammation, particularly neuroinflammation.

The compositions and methods are useful for treating subjects having benign or malignant tumors by delaying or inhibiting the growth of a tumor in a subject, reducing the growth or size of the tumor, inhibiting or reducing metastasis of the tumor, and/or inhibiting or reducing symptoms associated with tumor development or growth.

The types of cancer that can be treated with the compositions and methods include, but are not limited to, brain tumors including glioma, glioblastoma, gliosarcoma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma, ganglioma, Schwannoma, cordomas and pituitary tumors.

The dendrimer complexes can be administered in combination with one or more additional therapeutically active agents, which are known to be capable of treating brain tumors or the symptoms associated therewith.

For example, the dendrimers may be administered to the brain via intravenous administration or during surgery to remove all or a part of the tumor. The dendrimers may be used to deliver chemotherapeutic agents, agents to enhance adjunct therapy such as of a subject undergoing radiation therapy, wherein the hydroxyl-terminated dendrimers are covalently linked to at least one radiosensitizing agent, in an amount effective to suppress or inhibit the activity of DDX3 in the proliferative disease in the brain.

It will be understood by those of ordinary skill in the art, that in addition to chemotherapy, surgical intervention and radiation therapy are also used in treatment of cancers of the nervous system. Radiation therapy means administering ionizing radiation to the subject in proximity to the location of the cancer in the subject. In some embodiments, the radiosensitizing agent is administered in two or more doses and subsequently, ionizing radiation is administered to the subject in proximity to the location of the cancer in the subject. In further embodiments, the administration of the radiosensitizing agent followed by the ionizing radiation can be repeated for 2 or more cycles.

Typically, the dose of ionizing radiation varies with the size and location of the tumor, but is dose is in the range of 0.1 Gy to about 30 Gy, preferably in a range of 5 Gy to about 25 Gy.

In some embodiments, the ionizing radiation is in the form of sterotactic ablative radiotherapy (SABR) or sterotactic body radiation therapy (SBRT).

5. Gastrointestinal Disorders

The innate immune receptor toll-like receptor 4 (TLR4) has been recognized as the receptor on hematopoietic and non-hematopoietic cells for bacterial endotoxin (lipopolysaccharide, "LPS"), as well as for a variety of endogenous molecules that are released during inflammatory or infectious disorders. A number of diseases have been attributed to exaggerated TLR4 signaling, including both infectious and non-infectious processes. These include necrotizing enterocolitis (NEC), abdominal sepsis, pneumonia, arthritis, pancreatitis and atherosclerosis. In a preferred embodiment, the disease to be treated is NEC.

In preferred embodiments, a singular dendrimer complex composition can simultaneously treat, and/or diagnose multiple symptoms at two distinct locations of a human body including the gastrointestinal track and the central nervous system. For example, the dendrimer complex composition, including a dendrimer linked to a therapeutic, prophylactic or diagnostic agent, can treat the gastrointestinal area via enteral administration whilst selectively targeting to microglia and astrocytes after absorption into the blood stream. Microglia and astrocytes play a key role in the pathogenesis of NEC.

C. Dosages and Effective Amounts

In some in vivo approaches, the dendrimer complexes are administered to a subject in a therapeutically effective amount. The term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease or disorder, and the treatment being effected.

Generally, the dose of the compositions can be about 0.0001 to about 1000 mg/kg body weight of the subject being treated, from about 0.01 to about 100 mg/kg body weight, from about 0.1 mg/kg to about 10 mg/kg, and from about 0.5 mg to about 5 mg/kg body weight. The subjects are typically mammals, most preferably, humans. Generally, for intravenous injection or infusion, the dosage may be lower.

For example, dendrimer complex compositions can be in an amount effective to deliver one or more active agents to cells at or nearby the site of inflammation, particularly inflammation of the central nervous system, or inflammation of the eye. Therefore, in some embodiments, the dendrimer complex compositions including one or more active agent are in an amount effective to ameliorate inflammation in a subject. In a preferred embodiment, the effective amount of dendrimer complex compositions does not induce significant cytotoxicity in the cells of a subject compared to an untreated control subject. Preferably, the amount of dendrimer complex compositions is effective to prevent or reduce inflammation and/or further associated symptoms of a disease or disorder in a subject compared to an untreated control.

In general, the timing and frequency of administration will be adjusted to balance the efficacy of a given treatment or diagnostic schedule with the side-effects of the given delivery system. Exemplary dosing frequencies include continuous infusion, single and multiple administrations such as hourly, daily, weekly, monthly or yearly dosing.

In some embodiments, dosages are administered once, twice, or three times daily, or every other day, two days, three days, four days, five days, or six days to a human. In some embodiments, dosages are administered about once or twice every week, every two weeks, every three weeks, or every four weeks. In some embodiments, dosages are administered about once or twice every month, every two months, every three months, every four months, every five months, or every six months.

It will be understood by those of ordinary skill that a dosing regimen can be any length of time sufficient to treat the disorder in the subject. The term "chronic" means that the length of time of the dosage regimen can be hours, days, weeks, months, or possibly years.

In some embodiments, the regimen includes one or more cycles of a round of therapy followed by a drug holiday (e.g., no drug). The round of the therapy can be, for example, and of the administrations discussed above. Likewise, the drug holiday can be 1, 2, 3, 4, 5, 6, or 7 days; or 1, 2, 3, 4 weeks, or 1, 2, 3, 4, 5, or 6 months.

The dendrimer complexes can be administered in combination with one or more additional therapeutically active agents, which are known to be capable of treating conditions or diseases discussed above.

D. Controls

The effect of dendrimer complex compositions can be compared to a control. Suitable controls are known in the art and include, for example, untreated cells or an untreated subject. In some embodiments, the control is untreated tissue from the subject that is treated, or from an untreated subject. Preferably the cells or tissue of the control are derived from the same tissue as the treated cells or tissue. In some embodiments, an untreated control subject suffers from, or is at risk from the same disease or condition as the treated subject.

E. Combinations

The dendrimer complex compositions can be administered alone, or in combination with one or more additional active agent(s), as part of a therapeutic or prophylactic treatment regime. The dendrimer complex compositions can be administered on the same day, or a different day than the second active agent. For example, compositions including dendrimer complex compositions can be administered on the first, second, third, or fourth day, or combinations thereof.

The term "combination" or "combined" is used to refer to either concomitant, simultaneous, or sequential administration of two or more agents. Therefore, the combinations can be administered either concomitantly (e.g., as an admixture), separately but simultaneously (e.g., via separate intravenous lines into the same subject), or sequentially (e.g., one of the compounds or agents is given first followed by the second).

Examples

Example 1: Synthesis of Generation 2 Highly Dense Polyhydroxy Dendrimer (D2-OH-60, Also Known as PEGOL-60)

Methods and Materials
Reagents

All the reagents were used as received unless otherwise stated. Propargyl bromide solution (80 wt % in toluene), allyl bromide, sodium hydride (60% dispersion in mineral oil), 2,2-dimethoxy-2-phenylacetophenone, 1-thioglycerol, N-(3-dimethylaminopropyl)-N'-ethylcarbodiimide hydrochloride (EDC), 4-(dimethylamino)pyridine (DMAP), N,N'-diisopropylethylamine (DIPEA), p-toluenesulfonyl chloride, tetraethylene glycol, trifluoroacetic acid (TFA), γ-(Boc-amino)butyric acid (BOC-GABA-OH), copper sulphate pentahydrate, sodium ascorbate, anhydrous dichloromethane (DCM), anhydrous tetrahydrofuran (THF), and anhydrous dimethylformamide (DMF) were purchased from Sigma-Aldrich (St. Louis, MO, USA). Cy5-mono-NHS ester and FITC were purchased from Amersham Biosciences-GE Healthcare. All other ACS grade solvents were from Fisher Scientific. Deuterated solvents dimethylsulfoxide (DMSO-d6), water ($D_2O$), methanol ($CD_3OD$), and chloroform ($CDCl_3$) were purchased from Cambridge Isotope Laboratories, Inc. (Andover, Massachusetts). Dialysis membrane (MW cut-off 1000 Da) was obtained from Spectrum Laboratories Inc. (Rancho Dominguez, CA, USA).

Synthesis of Intermediates and Dendrimers

Preparation of compound 2: Dipentaerythritol (1) (5 g, 19.66 mmol) was dissolved in anhydrous dimethylformamide (DMF) 30 ml and stirred at 0° C. Sodium hydride (5.66 g, 235.83 mmol) was slowly added in portions to the stirring solution and was stirred for 15 minutes. It was followed by the addition of propargyl bromide (24.23 ml, 163.10 mmol, of an 80% w/w solution in toluene) at 0° C. and stirring was continued at room temperature for another 6h. The reaction mixture was cooled and partitioned between water (40 mL) and ethyl acetate (50 mL). The organic layer was washed with water (3×50 mL) and brine (2×50 mL), then dried ($Na_2SO_4$), filtered, and evaporated in vacuo. The crude product was purified by silica flash column chromatography (ethyl acetate/hexane 15:85 v/v) to afford compound 2 in 60% yield.

Preparation of compound 3: Dipentaerythritol (1) (6 g, 23.59 mmol) was dissolved in anhydrous DMF (20 mL) and tetrahydrofuran (THF, 50 mL); and the solution was stirred at 0° C. Sodium hydride (6.23 g, 259.55 mmol) was slowly added in portions to the stirring solution and was stirred for 15 minutes. It was followed by the slow addition of allyl bromide (11.2 mL, 129.77 mmol) diluted with anhydrous THF (20 mL) at 0° C.; and the stirring was continued at 0° C. for another 30 minutes followed by stirring at room temperature ("rt") (25° C.) for 90 minutes. The reaction was constantly monitored with the help of TLC. Reaction was quenched with ice once the maximum product formation was observed on TLC. TLC was stained with $KMnO_4$ dip. The reaction mixture was cooled and partitioned between water (40 mL) and ethyl acetate (50 mL). The organic layer was washed with water (3×50 mL) and brine (2×50 mL), then dried (Na2SO4), filtered, and evaporated in vacuo. The crude product was purified by silica flash column chromatography (ethyl acetate/hexane 25:75 v/v) to afford compound 3 in 40% yield. 1H NMR (500 MHz, CDCl3) δ 5.87 (ddd, J=22.5, 10.6, 5.4 Hz, 5H), 5.24 (dd, J=17.2, 1.5 Hz, 5H), 5.21-5.10 (m, 5H), 4.01-3.90 (m, 10H), 3.70 (s, 2H), 3.46 (dd, J=26.4, 13.1 Hz, 14H).

Preparation of Compound 4: P-toluenesulfonyl chloride (10.5 g, 57 mmole) in 80 ml of methylene chloride was added dropwise to a mixture of 2-(2-(2-azidoethoxy)ethoxy) ethan-1-ol (5 g, 28.5 mmol) and (12 ml, 85 mmol) of triethylamine at 0° C. The mixture was then stirred overnight at room temperature. On completion, organic layer is washed with dilute solution of HCl 3 times and then with brine. The methylene chloride was removed under reduced pressure and the crude material was purified by flash chromatography on silica using 30% ethyl acetate in hexane to afford compound 4 as a colorless oil in 80% yield. 1H NMR (500 MHz, CDCl3) δ 7.81 (d, J=8.3 Hz, 2H), 7.35 (d, J=8.2 Hz, 2H), 4.19-4.15 (m, 2H), 3.73-3.69 (m, 2H), 3.67-3.63 (m, 2H), 3.61 (s, 4H), 3.37 (t, J=5.0 Hz, 2H), 2.46 (s, 3H).

Preparation of compound 5: Compound 3 (1 g, 2.19 mmol) was dissolved in anhydrous DMF (15 mL) and stirred at 0° C. Sodium hydride (132 mg, 5.47 mmol) was slowly added in portions to the stirring solution and the solution was stirred for 15 minutes. It was followed by the slow addition of 2-(2-(2-azidoethoxy)ethoxy)ethyl 4-methylbenzenesulfonate4 (862 mg, 2.63 mmol) and stirring was continued at 0° C. for another 180 minutes. The reaction was monitored with the help of TLC. Reaction was quenched with saturated solution of ammonium chloride and extracted with ethyl acetate. The organic layer was washed with water (3×50 mL) and brine (2×50 mL), then dried (Na2SO4), filtered, and evaporated in vacuo. TLC was stained with $KMnO_4$ dip. The crude product was purified by silica flash column chromatography (ethyl acetate/hexane 25:75 v/v) to afford compound 5 in 70% yield. $^1$H NMR (500 MHz, CDCl$_3$) δ 5.92 (ddt, J=21.5, 10.6, 5.3 Hz, 5H), 5.38-5.23 (m, 5H), 5.18 (dd, J=10.5, 1.2 Hz, 5H), 4.06-3.90 (m, 10H), 3.82-3.55 (m, 10H), 3.55-3.34 (m, 18H).HRMS (ESI$^+$-TOF) m/z: calculated for $C_{31}H_{53}N_3O_9[M+H]^+$: 612.7770; found: 612.3852.

Preparation of compound 6: Hexapropargylated compound 2 (1 eq.) and an azido derivative (eq. per acetylene) were suspended in a 1:1 mixture of DMF and water in a 5 mL microwave vial equipped with a magnetic stir bar. To this were added CuSO4·5H$_2$O (0.5 eq. per acetylene) and sodium ascorbate (0.5 eq. per acetylene) dissolved in the minimum amount of water. The vial was tightly capped and reaction was irradiated in a microwave at 50° C. for 6 h. Reaction completion was monitored with the help of TLC and on completion the reaction mixture was diluted with ethyl acetate (60 mL). The organic layer was washed with a saturated solution of EDTA (3-4 times) and dried with anhydrous sodium sulphate followed by concentration in vacuo. This procedure has been extensively demonstrated to remove trace amount of copper salts. Desired compound was purified using column chromatography using 3% methanol in DCM as eluent to afford transparent oil like compound in 65% yield. $^1$H NMR (500 MHz, CDCl$_3$) δ 7.69 (s, 6H), 5.94-5.77 (m, 30H), 5.18 (dd, J=57.0, 13.8 Hz, 60H), 4.51 (s, 24H), 3.96-3.84 (m, 72H), 3.68-3.49 (m, 52H), 3.51-3.27 (m, 108H). (MALDI-TOF) m/z: calculated for $C_{24}H_{352}N_{18}O_{61}$: 4153.2400; found: 4153.4610.

Preparation of compound 8: A 10 ml glass vial was charged with alkene terminated dendrimer 6 (370 mg, 0.08 mmol), and 1-thioglycerol 7 (1.54 ml, 17.8 mmol), in 4 mL DMF. 2, 2-Dimethoxy-2-phenylacetophenone (140 mg, 0.53 mmol)was added and the reaction mixture was stirred under UV light (365 nm) for 12 hr. After 12 hr, the reaction was stopped and reaction mixture was precipitated using diethyl ether. The precipitates formed were washed several times with diethyl ether to remove excess of 1-thioglycerol. The residue was dissolved in DMF and dialysed against DMF for 6 h, followed by water dialysis for 8 h using dialysis membrane corresponding to 1000 MWCO. The purified product was then lyophilized to achieve transparent oil in 70% yield. 1H NMR (500 MHz, MeOD) δ 8.01 (s, 6H), 4.58 (d, 28H), 3.95 (s, 12H), 3.80-3.73 (m, 32H), 3.65 (s, 36H), 3.62 (d, 36H), 3.56 (m, 56H), 3.54-3.51 (m, 60H), 3.48-3.44 (m, 30H), 3.40 (s, 50H), 3.37 (s, 60H), 2.73 (dd, 30H), 2.67 (t, J=7.0 Hz, 60H), 2.60 (dd, 28H), 1.95-1.76 (m, 60H). 13C NMR (126 MHz, MeOD) δ 144.7, 124.3, 73.1, 71.4, 70.5, 70.1, 69.4, 64.6, 63.9, 50.0, 47.1, 45.6, 42.1, 35.0, 29.6, 29.1, 26.8. (MALDI-TOF) m/z: calculated for $C_{304}H_{592}N_{18}O_{121}S_{30}$: 7397.8850; found: 7425.4480. HPLC purity: 95.4%, Retention time: 8.0 minutes.

Dynamic Light Scattering (DLS) and Zeta Potential (ξ)

The size and ξ-potential distribution of PEGOL-60 was determined by dynamic light scattering (DLS) using a Zetasizer Nano ZS (Malvern Instrument Ltd. Worchester, U.K) equipped with a 50 mW He-Ne laser (633 nm). The dendrimer was dissolved in deionized water (18.2 Ω) to make concentration of 0.5 mg/mL. The solution was filtered through a cellulose acetate membrane (0.2 micron, PALL Life Science) and DLS measurements were performed in triplicate, at 25° C. with a scattering angle of 173°. For zeta potential measurement, the dendrimer was dissolved in 10 mM sodium chloride solution to get a concentration of 0.1 mg/mL. The readings were performed in triplicate and average value was recorded.

Nuclear Magnetic Resonance (1H and 13C{1H}NMR)

1H and 13C{1H}NMR spectra were recorded on a Bruker 500 MHz spectrometer at ambient temperatures. The chemical shifts are reported in ppm relative to tetramethylsilane (TMS) as an internal standard. The residual protic solvent of CDCl3 (1H, δ 7.27 ppm; 13C, δ 77.0 ppm (central resonance of the triplet)), D2O (1H, 84.79 ppm), and CD3OD (1H, 83.31 ppm and 13C, δ 49.0 ppm) were used for chemical shifts calibration. The resonance multiplicity in the 1H NMR spectra are indicated as "s" (singlet), "d" (doublet), "t" (triplet), and "m" (multiplet). The broad resonances are expressed by "b".

High Performance Liquid Chromatography (HPLC)

The purities of compounds were analyzed using HPLC (Waters Corporation, Milford, Massachusetts). The HPLC is equipped with a 1525 binary pump, an In-Line degasser AF, a 717 plus autosampler, a 2998 photodiode array detector, and a 2475 multi λ fluorescence detector interfaced with Waters Empower software. A Symmetry C18 reverse phase column (Waters) was used having 5 μm particle size, 25 cm length, and 4.6 mm internal diameter. The HPLC chromatograms were monitored at 210 nm using PDI detector and the fluorescently labeled conjugate was monitored at both 650 and 210 nm using both PDI and fluorescence detectors. The injection was run using a gradient flow starting with 90:10 (H$_2$O/ACN), gradually increasing to 10:90 (H$_2$O/CAN) in 20 min and returning to 90:10 (H$_2$O/ACN) in 25 min maintaining a flow rate of 1 mL/min.

Mass Spectroscopy

Accurate mass measurements (HRMS) were performed on BrukermicroTOF-II mass spectrometer using ESI in positive mode and direct flow sample introduction in CH$_3$CN:H$_2$O (9:1) solvent system. Either protonated molecular ions [M+nH]n+ or adducts [M+nX]n+(X=Na, K, NH$_4$) were used for empirical formula confirmation. MALDI-TOF experiments were performed on Bruker Autoflex MALDI-TOF instrument using linear positive mode and laser poer 55-100%. Sinapinic acid was used as the matrix.

Results

It was hypothesized that the presence of highly dense hydroxyl groups on the surface of dendrimers could be the driving force for targeted accumulation of these dendrimers at the site of neuroinflammation. Motivated by this hypothesis, a PEG based dendrimer with high density of surface hydroxyl groups was prepared. The neuroinflammation-targeting generation 2 PEG dendrimer nanoparticle was developed by terminating 60 hydroxyl groups (PEGOL-60) using biocompatible, inexpensive, and water soluble building blocks via highly efficient chemical transformations based on click chemistry.

The particles breach the impaired BBB and accumulates in activated microglia, astrocytes and other cells at the injured site in the brain/retina. A commercially available bis-MPA hyperbranched polyester dendrimer with comparable surface density of hydroxyl groups (64 OH) was also evaluated.

The synthesis of a PEG based dendrimer, D2-OH-60 (also referred to as PEGOL-60) was accomplished using a hypercore and hyper monomer strategy to achieve numerous end groups at lower generations in minimum synthetic steps. The dendrimer was built using highly efficient and robust chemical reactions such as copper (I) catalyzed alkyne azide click (CuAAC) and thiol-ene click chemistry (Sharma, A., et al., ACS Macro Letters, 3, 1079 (2014); and Rostovtsev, V. V., et al., Angewandte Chemie International Edition, 41, 2596 (2002)). The hyper core 2 was synthesized by performing propargylation of dipentaerythritol 1 in the presence of NaH and propargyl bromide to achieve the hexa-propargylated product in 60% yield (Scheme 1). The NMR spectrum clearly showed the presence of six propargyl protons.

Scheme 1.
Synthesis of hypercore (2)

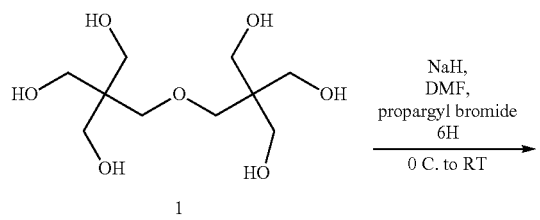

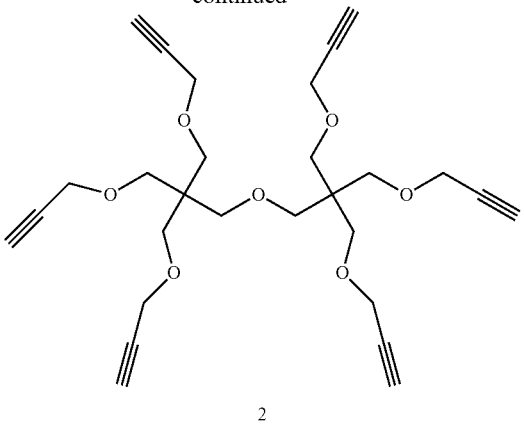

Figure 10A:
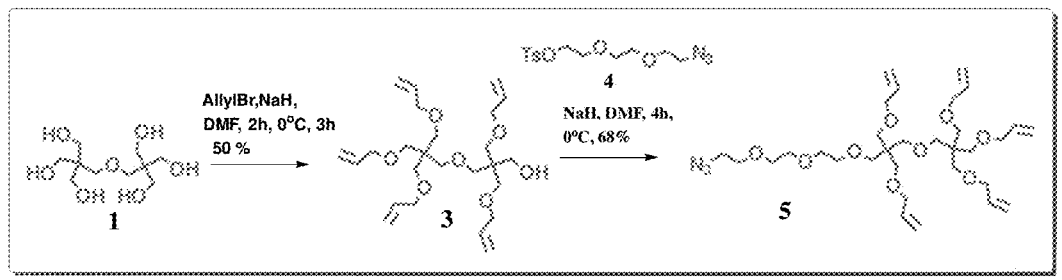
FIG. 10A Scheme 2. Synthesis of hyper monomer (5).

Hypermonomer 5 was prepared in two synthetic steps (Scheme 2). FIG. 10A. In the first step, the allylation reaction was carried out on dipentaerythritol 1 to selectively obtain AB5 monomer with five allyl groups keeping one hydroxyl arm intact. The pure product 3 was isolated by performing column chromatography from a mixture of tri-, tetra-, penta- and hexa-allylated products. The compound 3 was then reacted with mono tosylated triethylene glycol azide 4 to achieve AB5 orthogonal hypermonomer 5 with one azide functional group and five allyl groups. The purpose of azide group is to participate in CuAAC click reaction on the core 2, while the alkene groups can be exploited for photo-catalysed thiol-ene click reaction with thiolated monomers.

Figure 10B:
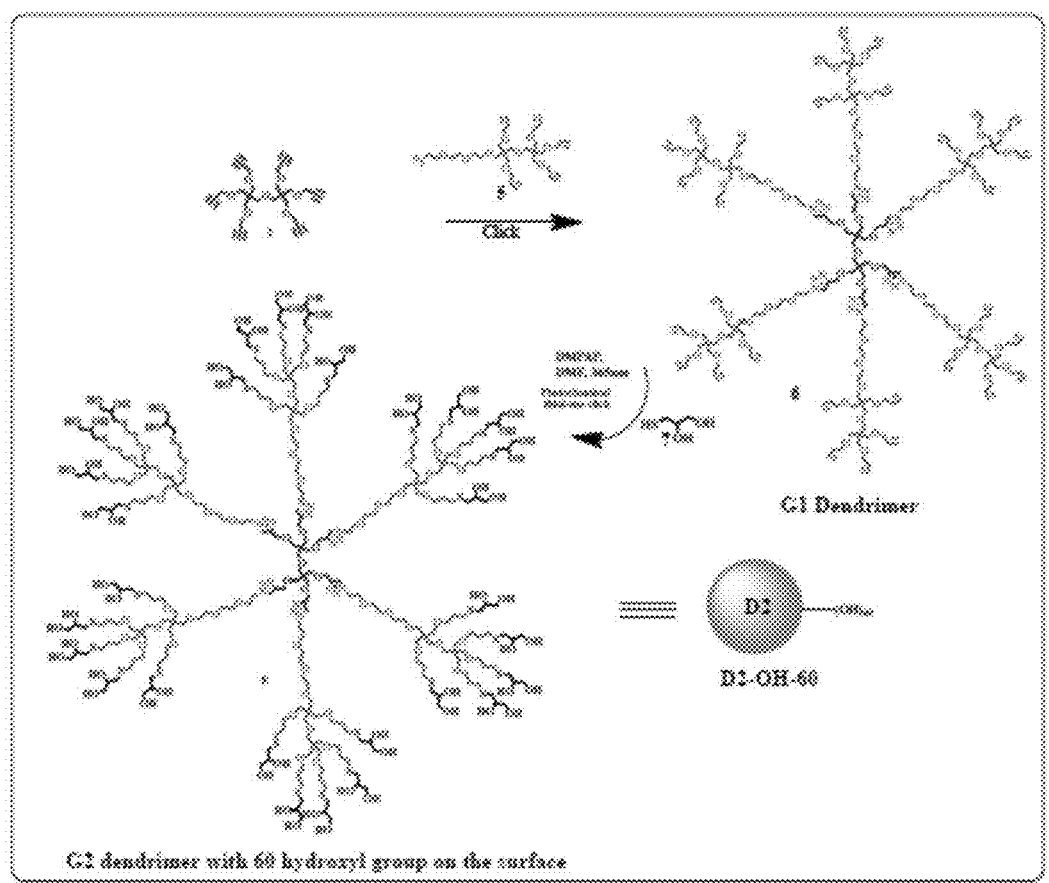
FIG. 10B Scheme 3. Synthesis of generation 2 dendrimer (8) with 60 terminal hydroxyl groups.

The hypercore 2 and hypermonomer 5 were then subjected to CuAAC click reaction to yield generation1 dendrimer (6) with 30 terminal alkene functions. See Scheme 3 Synthesis of generation 2 dendrimer (8) with 60 terminal hydroxyl groups. FIG. 10B.

The $^1$H NMR revealed the appearance of allyl protons at 5.8, 5.2, and 3.9 ppm while showing the evident disappearance of propargyl protons at 2.4 ppm. Additionally, a distinct sharp peak for triazole protons appeared in $^1$H NMR at 7.69 ppm. The theoretical molecular weight of compound (6) is 4153.24 Da and MALDI-ToF analysis revealed a peak at 4156.49 Da confirming the formation of the product. The compound 6 (D1-allyl 30) was reacted with 1-thio glycerol (7) via thiol-ene click reaction to yield generation 2 dendrimer with 60 hydroxyl groups at the surface (D2-OH-60 or PEGOL-60, 8). $^1$H NMR showed the complete disappearance of allyl end groups and the appearance of protons from thio-glycerol groups (2.8-2.5 ppm), along with the characteristic methylene protons at 1.8 ppm. Usually the $^1$H NMR characterization of dendrimers is challenging due to the presence of overlapping signals from numerous protons but for the construction of PEGOL-60 the sequential appearance and complete disappearance of characteristic allyl and propragyl signals allows simple and robust characterization tool to precisely confirm its structure.

HPLC further confirms the purity, with the products showing clear shifts in the retention time at each step. D1-allyl 30 (compound 6) has a retention time of 12.8 minutes, and the final dendrimer PEGOL-60 (compound 8), which is comparatively more polar, has a retention time of 7.1 minutes at 210 nm. MALDI-TOF spectrum shows a peak at 7433 Da, in close agreement with the theoretical molecular weight of PEGOL-60 of 7398 Da. PEGOL-60 has a size of 1.9±0.2 nm and a near-neutral zeta potential (−1.90±0.67 mV). All other intermediates and final compounds were characterized using 1H NMR, MALDI-ToF, HRMS, and HPLC.

To overcome traditional challenges in scaling up dendrimer synthesis, nsynthetic strategies have been developed to produce complex dendritic structures with high purity and efficiency. For the construction of PEGOL-60, a combination of hypercore-hypermonomer and orthogonal approaches was used and developed an accelerated scheme to construct this dendrimer with a high density of surface hydroxyl groups at lower generations (60 at generation 2 compared to 64 at generation 4 for PAMAM dendrimers) (R. Sharma, et al., Polymer Chemistry, 5, 4321 (2014); R. Sharma, et al., Chemical Communications 2014, 50, 13300). Using this accelerated approach, PEGOL-60 was synthesized in four reaction steps starting from the core via highly efficient and orthogonal chemical transformations based on Cu (I)-catalyzed alkyne azide (CuAAC) and thiol-ene click chemistry (V. V. Rostovtsev, et al., Angewandte Chemie International Edition, 41, 2596 (2002); Hoyle C E, et al., Angewandte Chemie International Edition 2010, 49, 1540). The key to produce defect-free dendrimers lies in the chemical transformations employed to couple building blocks in a layer-by-layer fashion. Conventional coupling reactions which appear to be efficient at lower generations become sluggish at higher generations with a higher number of reactive terminals due to steric crowding, which leads to structural defects and asymmetry. The click chemistry concept has become a valuable synthetic tool that comprises a pool of reactions which are easy to execute, highly robust, high yielding, atom economical, and modular in nature. Among the list of click transformations, CuAAC and thiol-ene click are the two most powerful and widely applied because they are highly facile, orthogonal, and stereoselective. These click transformations have been successfully employed in polymer chemistry, bio-conjugation reactions, dendrimer synthesis, and the generation of huge libraries of chemical entities (Moses J E et al., Chemical Society Reviews 2007, 36, 1249).

Example 2: Conjugation of Fluorescent Imaging Agents to Dendrimeric Nanoparticles Methods and Materials
Synthesis of Intermediates and Dendrimers
Preparation of compound 9: To a stirring solution of dendrimer 8(620 mg, 0.08 mmoles) in DMF (10 mL) was added BOC-GABA-OH (85 mg, 0.41 mmoles) followed by the addition of EDC (160 mg, 0.83 mmoles) and DMAP (103 mg, 0.83 mmoles). The reaction mixture was then stirred at RT for 24 h. Upon completion, the reaction mixture was dialyzed against DMF for 6 h followed by water dialysis for 12 h changing water after every 4 h. The aqueous solution was then lyophilized to yield compound 9.1H NMR (500 MHz, MeOD) δ 7.94 (s, 7H), 4.54-4.48 (m, 24H), 3.88 (s, 16H), 3.75-3.63 (m, 29H), 3.60-3.53 (m, 66H), 3.53-3.47 (m, 44H), 3.47-3.42 (m, 56H), 3.41-3.36 (m, 24H), 3.33 (s, 55H), 3.26 (s, 38H), 2.71-2.45 (m, 122H), 1.78 (dd, J=20.4, 14.4 Hz, 68H), 1.39 (s, 45H).HPLC purity: 95.4%, Retention time: 18.2 minutes Preparation of compound 10: To a stirring solution of compound 9(620 mg, 0.08 mmoles) in dry DCM (3 mL), was added trifluoroacetic acid (0.6 mL) drop wise. The reaction mixture was stirred overnight at RT. The solvent was then evaporated and the reaction mixture was diluted with methanol followed by evaporation on rotary evaporated. This process was repeated several times to remove traces of TFA. The solvent was evaporated to afford compound 10 as off-white hygroscopic solid in quantitative yield.

Preparation of compound 11: To a stirring solution of compound 10 (600 mg, 0.07 mmoles) in DMF (5 mL) was added DIPEA (0.2 mL to adjust pH of the solution to 7.4) followed by the addition of Cy5 NHS ester (55 mg, 0.15 mmoles) dissolved in 1 mL DMF. The stirring was continued at RT for 12 h. The reaction mixture was dialyzed against DMF for 12 h, changing DMF every 4 h followed by water dialysis for 6 h. The aqueous solution was then lyophilized to afford compound 11 as blue solid in % yield. $^1$H NMR (500 MHz, DMSO) δ 8.37 (t, J=12.9 Hz, Cy5 H), 8.00 (s, triazole H), 7.82 (s, Cy5 H), 7.64 (t, J=6.9 Hz, Cy5 H), 7.33 (d, J=8.3 Hz, Cy5 H), 6.59 (t, J=12.3 Hz, Cy5 H), 6.31 (d, J=7.6 Hz, Cy5 H), 4.76-4.65 (m, dendrimer H), 4.64-4.39 (m, dendrimer H), 4.14 (m, dendrimer H), 3.82 (s, dendrimer H), 3.69-3.12 (m, dendrimer H), 2.72-2.30 (m, dendrimer H), 1.80-1.61 (m, dendrimer H), 1.32-1.14 (m, cy5 H), 1.10 (t, J=7.0 Hz, Cy5 H), 0.99 (t, J=7.2 Hz, Cy5 H).HPLC purity: 92.3%, Retention time: 12.1 minutes Preparation of compound 13: To a stirring solution of G4-64OH-polyester-hyperbranched-bis-MPA 12 (2 g, 0.27 mmoles) in DMF (20 mL) was added BOC-GABA-OH (280 mg, 1.36 mmoles) followed by the addition of EDC (470 mg, 2.5 mmoles) and DMAP (305 mg, 2.5 mmoles). The reaction mixture was then stirred at RT for 24 h. Upon completion, the reaction mixture was dialyzed against DMF for 12 h followed by water dialysis for 12 h changing water after every 3 h. The aqueous solution was then lyophilized to yield compound 13. Yield: 76%. $^1$H NMR (500 MHz, DMSO) δ 4.25-4.10 (m, dendrimerH), 3.59-3.34 (m, dendrimer H), 1.63 (dt, J=13.8, 6.7 Hz, gaba linker H), 1.37 (s, BOC H), 1.15-0.95 (m, dendrimer H).

Preparation of compound 14: To a stirring solution of compound 13(1 g, 0.13 mmoles) in dry DCM (2 ml), was added TFA (1.5 ml) drop wise. The reaction mixture was stirred overnight at RT. The solvent was then evaporated and the reaction mixture was diluted with methanol followed by evaporation on rotary evaporated. This process was repeated several times to remove traces of TFA. The solvent was evaporated to afford compound 14 in quantitative yield.

Preparation of compound 15: To a stirring solution of compound 14 (200 mg, 0.02 mmoles) in DMF (3 mL) was added DIPEA (0.1 ml to adjust pH to 7.4) followed by the addition of Cy5 NHS ester (18.43 mg, 0.03 mmoles) dissolved in 1 ml DMF. The stirring was continued at RT for 12 h. The reaction mixture was dialyzed against DMF for 12 h, changing DMF every 4 h followed by water dialysis for 24 h. The aqueous solution was then lyophilized to afford compound 15 as blue solid in 82% yield. $^1$H NMR (500 MHz, DMSO) δ 9.41 (s, CY5 H), 8.37 (t, J=12.8 Hz, CY5 H), 7.80 (d, J=22.5 Hz, CY5H), 7.63 (t, J=7.6 Hz, CY5 H), 7.32 (d, J=8.0 Hz, CY5 H), 6.58 (t, J=12.2 Hz, CY5 H), 6.31 (d, J=13.6 Hz, CY5 H), 5.04-4.94 (m, dendrimer H), 4.70-4.56 (m, dendrimer H), 4.31-3.97 (m, dendrimer H), 3.70-3.38 (m, dendrimer H), 1.69 (s, CY5 H), 1.35-0.88 (m, CY5 & dendrimer H).HPLC purity: 100%, Retention time: 11.5 minutes Preparation of compound 17: To a stirring solution of 8-arm star PEG 10K (16) (1 g, 0.1 mmoles) in DMF (15 mL) was added BOC-GABA-OH (61 mg, 0.3 mmoles) followed by the addition of EDC (115 mg, 0.6 mmoles) and DMAP (74 mg, 0.6 mmoles). The reaction mixture was then stirred at RT for 24 h. Upon completion, the reaction mixture was dialyzed against DMF for 12 h followed by water dialysis for 12 h changing water after every 3 h. The aqueous solution was then lyophilized to yield compound 17. Yield: 70%$^1$H NMR (400 MHz, DMSO) δ 4.17-4.08 (m, PEG H), 3.62-3.45 (m, PEG H), 1.66-1.56 (m, Linker H), 1.37 (s, BOC H).

Preparation of compound 18: To a stirring solution of compound 17 (1 g, 0.1 mmoles) in dry DCM (4 mL), was added TFA (3 mL) drop wise. The reaction mixture was stirred overnight at RT. The solvent was then evaporated and the reaction mixture was diluted with methanol followed by evaporation on rotary evaporated. This process was repeated several times to remove traces of TFA. The solvent was evaporated to afford compound 18 in quantitative yield.

Preparation of compound 19: To a stirring solution of compound 18 (250 mg, 0.02 mmoles) in DMF (5 mL) was added DIPEA (0.1 ml to adjust pH to 7.4) followed by the addition of Fluorescein isothiocyanate (18 mg, 0.04 mmoles) dissolved in 1 mL DMF. The stirring was continued at RT for 12 h. The reaction mixture was dialyzed against DMF for 12 h, changing DMF every 4 h followed by water dialysis for 24 h. The aqueous solution was then lyophilized to afford compound 19 as yellow solid in quantitative yield. 1H NMR (500 MHz, DMSO) δ 6.73-6.49 (m, FITC H), 4.57 (t, J=5.5 Hz, PEG H), 4.13 (dd, J=9.3, 5.0 Hz, PEG H), 3.70-3.44 (m, PEG H), 1.82-1.68 (m, Linker H)

Results

Figure 11:
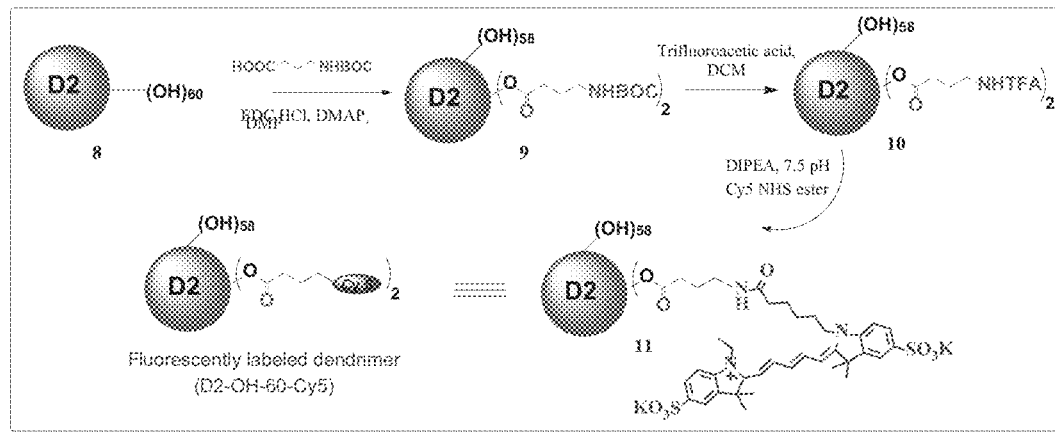
FIG. 11 Scheme 4. Synthesis of Cy5 labeled dendrimer 11.

In order to study the biodistribution using fluorescence spectroscopy and confocal microscopy, a fluorescent tag Cyanine 5 (Cy5) was conjugated to the dendrimers, D2-OH-60 (compound 8). The fluorophore was attached only on two arms of the dendrimer in order to maintain its inherent properties intact and to avoid any effect on the biodistribution. To attach the imaging dye, D2-OH-60 (compound 8) was coupled with γ-(Boc-amino)butyric acid using EDC, DMAP to obtain dendrimer 9, D-GABA-NHBOC followed by the deprotection of BOC group using trifluoroacetic acid/DCM (⅕) to get dendrimer 10 with amine groups. Dendrimer 10, having two amine groups as TFA salts, was finally reacted with Cy5 mono NHS ester at pH 7.0-7.5 to achieve Cy5 labeled dendrimer D2-OH-60-Cy5, or PEGOL-60-Cy5 (compound 11, Scheme 4 FIG. 11). $^1$H NMR clearly revealed the presence of Cy5 protons in the aromatic region upon conjugation and HPLC chromatogram showed a clear shift in retention time from 8.4 min for D-GABA-NHBOC (compound 9, 210 nm) to 7.6 min for PEGOL-60-Cy5 (compound 11, 210 and 650 nm).

Figure 12:
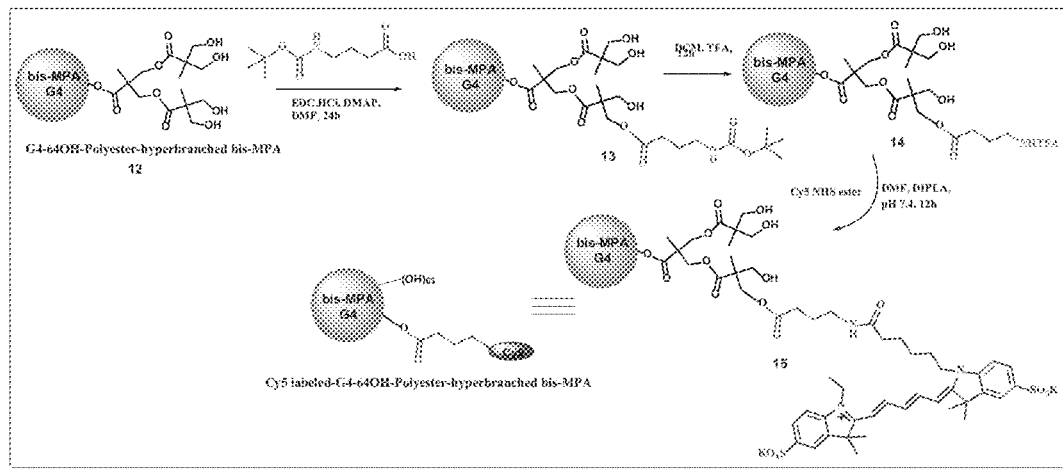
FIG. 12 Scheme 5. Synthesis of Cy5 labeled hyperbranched bis-MPA polyester 15.
Figure 13:
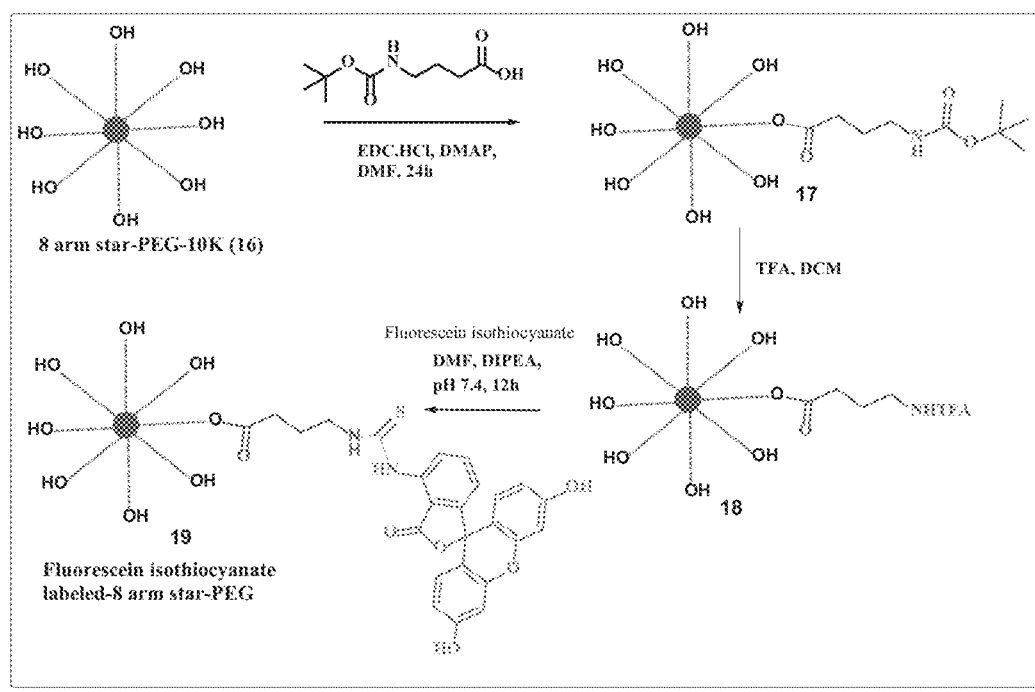
FIG. 13 Scheme 6. Synthesis of fluorescein isothiocyanate (FITC) labeled 8-arm star PEG (compound 19).

Using similar methodology, Cy5 was also attached to commercially available bis-MPA-G4-OH-64-polyester-hyperbranched polymer (compound 12, Scheme 5 FIG. 12) and G4-PAMAM-OH-64. A similar methodology was used to conjugate fluorescein isothiocyanate (FITC) to 8-arm star PEG using (Scheme 6 FIG. 13, compound 18). Linear PEG FITC and dextran FITC were used.

Example 3: Qualitative Brain Distribution of D2-OH-60-Cy5 in Brain

Methods and Materials

Rabbit Model of CP and Administration of D2-OH-60-Cy5

Time pregnant New Zealand white rabbits were purchased from Robinson Services Inc. (North Carolina, U.S.A.) and arrived at the facility one week before surgery. All animals were housed under ambient conditions (22° C., 50% relative humidity, and a 12-h light/dark cycle), and necessary precautions were undertaken throughout the study to minimize pain and stress associated with the experimental treatments. Experimental procedures were approved by the Johns Hopkins University Animal Care and Use Committee (IACUC). After one week of acclimation, the pregnant rabbits underwent laparotomy on gestational day 28 (G28) and received a total of 3,200 EU of Lipopolysaccharides (LPS, E. coli serotype 0127:B8, Sigma Aldrich, St Louis MO) injection along the wall of the uterus as previously described (Saadani-Makki, F., et al., American Journal Of Obstetrics And Gynecology, 199, 651 e1 (2008); and Kannan, S., et al., Journal of Cerebral Blood Flow and Metabolism: Official Journal Of The International Society Of Cerebral Blood Flow And Metabolism, 31, 738 (2011)). The kits were born spontaneously on G31 (full term) and kept in incubators with the temperature of ~32-35° C. and relative humidity of ~50-60%. The kits from LPS-injected dams were defined as cerebral palsy (CP) kits.

Immunohistochemistry

Animals received intravenous (i.v.) administration of D2-OH-60-cy5 (55 mg/kg, 200 µL) on PND1, and sacrificed at 24 h post-injection. The rabbits were anesthetized and transcardially perfused with PBS, followed by 10% formalin. All major organs (kidneys, lungs, liver, heart), and plasma were isolated and flash frozen. The brains were removed, and divided in to two halves. One half was flash frozen for fluorescence quantification and other half was post-fixed in 10% formalin overnight and cryoprotected in graded sucrose solutions. Coronal sections (30 µm, 1:6 series) were blocked by 3% normal donkey serum in 0.1 M phosphate-buffered saline (PBS). Sections were then incubated overnight at 4° C. with goat andti-IBA1 (1:500, Abcam, MA. U.S.A.). Sections were subsequently washed and incubated with fluorescent secondary antibodies (1:250; 1:250; Life Technologies, MA, U.S.A.) for 2 h at room temperature. Next, the sections were incubated with DAPI (1:1000, Invitrogen) for 15 min. After wash, the slides were dried and cover slipped with mountain medium (Dako, Carpinteria, CA, USA). Confocal images were acquired with Zeiss ZEN LSM 710 (Zeiss, CA, U.S.A.) and processed with ZEN software.

Results

To evaluate the in vivo distribution of D2-OH-60, D2-OH-60-Cy5 (55 mg/kg) was systematically (i.v.) injected into CP kits on postnatal day 1 (PND1). At 24 h post-injection, D2-OH-60-Cy5 distribution at different brain areas was analysed, such as the periventricular white matter area (corpus callosum, angle of lateral ventricle and internal capsule) and cortex. D2-OH-60-cy5 was widely distributed in all areas of the brain, but with higher concentration at the periventricular region, such as fornix and lateral ventricles.

To evaluate the in vivo distribution of D2-OH-60 in comparison with bis-MPA-G4-OH64, D2-OH-60-cy5 and bis-MPA-G4-OH64-cy5 (55 mg/kg) were systematically (i.v.) injected in CP kits on PND1. At 24 h post-injection, D2-OH-60-cy5 and bis-MPA-G4-OH64-cy5 distribution were analyzed at the periventricular white matter area (corpus callosum, angle of lateral ventricle and internal capsule), where most severe brain injury happened and activated glial cells accumulated in the brain of CP kits. D2-OH-60-cy5 was co-localized with activated microglia (IBA1 positive cells) in CP kits, which was similar to bis-MPA-G4-OH64-cy5. D2-OH-60-cy5 was mainly co-localized with activated microglia at the periventricular white matter areas, including corpus callosum, angle of lateral ventricle and internal capsule in CP kits. In addition, D2-OH-60-cy5 and bis-MPA-G4-OH64-cy5 distribution in cortex was also evaluated. D2-OH-60-cy5 was co-localized with ramified microglia (resting microglia) in the cortex, which is also similar to bis-MPA-G4-OH64-cy5.

Next, the in vivo distribution of D2-OH-60 was evaluated in comparison with PAMAM-G4-OH64. D2-OH-60-cy5 and PAMAM-G4-OH64-cy3 (55 mg/kg) were systematically (i.v.) injected in CP kits on PND1. At 24 h post-injection, D2-OH-60-cy5 and PAMAM-G4-OH64-cy3 distribution was analyzed at the periventricular white matter area (corpus callosum, angle of lateral ventricle). Both D2-OH-60-cy5 and PAMAM-G4-OH64-cy3 were co-localized with activated microglia in CP kits. Both D2-OH-60-cy5 and PAMAM-G4-OH64 were co-localized with activated microglia at the periventricular white matter areas, such as corpus callosum, and angle of lateral ventricle in CP kits.

The in vivo distribution of linear PEG, star PEG and Dextran was also evaluated. The linear PEG, star PEG, and Dextran (55 mg/kg) were systematically (i.v.) injected into CP kits on PND1. At 24 h post-injection, the linear PEG, star PEG, and Dextran distribution was analyzed at the periventricular white matter area (corpus callosum, angle of lateral ventricle). There was no linear PEG, star PEG, or Dextran in the periventricular region (including corpus callosum, and angle of lateral ventricle) in CP kits, indicating the linear PEG, star PEG and Dextran did not cross the blood-brain-barrier.

Example 4: Quantitative Biodistribution Comparison of D2-OH-60-Cy5, Bis-MPA-G4-OH64-Cy5, and PAMAM-G4-OH64-Cy5 in Brain and Major Organs Methods and Materials All the three dendrimer based nanoparticles (D2-OH-60-Cy5, bis-MPA-G4-OH64-Cy5, and PAMAM-G4-OH64-Cy5) were administered intravenously into postnatal day (PND) 1 cerebral palsy (CP) kits at the dose of 55 mg/kg weight of kit weight. The kits were sacrificed 4 hr and 24 hr after injection. The kits were perfused with PBS. All the major organs (Heart, lungs, liver, kidneys), and plasma were isolated and flash frozen. The brains were removed, and one half was preserved flash frozen for fluorescence quantification and other half was kept for confocal imaging as mentioned in the quantitative biodistribution section.

Figure 2:
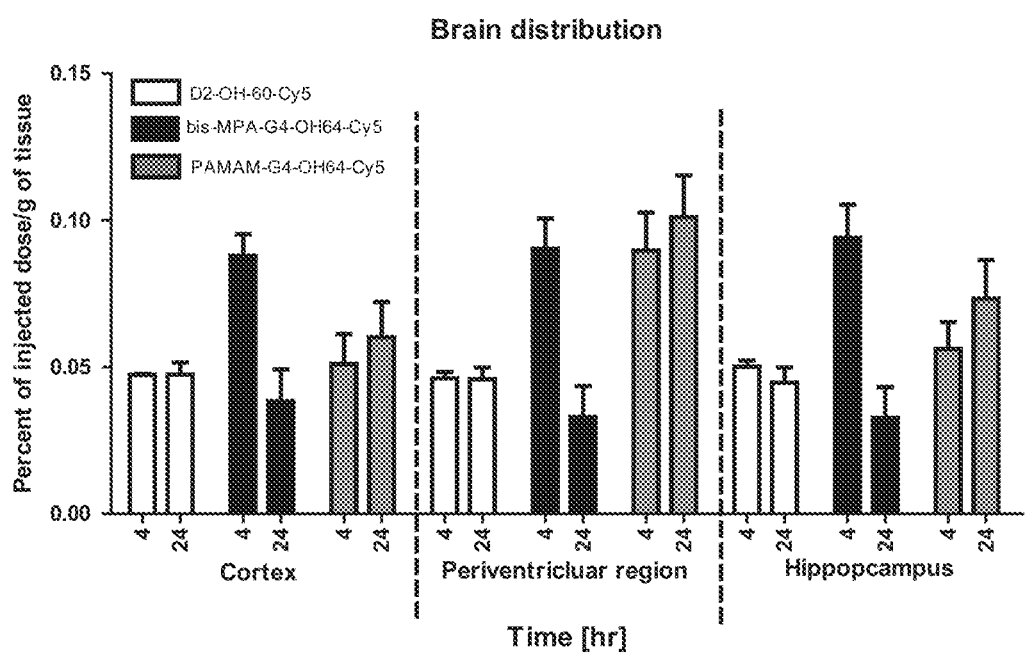
FIG. 2 is a bar graph showing comparative quantitative distribution of D2-OH-60-Cy5, bis-MPA-G4-OH64-Cy5, and PAMAM-G4-OH64-Cy5 in CP rabbit kits on postnatal day 1 in three sub-regions (cortex, periventricular region, and hippocampus) of the brain at 4 hour and 24 hour time points, measured by percent of intravenously injected dose per gram of tissue.
Figure 3:
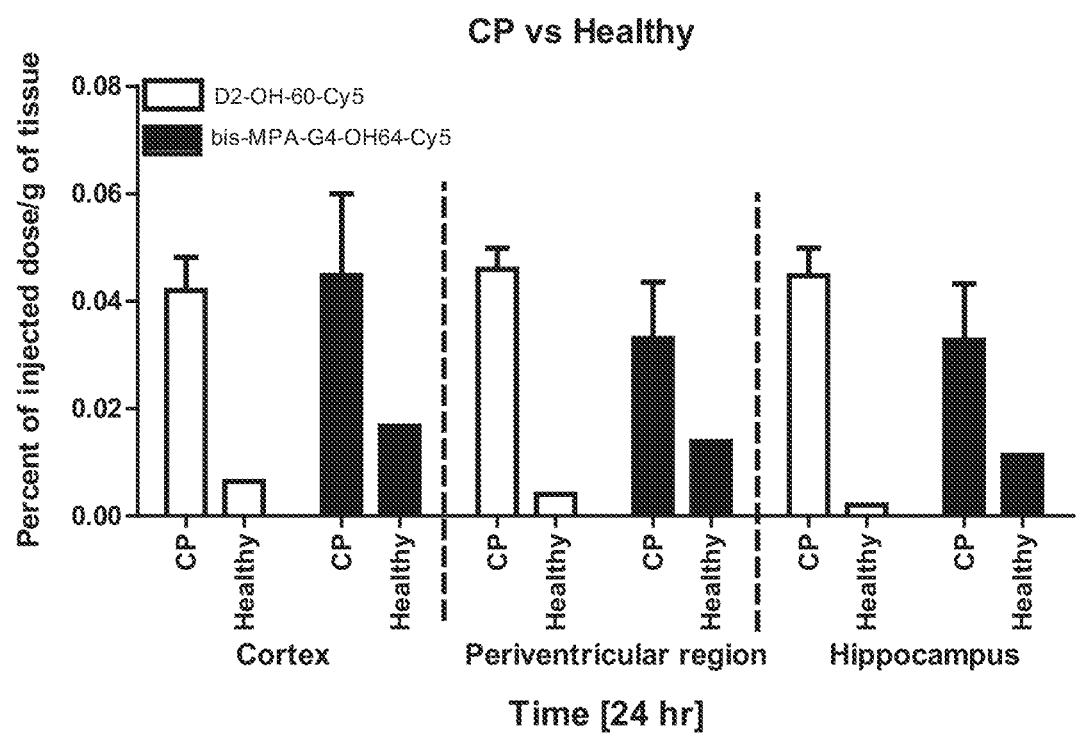
FIG. 3 is a bar graph showing comparative quantitative distribution of D2-OH-60-Cy5, bis-MPA-G4-OH64-Cy5, and PAMAM-G4-OH64-Cy5 on postnatal day 1 in CP rabbit kits versus healthy rabbit kits in three sub-regions (cortex, periventricular region, and hippocampus) of the brain at 24 hour time points, measured by percent of intravenously injected dose per gram of tissue.
Figure 4:
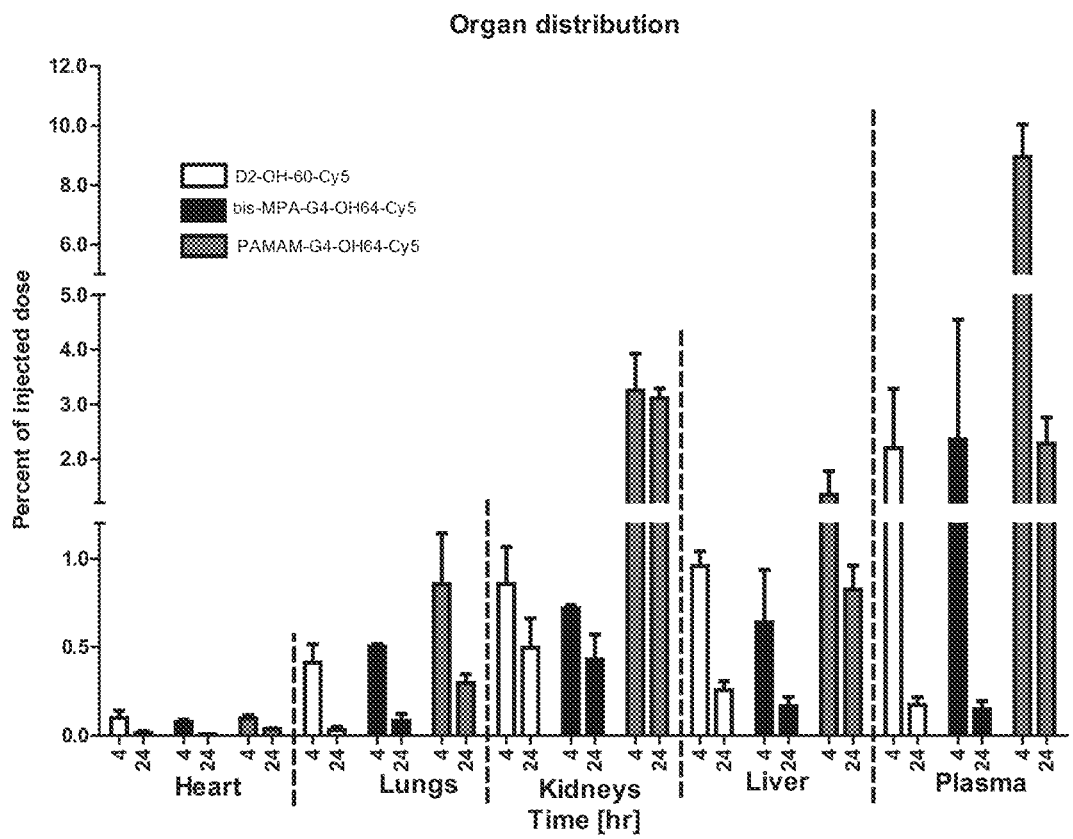
FIG. 4 is a bar graph showing comparative quantitative distribution of D2-OH-60-Cy5, bis-MPA-G4-OH64-Cy5, and PAMAM-G4-OH64-Cy5 in major organs (heart, lungs, kidneys, and liver) and plasma of CP rabbit kits on postnatal day 1 in three sub-regions (cortex, periventricular region, and hippocampus) of the brain at 4 hour and 24 hour time points, measured by percent of intravenously injected dose per gram of tissue.

In order to evaluate the dendrimer distribution and quantification within the brain by fluorescence spectroscopy, the brains were further micro-dissected in to three sub-regions, cortex, periventricular region (PVR) and hippocampus. FIG. 2 shows the comparative brain distribution in these three sub-regions for D2-OH-60-Cy5 and commercially available bis-MPA-G4-OH64-Cy5, and PAMAM-G4-OH64-Cy5. All the three dendrimers having high density of surface hydroxyl groups could cross the impaired blood brain barrier (BBB) and were present in cortex, PVR and hippocampus in similar quantities. Although bis-MPA seemed to be present more at 4 hr time-point, but did not show any difference at 24 hr. Unlike PAMAM which shows more accumulation in PVR region, D2-OH-60-Cy5 and bis-MPA-G4-OH64-Cy5 showed similar distribution in all the three sub-regions. Both D2-OH-60-Cy5 and bis-MPA-G4-OH64-Cy5 showed several folds higher uptake in cortex, PVR and hippocampus of PND1 CP kits as compared to healthy controls (FIG. 3). The distribution in all other major organs (heart, lungs, liver) was similar for all the three dendrimers, except in the kidneys and plasma. The amounts of D2-OH-60-Cy5 and bis-MPA-G4-OH64-Cy5 in kidneys and plasma were far less at both 4 hr and 24 hr time-points as compared to PAMAM-G4-OH64-Cy5 indicating their shorter circulation time and faster renal clearance (FIG. 4).

Example 5: Qualitative Distribution of PEGOL-60-Cy5 in the Eye

Methods and Materials

Rat Lipid Injected AMD Model and Administration of PEGOL-60-Cy5

Sprague Dawley (SD) rats, 8 weeks of age were selected for this experimental AMD model. The studies were done in accordance to ARVO guideline and Johns Hopkins approved animal protocols. The rats were housed under ambient conditions (22° C., 50% relative humidity and a 12-h light/dark cycle). On day 0, 2 µL of HpODE (lipid) in 0.5M borate buffer (20 µg/mL), was sub-retinally injected using a microinjector to form blebs underneath the retina. To evaluate the ocular biodistribution of, D2-OH-60-Cy5 on day 3 after lipid injection, D2-OH-60-Cy5 was formulated in sterile saline (200 µL) and was administered intravenously at a concentration of 20 mg/Kg. The rats were sacrificed 48 hrs and 7 days post dendrimer administration. At appropriate time points, after euthanasia, the eye balls were enucleated and subjected for flat-mount and cross section analysis.

Tissue Processing, Immunohistochemistry and Confocal Imaging

Flat-mounts: The eye balls were incubated in PBS in ice for 1 hr and the anterior segment including lens were removed. Retina and choroids were separated and fixed in 2% PFA for 12 hrs followed by blocking with goat serum for 6 hrs. The microglia/macrophages were stained using anti rabbit Iba-1 for 12 hrs at 4° C. and secondary with Cy3 labelled goat anti rabbit antibody. FITC labelled lectin was used to label and stain blood vessels and monocytes. The flat-mounts were prepared using 4 radial relaxation cuts and mounted on coverslip and imaged under confocal 710 microscope using tile, Z-stack function. The images were processed using Zeiss software.

Cross sections: The eye balls were fixed in 2% PFA with 5% sucrose for 3 hrs and the anterior segments including lens were removed and the posterior segments were subjected to sucrose gradient treatment until 20%. The tissues were cryopreserved using OCT and sectioned (10 µm sections) along the optic nerve. The sections were blocked with goat serum and stained using Iba-1 for microglia/macrophages, lectin for blood vessels and monocytes and DAPI for nucleus. The stained sections were imaged under a confocal 710 microscope.

Results

In addition to brain penetration, PEGOL-60-Cy5 co-localization with activated mi/ma in a subretinal lipid injection-induced model of age related macular degeneration (AMD) was also examined to determine its ability to cross the blood-retina barrier for applications in diseases of the back of the eye (Baba T, The American Journal of Pathology 2010, 176, 3085).

AMD is a multifactorial ocular degenerative disease that involves multiple activated mi/ma-mediated pathologies including oxidative stress, inflammation, and neovascularization (Madeira M H, Mediators of Inflammation 2015, 2015, 15). Pathological buildup of toxic lipids leads to vision loss in patients, and currently there are no viable therapies available for dry and early AMD.

The targeting capabilities of PEGOL-60-Cy5 were tested in a rat model of dry AMD produced with a subretinal injection of lipid to induce cell damage, resulting in a region of neovascularization referred to as a bleb. Confocal imaging of choroidal flatmounts show PEGOL-60-Cy5 signal localized with activated mi/ma specifically in the bleb area after systemic administration with minimal signal in healthy tissues Both flat-mounts and cross sections demonstrate that PEGOL-60-Cy5 dendrimer targets and gets retained in the areas of inflammation both in retina and choroidal tissue. In retinal tissue, PEGOL-60-Cy5 was found localized in microglial cells that accumulated in the vicinity of the radial blood vessels and the capillaries at the bleb borders. The blood vessels were stained with lectin, microglia/macrophages with Iba-1, dendrimer (PEGOL-60-Cy5) labelled using Cy5, and nucleus with DAPI. 5× magnification demonstrates that intravenously administered dendrimers were found localized only in areas of inflammation. Higher magnification images (40×) demonstrates that PEGOL-60-Cy5 was found co-localized in activated microglia/macrophages near the leaky blood vessels in the bleb areas of the retina. High magnification images clearly demonstrate PEGOL-60-Cy5 co-localization in the retinal microglia pertaining to the injured area, thus confirming the targeted localization.

In the choroidal tissues, the dendrimer was only found in activated macrophages and hypertrophic retinal pigment epithelium (RPE) in the injured area corresponding to that of bleb area in the choroid. Choroidal tissues were stained for lectin (Blood vessels), microglia/macrophages with Iba-1 and dendrimer (D2-OH-60-Cy5). 20×image shows dendrimers were found the bleb area and higher magnification image (40×image) confirms that dendrimers are co-localized in activated macrophages and in hypertrophic retinal pigment epithelium (RPE) in the bleb areas.

Cross section analysis of the posterior segment (retina+choroid complex) was carried out for detailed biodistribution. The sections revealed that, in retina, dendrimer are co-localized in activated microglia, Müller glia (based on location) and monocytes. Ten microns sections of the posterior segment of the rat's eye were stained for lectin (Blood vessels), microglia/macrophages (Iba-1), nucleus (DAPI) and dendrimer (PEGOL-60-Cy5) labelled using Cy5. 5×image revealed the whole posterior section with bleb area with characteristics of inflammation (accumulated cells labeled positive for Iba-1). Higher magnification 20×images demonstrate that the dendrimers are co-localized only in the areas of inflammation in activated microglia/macrophages in choroid and retina and Müller cells in the retina. Thus, cross sections corroborate these findings, showing PEGOL-60 localized within activated mi/ma and CNV blood vessels in retina and choroid in the bleb area and not in healthy regions of the eye In summary, PEGOL-60 demonstrates pathology-dependent biodistribution in the retina and choroid in rat AMD model upon systemic administration. These results suggests PEGOL-60 is a promising drug carrier for systemic targeted therapies in AMD where there are few viable therapeutic interventions available, as well as other posterior segment ocular diseases such as diabetic retinopathy, retinopathy of prematurity, retinitis pigmentosa, and uveitis (M. Karlstetter, et al., Progress in Retinal and Eye Research, 45, 30 (2015)).

Example 6: PEGOL-60-Cy5 Targeting of Tumor Associated Macrophages in a Mouse Model of Glioblastoma (GBM)

Methods and Materials

Mouse Model of GBM and Administration of PEGOL-60-Cy5

C57BL/6 mice 6-8 weeks old were purchased from Jackson Laboratories (Bar Harbor, ME, USA), and experimental procedures were under ACUC approved protocol. GL261 murine GBM tumor cells were grown in low glutamine RPMI (Gibco Laboratories; Gaithersburg, MD) supplemented with 10% heat inactivated FBS (Gibco Laboratories), 1% pen/strep antibiotic (Gibco Laboratories), and 1% 1-glutamine (Gibco Laboratories) in an incubator at 37° C. and 5% $CO_2$. Cells were collected via trypsin detachment (Corning Inc; Corning, NY) for inoculation. Mice were anesthetized with IP injection of a cocktail of 100 mg/kg ketamine (Henry Schein; Melville, NY) and 10 mg/kg xylazine (VetOne; Boise, Idaho) in normal saline (Quality Biological Inc.; Gaithersburg, MD). An incision was made along the midline of the skull, and a burr hole was drilled for Hamilton syringe (Hamilton Company; Reno, NV) insertion. 100,000 GL261 cells in 2 μL media were injected into the right hemisphere striatum at a rate of 0.2 μL/min via a stereotaxic frame and automatic syringe pump (Stoelting Co.; Wood Dale, IL). Mice were then sutured (Ethicon Inc.; Somerville, NJ) and monitored for surgical recovery. For administration of PEGOL-60-Cy5, mice were intravenously injected with 55 mg/kg PEGOL-60-Cy5 15 days post-inoculation. Mice were perfused and brains collected 24 hrs after administration.

Immunohistochemistry and Confocal Imaging for GBM Model

Animals were intravenously administered on day 14 post tumor inoculation with 55 mg/kg PEGOL-60-Cy5 and brains collected 24 hrs later. Brains were fixed in 10% formalin (Sigma-Aldrich) for 24 hrs, followed by sucrose gradient from 10% to 30% for 24 hrs each. Brains were then frozen and sectioned coronally into 30 μm slices. Brains slices were blocked in 1× TBS (Gibco Laboratories) supplemented with 0.1% Triton-X (Sigma-Aldrich), 1% bovine serum albumin (Sigma-Aldrich), and 5% normal goat serum (Sigma-Aldrich) for 4 hrs at room temperature. Microglia were labeled with tomato lectin (1:1000, Vector Labs; Burlingame, CA) and cell nuclei with NucBlue DAPI cell stain (Invitrogen). Slides were then cover-slipped with mounting media (Dako). Confocal images were acquired on a Zeiss ZEN LSM710 (Zeiss) and processed with ZenLite software.

Results

PEGOL-60 was further evaluated in a murine model of GBM to assess whether this specific co-localization with activated mi/ma in pro-inflammatory diseases extends to targeting anti-inflammatory M2-phenotype mi/ma as well, and whether it could uniformly distribute throughout the solid tumor. These targets tumor-associated macrophages (TAMs) are host macrophages that have an induced anti-inflammatory phenotype to promote tumor growth and suppress the tumor killing immune response by secretory signals from cancer cells, making them ideal therapeutic targets for immune modulating agents to repolarize into cancer-fighting cells (Yang Y et al., Hematol Oncol 2017, 10, 58).

Despite the discovery of many powerful new anti-cancer therapies, clinical outcomes have not translated to GBM because these treatments fail to penetrate through the BBB and into the solid brain tumor in clinically relevant quantities, thereby necessitating high doses that lead to systemic toxicity. We explored the tumor targeting ability of PEGOL-60-Cy5 in the GL261 intracranial injection mouse model of GBM, which has been extensively characterized and is known to closely recapitulate the immune profile of human (Jacobs V L et al., ASN Neuro 2011, 3, AN20110014).

GL261 murine GBM cells were inoculated into the striatum of mice, and PEGOL-60-Cy5 was intravenously administered 15 days post-inoculation. PEGOL-60-Cy5 selectively targets tumor-associated macrophages (TAMs) upon systemic administration. Brains were collected 24 hours post administration and confocal images for dendrimer (Cy5), cell nuclei (DAPI), and TAMs (lectin) were collected and examined. PEGOL-60 co-localizes with TAMs in the tumor, while minimal dendrimer signal is exhibited in the healthy brain tissue of the contralateral hemisphere. The confocal images also demonstrate that PEGOL-60 fully penetrates to the tumor center and uniformly distributes among TAMs throughout the tumor. Dendrimer uptake clearly delineates the tumor border, with dendrimer signal in TAMs within the tumor and minimal signal seen in the peritumoral regions.

In summary, it has been demonstrated that PEGOL-60-Cy5 specifically targets TAMs within the solid tumor upon systemic administration while exhibiting minimal signal in the contralateral hemisphere. The dendrimer is able to fully penetrate and distribute throughout the solid tumor, overcoming both the BBB and traditional barriers to solid tumor delivery such as poorly developed vasculature and high interstitial fluid pressure. The signal of PEGOL-60-Cy5 clearly delineates the tumor region, demonstrating its specificity for TAMs over mi/ma in healthy parts of the brain, even in the peritumor area. These findings suggest that PEGOL-60 provides an ideal nanoplatform with which to specifically and systemically deliver immunotherapies to the solid tumor in GBM without damaging healthy brain tissue.

Example 7: In Vitro Evaluation of Anti-Oxidant and Anti-Inflammatory Activity of PEGOL-60

Methods and Materials
Cell Culture

BV2 murine microglia were obtained from the Children's Hospital of Michigan's cell culture facility. Cells were cultured in an incubator at 37° C. and 5% $CO_2$ in DMEM (Gibco Laboratories) supplemented with 10% heat inactivated fetal bovine serum and 1% pen/strep. Cells were maintained via trypsin detachment and passage every 3 days. At 80-90% confluence, cells were collected and seeded in 24-well plates for experiments.

Cytotoxicity Evaluation

BV-2 murine microglia cell line were cultured as described in experimental section and seeded in alternating wells of 96-well plates (Sigma) at a concentration of 10,000 cells per well. Cells were then allowed to adhere and grow for 24 hrs. A stock solution of 1000 μg/mL PEGOL-60 was made in DMEM medium supplemented with 10% HI-FBS and 1% penicillin-streptomycin, vortexed, sonicated, and sterile filtered. This solution was then diluted in medium to make stocks of 100, 10, 1, and 0.1 μg/mL PEGOL-60. Medium was aspirated off all wells of the 96-well plate, and either medium containing PEGOL-60 or fresh medium was replaced on the cells, which were allowed to culture for an additional 24 hrs. A 12 mM stock solution of MTT (Invitrogen, Carlsbad, CA) in sterile PBS was made and mixed by vortex and sonication. Medium was removed from all wells, and 100 μL of fresh medium was added to each well as in addition to 10 μL of MTT solution, which was mixed with the medium by pipetting. The cells were then allowed to incubate in the MTT for four hrs after which 85 μL of the MTT medium was removed and replaced with 150 μL of DMSO (Corning) as mixed thoroughly by pipetting. The DMSO incubated with the cells at 37° C. for 10 minutes, after which the wells were mixed by pipetting again before the absorbance at X=540 nm of each well was read on a Synergy Mx Microplate Reader (BioTek, Winooski, VT) running Gen5 software (BioTek). The absorbances were all converted to ratios compared to untreated cells after subtracting off the background of media controls. Three plates were used and treatments were done in triplicate on each plate and averaged to produce one data point.

LPS Stimulation and Evaluation

BV2 murine microglia were seeded in 24-well plates. Cells were stimulated with 100 ng/ml LPS (Sigma-Aldrich) for 3 hrs in serum free media, followed by coincubation with PEGOL-60 and 100 ng/ml LPS for 24 hrs. PEGOL-60 was solubilized in media and syringed filtered through 20 μm pore filters. Media was collected and analyzed for nitrite production via Griess reaction (Promega Corporation; Madison, WI) and TNFα secretion via ELISA (Biolegend; San Diego, CA).

Cells were collected in 1 mL Trizol (Invitrogen) for PCR analysis. Briefly, 200 μL of chloroform (ThermoFisher) was added, and samples were shaken and incubated on ice for 15 minutes. Samples were then centrifuged for 15 minutes at 12000 rpm and aqueous fraction was collected. 500 μL isopropanol (ThermoFisher) was added to each sample, mixed, and incubated on ice for 10 minutes. Samples were again centrifuged for 15 minutes at 12000 rpm and washed with 75% ethanol in DEPC water (Invitrogen). Samples were nanodropped (ThermoFisher) to determine RNA concentration and converted to cDNA (Applied Biosystems; Foster City, CA). Samples were measured on StepOne Plus real time PCR system (Applied Biosystems) with green syber reagent (ThermoFisher) on fast PCR plates (ThermoFisher). Relative expression was determined via 2 delta CT calculations normalized to the untreated, unstimulated control samples. PCR primers for IL10, iNOS, and CD204 were obtained from Biorad (Bio-Rad Laboratories; Hercules, CA). PCR primers for TNFα (F: CCA GTG TGG GAA GCT GTC TT (SEQ ID NO:1); R: AAG CAA AAG AGG AGG CAA CA (SEQ ID NO:2), IL6 (F: TCC AGT TGC CTT CTT GGG AC (SEQ ID NO:3); R: GTG TAA TTA AGC CTC CGA CTT G (SEQ ID NO:4)), Arg1 (F: TCA TGG AAG TGA ACC CAA CTC TTG (SEQ ID NO:5); R: TCA GTC CCT GGC TTA TGG TTA CC (SEQ ID NO:6)), IL4 (F: TGT AGG GCT TCC AAG GT (SEQ ID NO:7); R: GAA AGA GTC TCT GCA GCT C (SEQ ID NO:8)), and GAPDH (F: TGT CGT GGA GTC TAC TGG TGT CTT C (SEQ ID NO:9); R: CGT GGT TCA CAC CCA TCA CAA (SEQ ID NO:10)) were purchased from Integrated DNA Technologies (Integrated DNA Technologies; Coralville, IA).

Oxidative Stress Induced Cell Death

BV2 murine microglia were pretreated with D2-OH-60 for 24 hrs, followed by oxidative stress insult with 500 μM $H_2O_2$ (Sigma-Aldrich) for 3 hrs. Cells were collected via trypsinization, mixed 1:1 with trypan blue (Corning), and counted for cell viability.

Results

Figure 5:
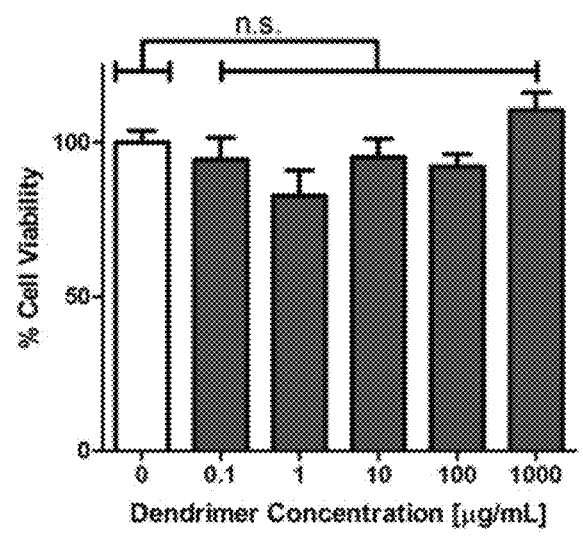
FIG. 5 is a bar graph showing MTT cell viability assay results in BV-2 cells treated with increasing concentrations of PEGOL-60 for 24 hrs. n=3.

The inherent anti-oxidant and anti-inflammatory efficacy of PEGOL-60 was investigated (Posadas I et al., Proceedings of the National Academy of Sciences 2017, 114, E7660; Chauhan A S et al., Biomacromolecules 2009, 10, 1195). First, PEGOL-60 was not found to be cytotoxic up to at least 1000 μg/mL after 24 hrs of exposure via MTT assay (FIG. 5; n=3, p<0.05).

Figure 6A:
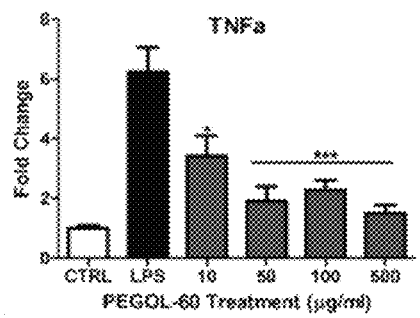
FIGS. 6A-6J are bar graphs showing PEGOL-60 alone (i.e., no drug) displays anti-inflammatory and anti-oxidant properties in vitro: BV2 murine microglia were stimulated with 100 ng/ml LPS for 3 hours, followed by co-treatment with dendrimer for 24 hours.
Figure 6B:
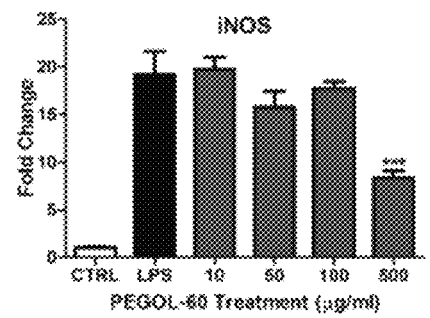
Figure 6C:
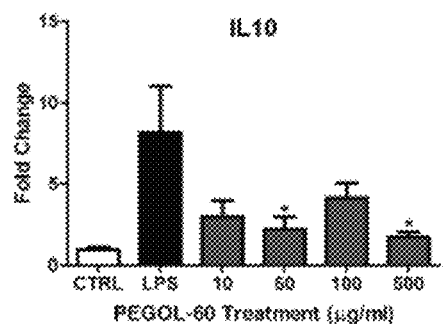
Figure 6D:
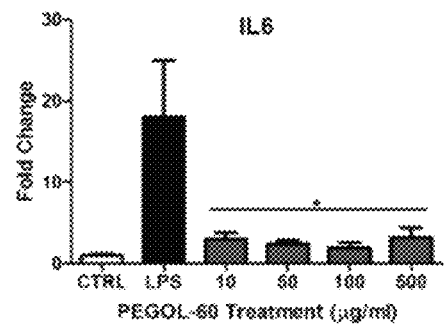
Figure 6E:
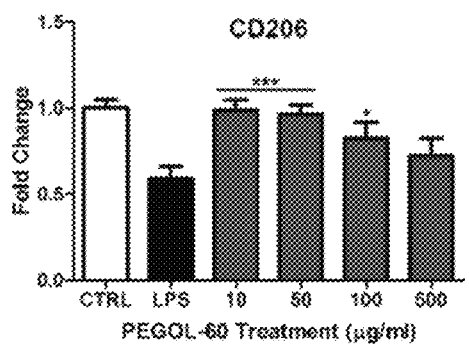
Figure 6F:
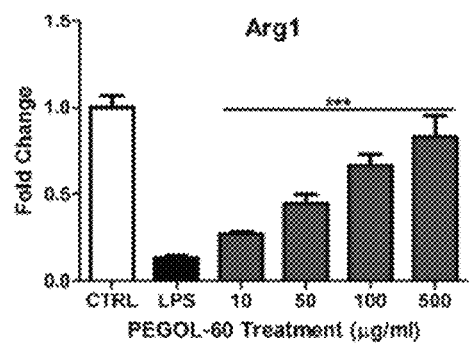
Figure 6G:
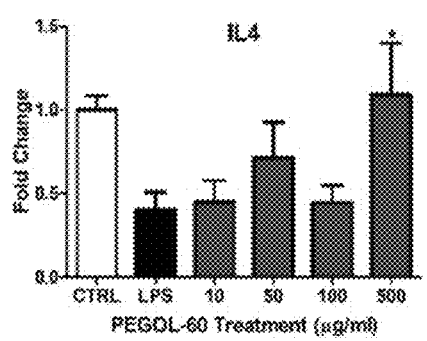
Figure 6H:
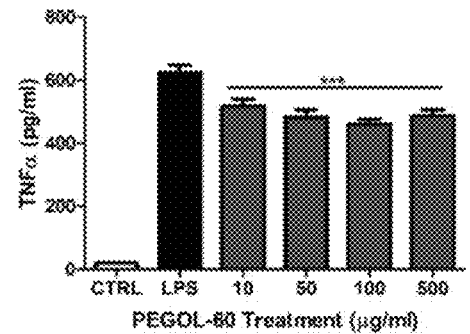
Figure 6I:
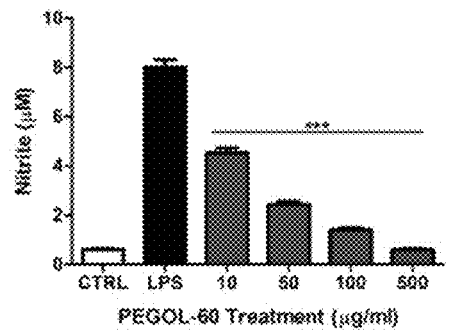

To assess the therapeutic efficacy of PEGOL-60, BV2 murine microglia were challenged with LPS to induce a pro-inflammatory state, then co-treated with LPS and PEGOL-60 and assessed for markers of inflammation and oxidative stress. Treatment with PEGOL-60 without the addition of any anti-oxidant or anti-inflammatory agents resulted in significantly decreased the expression of pro-inflammatory cytokines including TNF-α, IL-6, IL-10, and iNOS (FIGS. 6A-6D), as well as upregulation of anti-inflammatory markers CD-206, Arg-1, and IL-4 (FIGS. 6E-6G), in generally dose-dependent manners. Both pro- and anti-inflammatory markers were restored to near healthy levels with high 500 μg/ml PEGOL-60 treatment. At the protein level, this resulted in significant reduction in extracellular secreted TNFα (FIG. 6H; p<0.001) and nitrite ions (FIG. 6I; p<0.001).

Figure 6J:
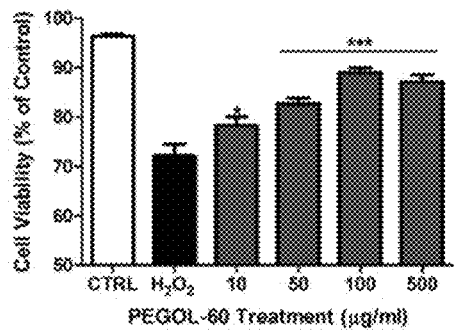

Based on this powerful anti-oxidant effect, the efficacy of PEGOL-60 following oxidative stress insult was also assessed. Pretreatment with PEGOL-60 resulted in significant improvement to cell viability after $H_2O_2$ challenge (FIG. 6J; p<0.001). This anti-oxidant effect is consistent with results seen both in vitro and in vivo with several other dendrimer constructs absent therapeutic payloads (Neibert K et al., Molecular Pharmaceutics 2013, 10, 2502; Posadas I et al., Proceedings of the National Academy of Sciences 2017, 114, E7660; Chauhan A S et al., Biomacromolecules 2009, 10, 1195). This anti-oxidant effect is likely due to the free electrons in the dendrimer backbone acting as scavengers to neutralize reactive oxygen species (ROS). Access of these scavengers in the backbone to (ROS) may be sterically inhibited by the branching arms, with each successive generational layer further shielding the interior. PEGOL-60 has the desired properties as a superior nanocarrier because it achieves the high density of hydroxyl groups at relatively lower generation, allowing for accessibility of the backbone for ROS scavenging.

Example 8: In Vivo Efficacy and Safety Profile of the PEGOL-60

Methods and Materials

In vivo administration of PEGOL-60

On PND1, the littermates in CP groups were randomly divided into 3 subgroups: PBS, PEGOL-60 single dose and PEGOL-60 re-dose groups. Rabbits in PEGOL-60 single dose group received a single dose of PEGOL-60 (100 mg/kg, 200 μL) intravenous injection on PND1. Rabbits in PEGOL-60 re-dose group received PEGOL-60 (100 mg/kg, 200 μL) intravenous injection on PND1 and PND3. Rabbits in PBS group received a single dose of PBS (200 μL) intravenous injection on PND1. All solutions used for administration were sterilized using 0.2 um Acrodisc© syringe filters (Pall Corporation, Port Washington, NY) prior to injection.

Behavioral Testing

The animals' (n=6) general physical conditions (e.g. weight gain, food intake, etc.) were monitored daily. Neurobehavioral tests were carried out on PND1 before drug administration (baseline, 0 h), as well as 24, 48 and 96 hrs post drug administration by personnel blinded to the experiments. Each animal was videotaped for 10 min and scored on a scale of 0-3 (0=worst; 3=best) for head movement as previously described for rabbits (E. Nance, et al., Biomaterials, 101, 96 (2016); Z. Zhang, et al., Neurobiology of Disease, 94, 116 (2016)). The kits were fed with Wombaroo rabbit milk replacer (Perfect Pets Inc, Belleville, MI) and the suck/swallow were assessed on a scale of 0-3 (worst-best) (J. Yang, et al., Chemical Reviews, 115, 5274 (2015)). To minimize the impacts of disease phenotype variability, the changes in the behavioral scores before (0 h) and 24, 48 and 96 hrs. post-treatment for each kit were used to evaluate the efficacy of therapies. In details, the behavioral scores of each kit on PND1 before treatment (0 h) were used as the baseline scores. The changes in the neurobehavioral scores at 24, 48 and 96 hrs. post-treatment for each kit were calculated as:

$$\text{Changes from baseline}_{(48)} = \text{Score}_{(48h)} - \text{Score}_{(0\ h)} \text{ or}$$
$$\text{Changes from baseline}_{(96)} = \text{Score}_{(96h)} - \text{Score}_{(0\ h)}$$

The changes of all the kits in each group were averaged and compared among groups.

Real-Time PCR

On PND5, kits (n=3) from all the groups were euthanized. The brains were quickly harvested and stored in RNAlater solution (Life technologies, Grand Island, NY, USA). The periventricular region (PVR) white matters and cerebellar white matter areas were micro-dissected (~50 mg). The total RNA was extracted using TRIZOL (Life Technologies, Grand Island, NY, USA) according to the manufacturer instructions. RNA samples were quantified using the Nano-drop ND-1000 Spectrophotometer (Thermo Fisher Scientific, Walkersville, MD). The single-stranded complementary DNA (cDNA) was first reverse transcribed from the total RNA samples using the High Capacity cDNA Reverse Transcription Kit with RNase inhibitor (Life Technologies, Grand Island, NY, USA). The real-time PCR was performed with Power SYBR® Green PCR Master Mix (Life Technology, Grand Island, NY, USA) using Fast 7500 Real-time PCR systems (Life Technologies, Grand Island, NY, USA). Amplification conditions included 30 min at 48° C., 10 min at 95° C., 40 cycles at 95° C. for 15 s and 60° C. for 1 min. Primers were custom-designed and ordered from Integrated DNA Technology (Iowa, USA). Comparative Ct method was used to assess differential gene expressions. The gene expression levels for each sample were normalized to the expression level of the housekeeping gene encoding Glyceraldehydes 3-phosphate dehydrogenase (GAPDH) within a given sample (ΔCt); the differences between the treatment groups to the healthy control group were used to determine the ΔΔCt. The $2^{-\Delta\Delta Ct}$ gave the relative fold changes in gene expression. The primers were:

```
                                    (SEQ ID NO: 11)
TNF-α (forward)      TAGTAGCAAACCCGCAAGTG;

(SEQ ID NO: 12)
TNF-α (reverse)      CTGAAGAGAACCTGGGAGTAGA.

(SEQ ID NO: 13)
IL-1β (forward)      TGCCAACCCTACAACAAGAG;

(SEQ ID NO: 14)
IL-1β (reverse)      AAAGTTCTCAGGCCGTCATC.

(SEQ ID NO: 15)
IL-6 (forward)       CATCAAGGAGCTGAGGAAAGAG;

(SEQ ID NO: 16)
IL-6 (reverse)       CCTTGGAAGGTGCAGATTGA.

(SEQ ID NO: 17)
GAPDH (forward)      TGACGACATCAA GAA GGTGGTG;

(SEQ ID NO: 18)
GAPDH (reverse)      GAAGGTGGAGGAGTGGGTGTC.
```

Results

Figure 7A:
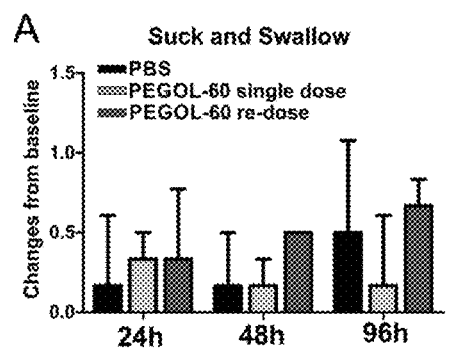
FIGS. 7A-7F are bar graphs showing in vivo efficacy of PEGOL-60 in CP model in which littermates of CP kits were randomly divided into PBS, PEGOL-60 single dose and PEGOL-60 re-dose groups on PND1, and received PBS (PND1), PEGOL-60 (PND1) or PEGOL-60 (PND1 and PND3), respectively. Neurobehavioral tests were carried out at before treatment (baseline, 0 h) and 24, 48 and 96 hrs post-treatment (n=6) including suck and swallow (FIG. 7A), head movement (FIG. 7B) and body weight gain (FIG. 7C) among the groups at 24, 48 and 96 h post-treatment. Pro-inflammatory cytokines were measured at PND5 (n=3) including TNF-α (FIG. 7D), IL-1β (FIG. 7E) and IL-6 (FIG. 7F) among groups.
Figure 7B:
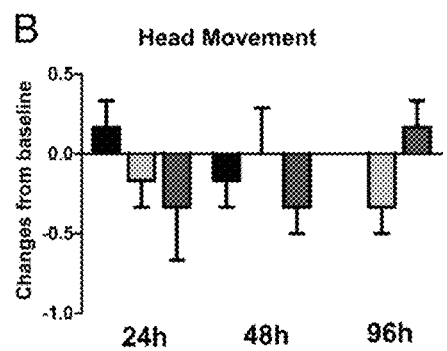
Figure 7C:
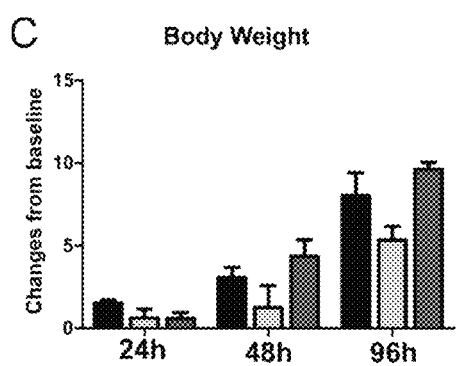
Figure 7D:
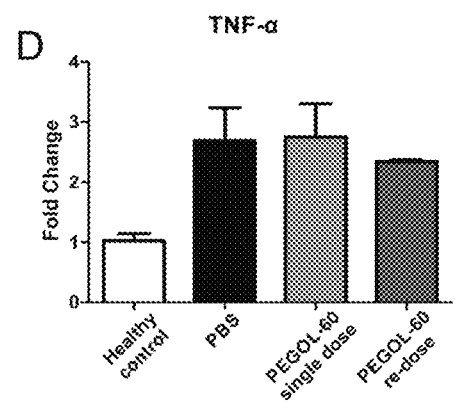
Figure 7E:
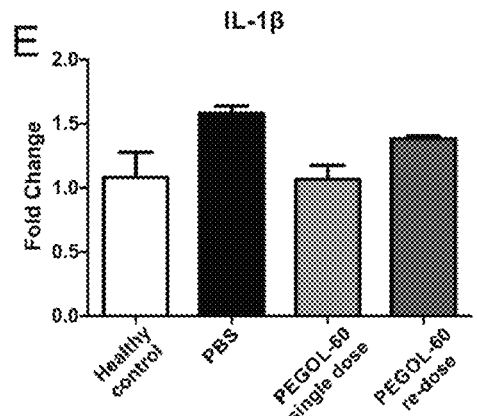
Figure 7F:
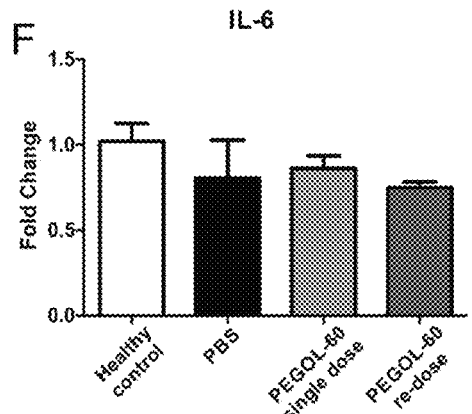

On postnatal day (PND)1, CP littermates were randomly divided into 3 subgroups: PBS, PEGOL-60 single dose, and PEGOL-60 re-dose groups. Rabbits in the PEGOL-60 single dose group received a single dose of PEGOL-60 at 100 mg/kg in 200 μL of sterile PBS via intravenous injection on PNDL. Rabbits in the PEGOL-60 re-dose group received PEGOL-60 at 100 mg/kg in 200 μL of sterile PBS via intravenous injection on PND1 and PND3. Rabbits in the PBS group received a single dose of PBS (200 µL) via intravenous injection on PND1. The general condition, neurobehavior, and body weight of the rabbit kits were monitored daily. It was noted that there was no significant difference in suck and swallow, head movement, and body weight gain among the groups (FIGS. 7A-C). Moreover, there was no significant change in the cytokine expression among the groups (FIGS. 7D-F). These results indicate that PEGOL-60 did not further impair neurobehavioral scoring in CP kits, suggesting PEGOL-60 is a non-toxic carrier for use in vivo.

Example 9: Qualitative Brain Distribution of PEGOL-60-Cy5 Biodistribution in a Neonatal Rabbit Model of Cerebral Palsy (CP)

Methods and Materials

Rabbit Model of CP and Administration of PEGOL-60-Cy5

New Zealand white rabbits were purchased from Robinson Services Inc. (NC, U.S.A.) and arrived at the facility two weeks before breeding. All animals were housed under ambient conditions (22° C., 50% relative humidity, and a 12-h light/dark cycle), and necessary precautions were undertaken throughout the study to minimize pain and stress associated with the experimental treatments. Experimental procedures were approved by the Johns Hopkins University Animal Care and Use Committee (IACUC). Timed-pregnant rabbits underwent laparotomy on gestational day 28 (G28) and received a total of 3,200 EU of lipopolysaccharides (LPS, *E. coli* serotype 0127:B8, Sigma Aldrich, St Louis MO) injection along the wall of the uterus as previously described (F. Saadani-Makki, et al., American journal of obstetrics and gynecology, 199, 651.e1 (2008); S. Kannan, et al., Developmental Neuroscience, 33, 231 (2011); S. Kannan, et al., Dev Neurosci-Basel, 33 (2011)). Rabbits were induced on G30 with intravenous injection of Pitocin® (0.5 unit/kg) (JHP Pharmaceuticals; Rochester, MI). After delivery, rabbit kits were kept in incubators with the temperature of ~32-35° C. and relative humidity of ~50-60% and fed with rabbit milk replacer (Wombaroo; South Australia, Australia) three times per day. On postnatal day 1 (PND1), healthy controls and CP kits received a single dose of PEGOL-60-Cy5 (55 mg/kg, 200 µL) via intravenous injection. CP kits were sacrificed at 1, 4 and 24 hrs post-injection. Healthy controls were sacrificed at 24 hrs post-injection. All solutions used for administration were sterilized using 0.2 um Acrodisc® syringe filters (Pall Corporation, Port Washington, NY) prior to injection.

Immunohistochemistry for CP Model

Animals received intravenous (i.v.) administration of PEGOL-Cy5 (55 mg/kg, 200 µL) on PND1, and sacrificed at 24 h post-injection. The rabbits were anesthetized and transcardially perfused with PBS. All major organs (kidneys, lungs, liver, heart), and plasma were isolated and flash frozen. The brains were removed, and divided in to two halves. One half was flash frozen for fluorescence quantification and the other half was post-fixed in 10% formalin for 48h and cryoprotected in graded sucrose solutions. Coronal sections (30 µm, 1:6 series) were blocked by 3% normal donkey serum in 0.1 M phosphate-buffered saline (PBS). For PEGOL-60-Cy5 and microglia co-localization, sections were incubated with goat andti-IBA1 (1:250, Abcam, MA. U.S.A.) overnight at 4° C. Sections were subsequently washed and incubated with fluorescent secondary antibodies (1:250; Life Technologies, MA, U.S.A.) for 2 h at room temperature. Next, the sections were incubated with DAPI (1:1000, Invitrogen) for 15 min. After wash, the slides were dried and cover slipped with mounting medium (Dako, Carpinteria, CA, USA). Confocal images were acquired with Zeiss ZEN LSM 710 (Zeiss, CA, U.S.A.) and processed with ZEN software.

CP Kits Brain Micodissection Procedure

Following sacrifice and perfusion, one hemisphere of each rabbit kit brain was flash frozen and saved at −80° C. until microdissection was performed following the procedure outline in our recently published manuscript. Briefly, the brains were warmed in disposable petri dishes on a bed of dry ice, then cut into five sections of equal thickness with a clean razor blade. The brain stem and the front section with the olfactory bulb were discarded, after which the cortex was removed from the remaining sections with a fresh scalpel blade and placed in pre-massed 1.5 mL Eppendorf tubes. The hippocampus and periventricular regions were then isolated from the remaining tissue under a magnifying lens and placed in separate pre-massed 1.5 mL Eppendorf tubes. Each Eppendorf tube was massed again to determine the sample mass, then all samples were stored at −80° C. until downstream processing by homogenization and extraction. Three samples of cortex, two samples of PVR, and one sample of hippocampus were obtained for each brain, which were each averaged together to provide one dendrimer uptake value for each brain subunit for each brain.

Dendrimer Extraction from Tissue Samples

Briefly, the organs (heart, lungs, liver, kidneys, brain) were taken out from −80° C., slowly thawed on ice, and weighed. The organs were dissected to take known amount of tissue samples (3 from liver, lungs, kidneys, and 2 from heart). The brain hemispheres were further micro-dissected to separate cortex, hippocampus and periventricular region using our recently published protocol. A known amount of tissue samples was taken from these sub-regions of brain (3 from cortex, 2 from PVR and 1 from hippocampus). The tissue samples were homogenized with 0.9-2.0 mm stainless steel homogenization beads in methanol in a 1 mL:100 mg tissue ratio on a Bullet Blender Storm 24 tissue homogenizer (Next Advantage Inc., Averill Park, NY) for 10 minutes at power level 6 for brain, and power level 12 for all other major organs at 4° C. The homogenized samples were then centrifuged at 15000 rpm for 10 minutes at 4° C. The clear supernatant was transferred to a protein lo-bind Eppendorf tubes and stored at −80° C.

Fluorescence Quantification

The supernatants were thawed, centrifuged again and 130 µL of supernatant was transferred to the micro cuvette (Starna Cell Inc.; Atascadero, CA) for measurement. The fluorescence intensity in each sample was determined for Cy5 ($\lambda$ex=645 nm, xem=662 nm) using RF5301PC spectrofluorophotometer running Panorama3 software (Shimadzu Scientific Instruments, Columbia, MD). The background fluorescence was adjusted from the fluorescence values of healthy control tissue. The fluorescence intensity values were then converted to dendrimer concentrations using calibration curves of D2-OH-60-Cy5 for appropriate slit-widths. Plasma was diluted 10-fold in dPBS (Corning Inc.) then passed through a 0.2 µm pore PES filter and measured as described above for organ samples.

Results

The in vivo BBB penetration and neuroinflammation targeting capabilities of PEGOL-60-Cy5 was evaluated in a neonatal rabbit model of cerebral palsy both qualitatively and quantitatively using confocal microscopy and fluorescent spectroscopy, respectively. CP is caused by an injury/insult to the developing brain, including maternal infection/ inflammation, and results in offspring with motor, sensory, and cognitive impairment (Rosenbaum P N et al., Developmental Medicine & Child Neurology, 49, 8 (2007)). Periventricular leukomalacia, characterized by diffuse microglial and astrocyte activation in the immature white matter, is one of the pathophysiological hallmarks of CP in humans (Haynes R L et al., Journal of Neuropathology & Experimental Neurology, 62, 441 (2003)). Apart from white matter injury, CP also involves neuronal injury in grey matter areas, including the cerebral cortex and hippocampus in CP patients (Andiman S E et al., Brain Pathology, 20, 803 (2010); C. R. Pierson C R et al., Acta Neuropathologica, 114, 619 (2007)).

The uptake of PEGOL-60-Cy5 in the corpus callosum (white matter), hippocampus, and cortex was investigated at 1, 4, and 24 hrs after a single systemic dose in a maternal uterine inflammation induced lapine model of cerebral palsy. This model recapitulates the hallmark microglial and astrocytic pro-inflammatory activation seen in human patients, as well as signature behavioral markers such as hindlimb rigidity and spasticity. CP kits (n=3) received an intravenous administration of PEGOL-60-Cy5 (55 mg/kg) on PND1 and sacrificed 1, 4, and 24 hrs post-injection and were compared to healthy controls (n=3) sacrificed 24 hours after intravenous administration of equivalent dose. The colocalization of PEGOL-60-Cy5 with activated mi/ma, indicated by amoeboid soma with shortened processes, at the corpus callosum, hippocampus, and cortex in CP kits strongly suggests dendrimer accumulation in the activated microglia at these injured sites in the brain (Reid S M et al., Developmental Medicine & Child Neurology, 57, 1159 (2015)). PEGOL-60-Cy5 is mainly distributed in the perinuclear cytoplasm of these activated mi/ma. It is shown that PEGOL-60-Cy5 was able to extravasate from the blood vessels and rapidly localize in activated mi/ma within 1 hr in the injured brain region of the corpus callosum, hippocampus, and cortex. PEGOL-60-Cy5 signal strength increased in activated mi/ma by 4 hrs and was present at similar levels 24 hrs after injection, demonstrating nanoparticle accumulation at the site of injury with potential for local sustained release. In contrast, no co-localization with mi/ma in healthy controls was observed at 24h post-injection.

Figure 8A:
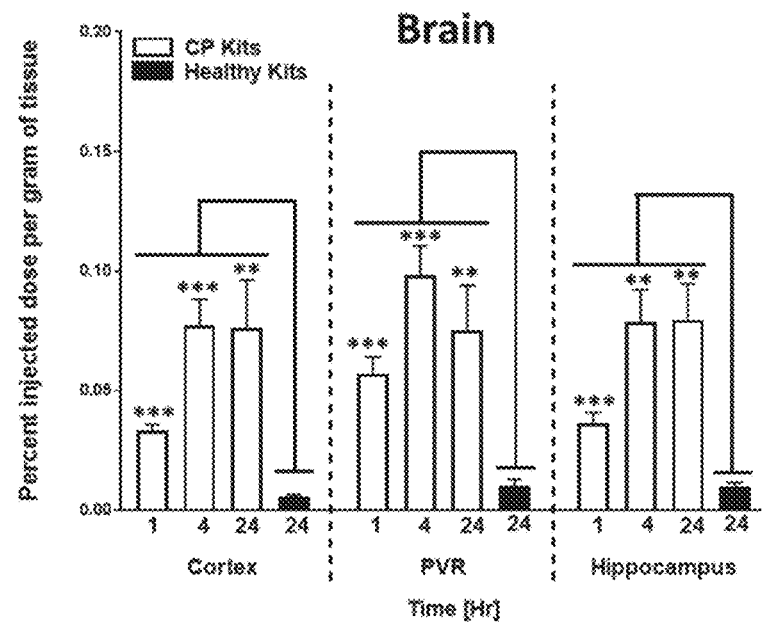
FIGS. 8A-8B are bar graphs FIG. 8A showing quantitative biodistribution of PEGOL-60-Cy5 in neonatal rabbit kits with cerebral palsy in three sub-regions of the brain (cortex, PVR, and hippocampus) at different time points post-injection (1, 4, and 24 hrs; n=6) as compared to age-matched healthy controls (n=4)

Next, the quantitative brain and organ biodistribution of PEGOL-60-Cy5 was studied at three different time points (1 hr, 4 hrs, and 24 hrs) in CP kits (n=6) and compared it to the age-matched healthy controls (n=5). Rather than measure whole brain dendrimer levels as is conventionally done, we micro-dissected the brains to separate the periventricular region (PVR), hippocampus, and cortex to measure the local uptake in these regions where activated microglia are present in this model (A. Sharma, et al., Journal of Controlled Release 2018, 283, 175 (2018)). Earlier studies have shown high engagement of activated mi/ma in the PVR, potentially due to the role of the ventricles as pathways for macrophage recruitment into the brain (W. G. Lesniak, et al., Nance, Mol Pharm, 10 (2013), I. Corraliza, Frontiers in Cellular Neuroscience, 8, 262 (2014)). The hippocampus and cortex are regions implicated in the pathology of cerebral palsy due to their roles in learning, memory, and motor function (Reid S M et al., Developmental Medicine & Child Neurology, 57, 1159 (2015)). This microdissection enables the evaluation of local dendrimer uptake in these clinically relevant subregions of the brain as opposed to overall brain quantities. To avoid the interference of blood and dendrimer stuck in the blood vessels, the kits were perfused with PBS. A significant increase in the dendrimer uptake was detected in the brain of CP animals as compared to healthy controls (FIG. 8A) (p<0.01, student's T-test compared to healthy controls). The selective uptake of PEGOL-60 in the injured brain regions of CP animals could be explained because of its ability i) to cross the impaired BBB, ii) diffuse efficiently within the brain parenchyma due to its neutral charge, and iii) to be picked up by phagocytic activated mi/ma.

Figure 8B:
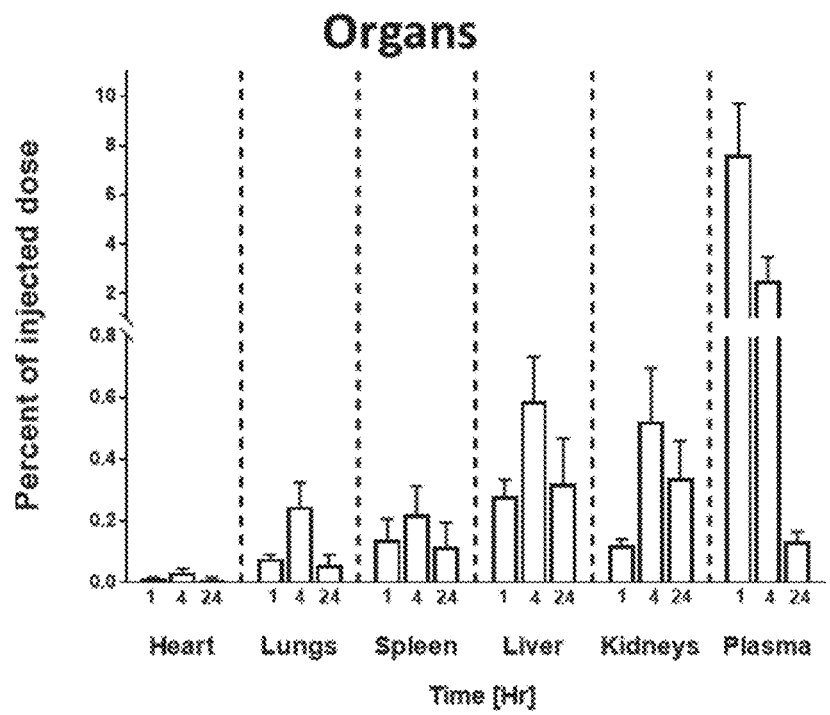

A major concern for the clinical translation of nanomedicine-based therapeutics is their unwanted accumulation in organs other than the area of disease. The biodistribution of PEGOL-60-Cy5 in all major organs (heart, lungs, liver, spleen, kidneys) and plasma was assessed. The results demonstrated a rapid clearance of the dendrimer from the body with an accumulation of less than 1% of the injected dose in any major organ at all-time points (FIG. 8B). A similar trend was observed for all organs with a peak accumulation at 4 hrs and then clearance at 24 hrs. Results were obtained through fluorescence spectroscopy of homogenized tissue extracts and reported in terms of percent of the injected dose in total organ (or total plasma volume). The presence of less than 0.2% dendrimer in serum at 24 hrs post injection shows that the dendrimer clears rapidly from circulation. Interestingly, this dendrimer shows similar levels of brain uptake as we have previously observed in this CP model with PAMAM-D4-OH, nanoparticles of similar size, shape, and number of surface hydroxyl groups, but exhibits much faster clearance rate from circulation and other vital organs (W. G. Lesniak, et al., Nance, Mol Pharm, 10 (2013), I. Corraliza). This rapid clearance rate from the body within 24 hrs, along with the sustained cellular accumulation in the injured regions of the brains of neonatal CP rabbits, make this dendrimer an excellent platform to design therapies for pediatric neuroinflammatory diseases.

Earlier studies have demonstrated that the systemically administered, hydroxyl terminating, generation 4 poly(amidoamine) dendrimers (PAMAM-D4-OH) with 64 terminal hydroxyl groups cross impaired CNS barriers and accumulate specifically in activated mi/ma at the site of brain injury while exhibiting minimal accrual in healthy brain tissue across multiple small and large animal models of neurodegenerative diseases (S. Kannan, et al., Science translational medicine, 4, 130ra46 (2012); S. P. Kambhampati, et al., Invest Ophthalmol Vis Sci, 56 (2015)). Similar neuroinflammation targeting was not observed with cationic and anionic dendrimers of equivalent size and similar backbone (Nance, E., et al., Biomaterials, 101, 96 (2016)). This intrinsic targeting capability is theorized to arise from the high density of surface hydroxyl groups possible with dendrimers due to their unique branching structure (~1 hydroxyl terminal groups per $nm^2$ at generation 4 PAMAM) that is difficult to achieve with other polymeric nanoparticles.

Motivated by these findings, a hydroxyl functionalized PEG based dendrimer nanocarrier has been designed and developed for systemic targeting of activated mi/ma in CNS disorders. This construct was designed to exhibit greater hydroxyl surface density at lower generations than PAMAM dendrimers in order to have similar neuroinflammation targeting capabilities with lower synthetic burden (~5 hydroxyl terminal groups per nm2 at generation 2). Keeping the requirements for clinical translation in mind, this dendrimer was developed as a monodisperse defect-free dendrimer using water soluble, inexpensive, and biocompatible building blocks with minimal reaction steps via highly efficient chemical transformations based on click chemistry. This construct, referred to as D2-OH-60, or PEGOL-60 is made up of PEG based building blocks and has 60 hydroxyl (neutral) surface groups at generation 2, which is produced in four reaction steps, compared to PAMAM-D4-OH, which has 64 hydroxyl surface groups at generation 4 achieved in eight synthesis steps. The PEGOL-60 dendrimer backbone is designed to consist predominantly of stable ether linkages to prevent enzymatic degradation or disintegration in the biological system, allowing it to be excreted intact through the kidneys. PEGOL-60 is designed to exhibit inherent neuroinflammation targeting through its high density of surface hydroxyl terminal groups of 5 groups per $nm^2$, has small size, nearly neutral charge, aqueous solubility, and biocompatibility, thereby streamlining the translation process by eliminating the requirement for post-synthetic modifications.

The ability for PEGOL-60 to target the relevant cells at the site of neuroinflammation was validated in vivo via fluorescence spectrometry-based quantification and confocal microscopy in three different models of CNS diseases to assess the ability of PEGOL-60 to cross both the BBB and the BRB, to penetrate solid tumor, and to target disease-associated microglia and macrophages. To do this a rabbit model of maternal uterine inflammation-induced cerebral palsy (CP), a murine orthotopic model of glioblastoma (GBM) and a rat model of subretinal lipid-induced age-related macular degeneration (AMD) were employed. Upon systemic administration PEGOL-60 successfully crosses the impaired CNS barriers and specifically localizes in activated microglia/macrophages, tumor-associated macrophages, and/or retinal pigment epithelium cells in brain or retina in a rabbit model of cerebral palsy, a mouse model of glioblastoma, and a rat model of age-related macular degeneration, while clearing rapidly from peripheral organs.

The inherent therapeutic properties of PEGOL-60 was also explored in vitro based on previous findings that certain dendrimers exhibit anti-oxidant and anti-inflammatory effects without the addition of therapeutic payloads (M. Hayder, et al., Science Translational Medicine, 3, 81ra35 (2011); K. Neibert, et al., Molecular Pharmaceutics, 10, 2502 (2013)). PEGOL-60 also exhibits powerful inherent anti-oxidant and anti-inflammatory effects in microglia exposed to aninflammatory environment and shows no adverse effects in vitro or in vivo. Finally, the effects of PEGOL-60 on the neurological behaviors in CP kits were also investigated.

This hydroxyl PEG dendrimer can be applied to a wide range of neuroinflammatory diseases as an excellent nanocarrier to deliver therapies specifically to sites of brain injury for enhanced therapeutic outcomes.

Example 10: Robust Synthetic Strategy for Large Scale Dendrimer-Drug Synthesis

NAC is an N-acetyl derivative of naturally occurring amino acid L-cysteine and acts as an anti-oxidant and anti-inflammatory drug. It has been widely used in clinics in children and adults for decades. NAC is a glutamate modulating agent and helps to restore glutathione, body's natural anti-oxidant. Neuroinflammation results in the depletion of glutathione in glial cells which results in loss of their neuroprotective function. NAC is usually given in high doses due to its poor bioavailability because of the presence of thiol group which can bind to proteins. Targeted delivery of NAC using dendrimer platform can not only deliver the NAC selectively to activated glial cells at the site of injury, can also help to reduce neuronal toxicity. Dendrimer-NAC (D-NAC) is 100 fold better than the free drug and has shown significant efficacy in the rabbit model of CP, the mouse model of hypoxic-ischemia, and other neuro-inflammation models in different animals (Kannan, S et al., J. Control. Release 2015, 214, 112).

In order to meet the demand of D-NAC for clinical trials, a well-established, highly reproducible and robust methodology is required to construct this conjugate in kilogram scale. Different synthetic strategies are described to synthesize D-NAC at a large scale.

G4 PAMAM dendrimer-NAC is used as an example to illustrate these synthesis strategies. The synthesis methods described here are generally applicable for dendrimers described above, and other agents to be delivered.

Methods and Materials

Synthesis of Intermediates and Dendrimer-Drug Conjugates Preparation of G4-(OH)39(GABA-NHBOC)25 (Compound 22): To a stirred solution of PAMAM G4-OH (4.85 g; Compound 21) in anhydrous DMF (50 ml) is added Boc-GABA-OH (2.498 g), DMAP (1.67 g) and stirred at room temperature (RT) for 5 minutes to make a clear solution. EDC.HCl (2.94 g) was added in portions to the reaction mixture over the period of 30 minutes. The reaction mixture was stirred for 36 hr at RT. The reaction mixture was transferred to 1 kD MW cut-off cellulose dialysis tubing and dialysed against water for 24 h, periodically changing water 3-4 times. The contents of dialysis tubing were transferred to pre-weighed 50 mL falcon tube and lyophilized to get desired product, Compound 22 as white fluffy hygroscopic solid. Yield: 85%, 5.3 g.

Preparation of G4-$(OH)_{39}(GABA-NHTFA)_{25}$ (compound 23): Took BOC protected dendrimer, Compound 22 (5.3 gm) in a flame dried 250 ml round bottom flask and added 30 ml of DCM to dissolve the compound under Nitrogen atmosphere. The solution was sonicated for 15 minutes to make a homogeneous solution add 10 ml of TFA dropwise while stirring. Reaction mixture was stirred for 12 h at RT. The color of the reaction changed from colorless to light brownish color. Once completed, DCM was evaporated. Diluted the reaction mixture with methanol and evaporated using rotary evaporator. This procedure was repeated until excess of TFA was completely gone. This reaction mixture is left in high vacuum for 3 hours to remove any trace of solvents to afford Compound 23 as a white fluffy hygroscopic material, which can be directly for the next step without any further purification.

Preparation of Compounds 24, 25 and 26: Compound 24 was purchased from Sigma and was used as received. Compounds 25 and 26 were synthesized using previously published protocol (Navath, R. S.; Kurtoglu, Y. E.; Wang, B.; Kannan, S.; Romero, R.; Kannan, R. M. *Bioconjugate Chem.* 2008, 19, 2446).

Preparation of N-acetyl-S-((3-((2,5-dioxopyrrolidin-1-yl) oxy)-3-oxopropyl)thio)cysteine [SPDP-NAC linker](Compound 27): In a flame-dried 100 mL round bottom flask, charged N-Succinimidyl 3-(2-pyridyldithio)-propionate (SPDP, Compound 26) (5 g, 16.02 mmoles) and dissolved in anhydrous tetrahydrofuran (THF, 15 mL) under inert atmosphere. A drop-wise addition of a solution of N-acetyl cysteine (NAC, 2.87 g, 17.62 mmoles, 1.1 eq) dissolved in THF (15 mL) was performed. The reaction mixture turned yellow within few minutes. The reaction mixture was stirred at RT for 4 h. Reaction was monitored by TLC and once the starting material (SPDP) was consumed, the solvent was removed using rotary evaporator. The crude product was purified using prepackaged high performance redisep gold Rf™ 80 gram silica cartridge on CombiFlash systems keeping the flow 60 mL/minute. The column was started in DCM and the pure desired product was collected in 4% MeOH in dichloromethane as white powder in 75.4% yield (4.4 g).

Preparation of Compound 28 (D-NAC): In a flame dried 500 mL round bottom flask, charged Compound 23 (6 g) and dissolved it in anhydrous DMF (40 mL) under inert atmosphere. The flask was sonicated and vortexed until it make a clear solution. The pH of the reaction mixture was adjusted to 7.0-7.5 by addition of diisopropylethylamine. Stirred the reaction mixture for 30 minutes and once the pH is stable slow addition of Compound 27 (4.76 g, 35eq) dissolved in DMF (20 mL) is performed. Stirred the reaction mixture under nitrogen at room temperature for 12 h. The reaction mixture was transferred to 1000 cut-off dialysis bag and dialysed against DMF for 6 hours followed by water for 24 hours, periodically changing solvent every 2-3 hours. The contents of dialysis tubing were transferred to pre-weighed 50 mL falcon tubes and were lyophilized to get Dendrimer-NAC conjugate, Compound 28 as White fluffy powder with Yield: 90%, 7.0 g. The extent of final conjugation was calculated comparing NH protons of dendrimer in between 8-7.5 ppm to N-acetyl protons of NAC at 1.8 ppm and —CH proton of NAC around 4.4 ppm.

Preparation of Compound 29 (D-Allyl): To a stirred solution of PAMAM-G4-OH (Compound 21, 530 mg, 0.037 mmoles) in dry DMF (15 mL), NaH (200 mg, 8.33 mmoles) was added in portions at 0° C. After 15 minutes, allyl bromide (0.127 mL, 1.48 mmoles) was added and the stirring was continued for 24h at RT. The solution was then dialyzed against DMF followed by water for 24h. The aqueous solution was lyophilized to get product as white powder.

Preparation of Compound 30: To a stirred solution of Compound 29 (192 mg, 0.012 mmoles) in DMF (5 mL), 2-(boc-amino) ethanethiol (200 mg, 1.12 mmoles) was added followed by the addition of catalytic amount of 2,2-dimethoxy-2-phenylacetophenone (DMPAP). The reaction mixture was stirred under UV light for 24h. The reaction was dialyzed against DMF followed by water for 24h. The aqueous solution was lyophilized to get product as white powder.

Preparation of Compound 31: To a stirred solution of Compound 30 (200 mg) in DCM (2.5 mL), trifluoroacetic acid (2 mL) was added and stirring was continued for 4 h. The reaction was quenched with methanol and the solvent was evaporated under reduced pressure. Methanol was added and evaporated several times to remove TFA. The residue was dried under reduced pressure to afford hygroscopic solid in quantitative yield.

Preparation of D-NAC$^a$ via ether linker (Compound 28a): In a flame dried 500 mL round bottom flask, charged Compound 31 (300 mg, 0.018 mmoles) and dissolved it in anhydrous DMF (10 L) under inert atmosphere. The flask was sonicated and vortexed until it make a clear solution. The pH of the reaction mixture was adjusted to 7.0-7.5 by addition of diisopropylethylamine. Stirred the reaction mixture for 30 minutes and once the pH is stable, slow addition of Compound 27 (331 mg, 0.909 mmoles) dissolved in DMF (10 mL) was performed. Stirred the reaction mixture under nitrogen at room temperature for 12 h. The reaction mixture was transferred to 1000 cut-off dialysis bag and dialysed against DMF for 6 hours followed by water for 24 hours, periodically changing solvent every 2-3 hours. The contents of dialysis tubing were transferred to pre-weighed 50 mL falcon tubes and lyophilized to get Dendrimer-NAC conjugate, Compound 28b as white fluffy powder.

Preparation of Compound 32: Compound 32 with mixed hydroxyl and amine surface groups was purchased from Dendritech and used as received.

Preparation of D-NAC$^b$ (Compound 28b): In a flame dried 500 mL round bottom flask, charged bifunctional dendrimer, Compound 32 (1 g, 0.071 mmoles) and dissolved it in anhydrous DMF (20 mL) under inert atmosphere. The flask was sonicated and vortexed until it make a clear solution. The pH of the reaction mixture was adjusted to 7.0-7.5 by addition of diisopropylethylamine. Stirred the reaction mixture for 30 minutes and once the pH is stable slow addition of Compound 27 (910 mg, 2.5 mmoles) dissolved in DMF (10 mL) was performed. Stirred the reaction mixture under nitrogen at room temperature for 12 h. The reaction mixture was transferred to 1000 cut-off dialysis bag and dialysed against DMF for 6 hours followed by water for 24 hours, periodically changing solvent every 2-3 hours. The contents of dialysis tubing were transferred to pre-weighed 50 mL falcon tubes and were lyophilized to get Dendrimer-NAC conjugate, Compound 28b as White fluffy powder.

Preparation of Compound 33: To a round bottom flask, aldrithiol-2 (6.19 g) was added and dissolved in 25 mL of methanol. Then add 2-mercaptoethanol that was dissolved in methanol (5 mL) drop wise. The reaction was continued for overnight at room temperature. Afterwards, all the volatiles were evaporated under reduced pressure. The residue was purified by column chromatography by eluting with the mixture of hexane and ethyl acetate. Obtained product (Compound 33) was collected as pure pale yellowish oil (2.14 g, 75% yield).

Preparation of Compound 34: To an oven dried round bottom flask was added with 4-nitrophenylchloroformate (2.30 g) dissolved in 10 mL of anhydrous DCM (10 mL) under $N_2$ gas at room temperature. Then a mixture of 2-pyridyldisulfanylethanol (2.14 g) and pyridine (0.9 mL) that were dissolved anhydrous DCM (5 mL) was added into this solution. After 6 hr, an additional 4-nitrophenylchloroformate (1.16 g) and pyridine (0.5 mL) dissolved in anhydrous DCM (10 mL) was prepared and added into reaction mixture. After overnight stirring at room temperature, the reaction medium was diluted with DCM (ACS grade, 10 mL) and washed with 1M HCl (60 mL) for three times. Collected organic layer was dried over anhydrous $Na_2SO_4$ and filtered. All organic volatiles were evaporated under vacuo and the residue was purified by column chromatography as eluted with the mixture of hexane and ethyl acetate. The product (Compound 34) was collected as pure yellow oil product (3.08 g, 76.2% yield).

Preparation of Compound 35 and D-NAC via carbonate linker (Compound 28c): To an oven-dried 250 mL round bottom flask was charged with PAMAM G6-OH (1.00 g) that was dissolved in anhydrous DMF (15 mL). After stirring the solution in 40° C. oil bath under $N_2$ gas environment, DMAP dissolved in anhydrous DMF (5 mL) was added. Then carbonate linker dissolved in 10 mL of anhydrous DMF was added into this solution and the reaction mixture was stirred for 48 h at 40° C. At the end of reaction, the solution was transferred for dialysis against DMF using dialysis membrane (MWCO 8kD) by changing the solvent at least three times. Dialyzed solution containing Compound 35 was then transferred into a round bottom flask and NAC (0.44 g) dissolved in anhydrous DMF (4 mL) was added drop wise into this solution. After overnight stirring at room temperature, the solution was transferred for dialysis against DMF using dialysis membrane (MWCO 8kD) and the solvent was replaced for at least two times. After adding this solution into ethyl ether anhydrous (100 mL), precipitates were collected as a solid product and dried under reduced pressure overnight. As a last step, the resultant solid was dissolved in DPBS (45 mL) and dialyzed against DI water (MWCO 8kD) for 4 h. The dialyzed solution was lyophilized to obtain the dendrimer-NAC conjugate, D-NAC (Compound 28c) as an off-white solid (1.54 g).

Preparation of Compound 36: Compound 25 (94.8 mg, 0.41 mmol) was dissolved in 1.0 mL anhydrous DMF and into this clear solution DMAP (25.2 mg, 0.21 mmol) and pyBOP (322.7 mg, 0.62 mmol) dissolved in 3.0 mL anhydrous DMF were added. After stirring the reaction mixture at 0° C. for 30 minutes, G6-OH PAMAM dendrimer (200.0 mg, 3.44 µmol) dissolved in 2.0 mL anhydrous DMF was added and the reaction was left to stir for 2 days at room temperature. Then the crude product was dialyzed against DMF to remove by-products and excess reactants, followed by precipitation in diethyl ether to get rid of DMF. Finally purified product was re-dissolved in $H_2O$, lypholized and obtained as a yellow compound (240.0 mg).

Preparation of D-NAC$^d$ via ester linker (28d): Compound 36 (200 mg, 5.02 µmol) was dissolved in 3.0 mL anyhdrous DMF, and then NAC (54.6 mg, 0.334 mmol) dissolved in 2.0 mL anhydrous DMF was added in the round bottom flask. The reaction mixture was stirred for 24h at room temperature. Then, all the volatiles were evaporated and the crude product was purified by dialysis against DMF to remove by-products and excess reactants, followed by water to get rid of all organic solvents. Lastly it was lypholized and obtained as a light yellow compound (180.0 mg).

Preparation of D-NAC-NAC (Compound 37): To a stirred solution of Compound 21 (400 mg, 0.027 mmoles) in DMF (10 mL), NAC dimer (363 mg, 1.12 mmoles), EDC (300 mg, 1.562 mmoles) and DMAP (136 mg, 1.114 mmoles) were added. The reaction mixture was stirred for 48h at 40° C. The reaction mixture was transferred to 1000 cut-off dialysis bag and dialysed against DMF for 24 hours followed by water for 24 hours, periodically changing solvent every 2-3 hours. The contents of dialysis tubing were transferred to pre-weighed 50 mL falcon tubes and lyophilized to get D-NAC-NAC conjugate 37 as light yellow powder.

Preparation of Compound 38: N-acetyl cysteine was reacted with excess 2, 2'-dithiodipyridine in methanol overnight and the obtained crude was purified by column chromatography with an eluent system of ethylacetate:hexane (90:10). The purified light yellow compound (Compound 38) was characterized by $^1$HNMR spectroscopy.

Preparation of Compound 39: Compound 38 (919.64 mg, 3.38 mmol) was dissolved in 4.0 mL anhydrous DMF and into this clear solution DMAP (206.27 mg, 1.69 mmol) and pyBOP (2.64 g, 5.07 mmol) dissolved in 8.0 mL anhydrous DMF were added. After stirring the reaction mixture at 0° C. for 30 minutes, G4-PAMAM dendrimer (0.40 mg, 28.14 µmol) dissolved in 8.0 mL anhydrous DMF was added and the reaction was left to continue for 3 days at room temperature. Then the crude product was diluted with DMF and dialyzed against DMF to remove by-products and excess reactants, followed by H2O to get rid of any organic solvent. Finally purified product was lyophilized and obtained as a light yellow solid (358.0 mg) (Mwt. theo of product: 20319 gmol-1, # of NAC/PAMAM: 24, % of NAC (w/w): 19.2, % purity derived from HPLC: 90.64, Hd: 2.38-0.26 nm, PDI: 0.74, Zeta potential: 4.41±0.61 mV).

Preparation of D-NAC-NAC (Compound 40): Compound 39 (300.0 mg, 14.76 µmol) and N-acetyl cysteine (115.6 mg, 0.71 mmol) were dissolved in 15.0 mL DMF. After 24h stirring at room temperature, the reaction mixture was diluted with DMF and dialyzed against DMF to remove excess free drug molecules and then followed by $H_2O$ to get rid of any organic solvent. After the precipitation of the product in cold diethyl ether, final dendrimer-drug conjugate was lyophilized and obtained as a light yellow solid (Compound 40) (250.0 mg). Mwt. theo of product: 21568 gmol-1, # of NAC/PAMAM: 48, % of NAC (w/w): 36.3, % purity derived from HPLC: 98.47, Hd: 4.90±0.24 nm, PDI: 0.48, Zeta potential: 3.64±1.14 mV).

Results

Dendrimer-NAC is undergoing clinical translation. To meet preclinical/clinical needs, a highly optimized and systematic synthetic protocol is required, which can generate kilogram scale quantities of D-NAC with high reproducibility, purity and yields with the minimum number of reaction steps. In this Example, a scalable protocol for D-NAC synthesis (Strategy 1) is described. It is validated on a 10 gram scale in an academic research lab and kilogram scale by a contract research laboratory. In addition, several other convenient and facile synthetic methodologies to construct D-NAC with modifications in the linkers on the dendrimer are also developed (Strategies 2 to 6).

Strategy 1: D-NAC Via Ester Linker

Figure 14:
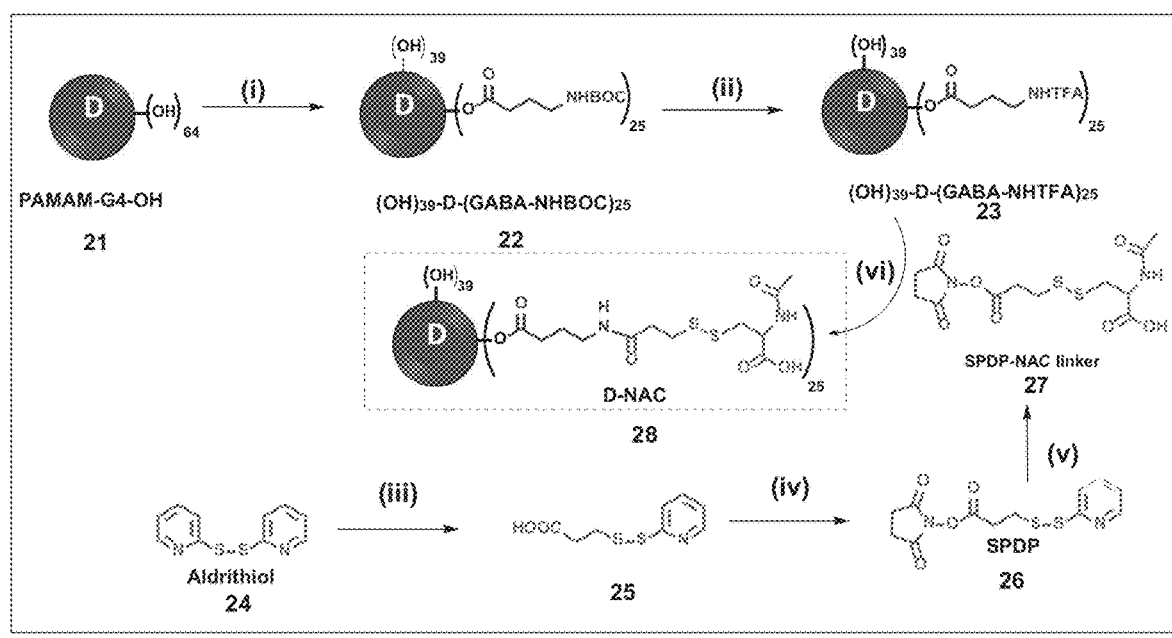
FIG. 14 Scheme 7: Key steps in synthetic pathway of D-NAC (Compound 28). Reagents and conditions: (i) EDC, DMAP, DMF, 36h, RT, 85%; (ii) DCM:TFA (3:1), RT 12h, quantitative yield; (iii) 3-Mercapto propionic acid, acetic acid, anhydrous ethanol, 2h, RT, 78%; (iv) DCC, N-hydroxysuccinimide, DCM, 0oC-RT, 3h, 82%; (v)N-Acetyl-L-cysteine, anhydrous THF, 2h, 65%. (vi) N, N-diisopropylethylamine, pH 7.5, DMF, RT, 24h, 90%.

The goal is to develop and design a near perfect synthetic route which has the potential to reduce cost at multiple levels. A scalable process for D-NAC synthesis was developed and validated, (Scheme 7 FIG. 14) which has been transferred to potential cGMP manufacturers. This synthetic protocol: (1) has decreased the synthesis time by half, (2) uses 'manufacturing friendly' solvents and reagents, (3) has improved the purity and reduced the solvent use.

One of the costliest component of the synthetic protocol is the synthesis of the dendrimer, e.g., generation 4 PAMAM dendrimer, and at each synthetic step there is some yield loss of dendrimer while performing purification. To overcome this loss, the number of reaction steps on dendrimer is minimized in this protocol. Half of the reaction steps involve small molecule synthesis which is indeed less complex and expensive than dealing with dendrimers.

D-NAC is a conjugate of generation-4 hydroxyl terminal PAMAM dendrimer covalently conjugated to NAC linked through disulfide bonds. D-NAC contains an average of 22±3 NAC molecules attached to the dendrimer. The synthesis is carried out in a semi-convergent way and involves the construction of two main intermediates: 1) bifunctional dendrimer (Compound 23, Scheme 7 FIG. 14); 2) NAC-SPDP-NHS (N-acetyl-S-((3-((2,5-dioxopyrrolidin-1-yl)oxy)-3-oxopropyl)thio)cysteine) linker (Compound 27, Scheme 7 FIG. 14). The final step involves the stitching of these two intermediates to yield the final conjugate (Compound 28).

More specifically, during the first step BOC protected bifunctional dendrimer (Compound 22) was constructed using esterification reaction in the presence of BOC-GABA-OH, and coupling agents (EDC and DMAP). The attachment of 22-25 linkers was observed through $^1$H NMR by comparing the integration from different regions in the conjugate. The deprotection of BOC was carried out using 25% trifluoroacetic acid (TFA) in anhydrous dichloromethane (DCM) leading to bifunctional dendrimer with 22-25 terminal amines (Compound 23). Proton NMR clearly showed the disappearance of the peak corresponding to BOC protons.

On the other hand, the synthesis of NAC-SPDP-NHS-linker (Compound 27) was achieved in 3 steps. First, 3-mercaptopropionic acid was reacted by thiol-disulfide exchange with 2,2'-dipyridyl disulfide (Compound 24) to give 2-carboxyethyl 2-pyridyl disulfide (Compound 25). It was followed by the esterification with N-hydroxysuccinimide using N,N'-dicyclohexylcarbodiimide to introduce highly reactive N-succinimidyl ester to get Compound 26. N-acetyl cysteine was finally added through thiol-disulfide exchange to yield N-acetyl-S-((3-((2,5-dioxopyrrolidin-1-yl)oxy)-3-oxopropyl)thio)cysteine (Compound 27).

During the final ligation step, bifunctional amine terminated dendrimer (Compound 23) and activated NAC-SPDP-NHS (Compound 27) were coupled using Hunig's base at pH-7.5-8 to yield D-NAC (Compound 28). All the intermediates and the final conjugate were well characterized using $^1$H NMR and mass spectroscopy (LCMS/MALDI-ToF). The purity of the intermediates and final D-NAC conjugate was accessed using HPLC. The size of D-NAC is 5.649 nm as measured by dynamic light scattering and the conjugate has neutral zeta potential 3.92±1.18 mV.

Reproducibility of NAC Loading

Figure 15:
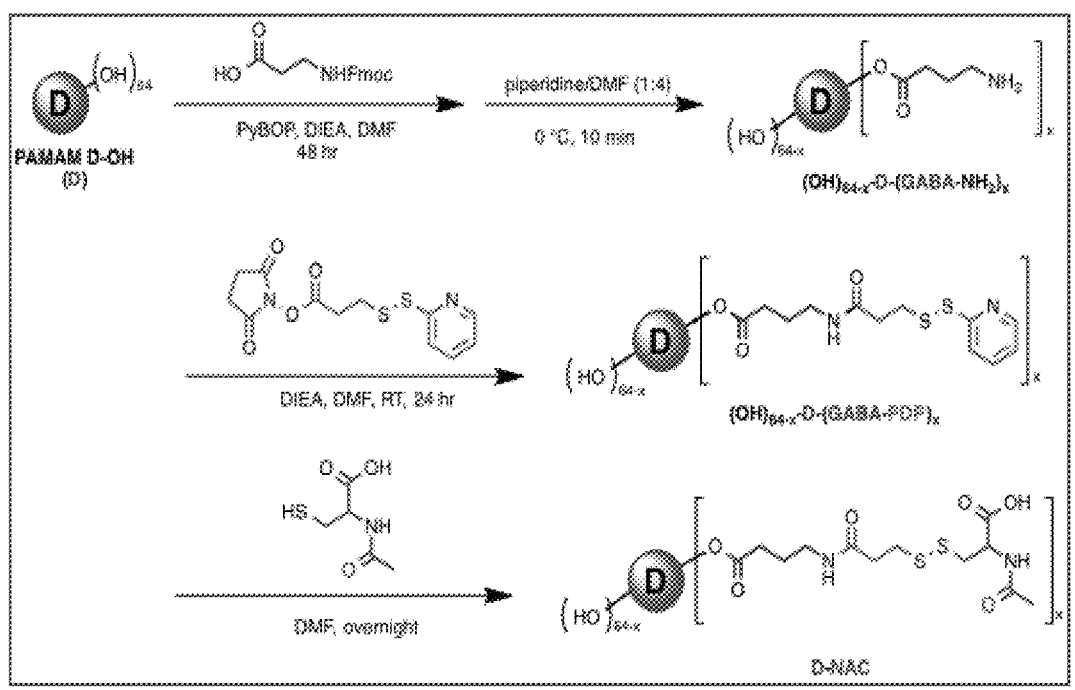
FIG. 15 Scheme 8. Previous strategy for D-NAC synthesis.
Figure 16:
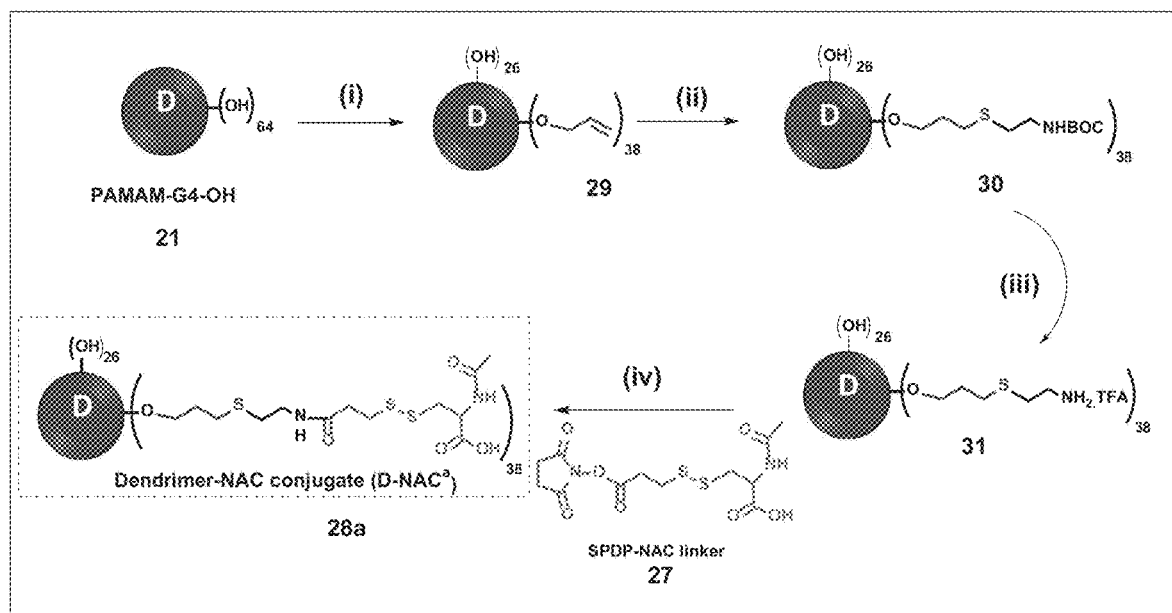
FIG. 16 Scheme 9: Key steps in synthetic pathway of D-NACa via ether linker (8a). Reagents and conditions: (i) Allyl bromide, NaH, DMF, 24h (ii) BOC-aminoethanethiol, DMPAP, UV, R TFA, RT, 24h, (iv) N, N-diisopropylethylamine, pH 7.5, DMF, RT, 24h.

The first step in the previous protocol (Scheme 8 FIG. 15) used Fmoc-Y-Abu-OH which needs to be deprotected using basic conditions (piperidine/DMF). This deprotection step is a critical step and affects the loading efficiency of the final drug. As the ester linkage between the dendrimer and the linker is prone to basic hydrolysis, the excess piperidine/DMF used for deprotection leads to the partial cleavage of linker as well, leading to inconsistency in the final loading of drug in different batches. In the newly developed methodology (Scheme 9 FIG. 16), Fmoc-Y-Abu-OH was replaced with BOC-GABA-OH. BOC protecting group can easily be removed in mild acidic conditions using 25% TFA in DCM keeping the ester linkages intact. This step has been reproduced several times on 10 g scale with consistent results showing no ester hydrolysis.

Shortening the Synthesis Time

The previous protocol for the synthesis of D-NAC contains 3 steps of dialysis against DMF for at least 24 hr followed by water for another 24 hours at each step (after conjugation of Fmoc-Y-Abu-OH, after Fmoc-deprotection, and after conjugation of NAC) to remove the excess reagents and side products. In the newly developed protocol, the process only requires 1 step of dialysis against both DMF and water (final step after conjugation of NAC-SPDP). Moreover, in the previous strategy, every step was performed on the dendrimer.

Each step on the dendrimer takes at least 2 days of dialysis followed by 2 days of lyophilization making the synthesis 3-4 weeks long. However, in the new protocol SPDP-NAC linker is synthesized separately in a few hours. This significantly shortens the timeframe of synthesis which can be achieved in 7-10 days.

Economic and Industrial Friendly Protocol

In the previous protocol, in order to compensate for ester hydrolysis during the deprotection step, excess of the linker is required for high loading. The improved methodology is more robust and does not require high loading of linker as there is no linker hydrolysis during the deprotection step, saving cost. Moreover, as there is only one step in the new protocol which requires DMF dialysis, it makes the synthesis greener, economic and industrial friendly. The dendrimer is the most expensive material in the synthesis. Each step of dialysis leads to the loss of some dendrimer. In the new protocol, the number of synthesis steps on the dendrimer are reduced leading to a reduction in cost.

Strategy 2: D-NAC Via Ether Linker and Copper-Free Thiol-Ene Click Chemistry

In the quest to simplify the chemistry to prepare dendrimer-NAC conjugate, highly robust chemical transformations are sought after, for example thiol-ene click, thiol-yne click, or copper-catalyzed alkyne-azide click reaction (Sharma, R et al., *Chem. Commun.* 2014, 50, 13300; Sharma, R et al., *Polym. Chem* 2014, 5, 4321; Sharma, R et al., *Polym. Chem* 2015, 6, 1436; Sharma, R et al., *Nanoscale* 2016, 8, 5106; Sharma, A et al., *RSC Adv.* 2014, 4, 19242; Sharma, A et al., *ACS Macro Lett.* 2014, 3, 1079; Sharma, A et al., *Macromolecules* 2011, 44, 521; and Nguyen, P T et al., *RSC Adv.* 2016, 6, 76360). In the past decade, click chemistry has revolutionized the field of synthetic chemistry and has immensely contributed towards the construction of highly complex polymeric and dendtritic structures.

In the next attempt, the ester linkage through which the linker is attached on the dendrimer in first step in Strategy 1 is eliminated using photochemical-thiol-ene click reaction. Although this ester bond on the surface of the dendrimer is hindered and is not cleaved easily by esterase, it was desirable to develop more a robust conjugate with non-cleavable linkages other than the cleavable disulfide bond. For that purpose, the linker is conjugated on the dendrimer in the first step by a non-cleavable ether bond (Scheme 9 FIG. 16). The ether linkages are robust, do not undergo hydrolysis and are not substrates of esterase.

More specifically, G4-OH (Compound 21) was reacted with allyl bromide in the presence of sodium hydride. The number of linkers conjugated on the dendrimer surface was easily calculated through proton NMR by comparative integration of BOC protons of the linker and internal amide protons of the dendrimer. The BOC was then deprotected using TFA following similar conditions as described in strategy 2 to afford bifunctional ether linked dendrimer (Compound 30). The proton NMR clearly reveals the disappearance of BOC protons in the spectrum. The bifunctional dendrimer conjugate, Compound 30 was finally reacted with SPDP-NAC-linker (Compound 27) to afford D-NACa (Compound 28a) with ether linkages on dendrimer surface. All the intermediates and final conjugate was characterized by $^1$H NMR and HPLC.

The presence of ether bonds in the conjugate are highly stable and do not interfere with the release of NAC. Moreover, ether bonds instead of ester linkage might improve the stability and in turn the shelf life of the conjugate.

Strategy 3: D-NAC Via Amide Linker (without GABA Linker)

Figure 17:
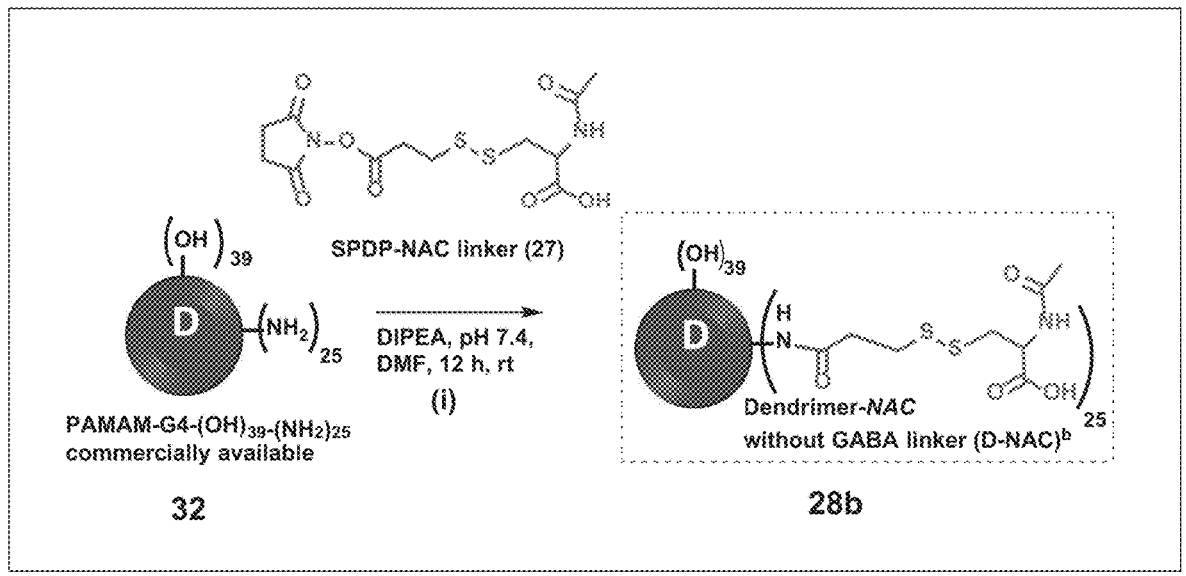
FIG. 17 Scheme 10: Key steps in synthetic pathway of D-NACb (Compound 28b) without GABA linker. Reagents and conditions: (i) N, N-diisopropylethylamine, pH 7.5, DMF, RT, 24h.

The synthesis of D-NAC described in Strategy 1 is highly efficient in terms of scalability and provides access to bulk materials with ease. At the same time one important goal is to develop a perfect synthetic design which will have the potential to reduce cost at multiple levels. To minimize the number of reaction steps on dendrimer and to reduce the overall reaction steps strategy 3 (Scheme 10 FIG. 17) was devised. In this strategy, a completely convergent route was used; where SPDP-NAC-Linker (Compound 27) is directly conjugated to the commercially available bifunctional dendrimer in one synthetic step without GABA linker. The amines are inherent part of the dendrimer surface. The major advantages of this approach include that the number of reaction steps greatly reduced and the most of the reaction steps involve less expensive small molecule synthesis. There is only one reaction step on the dendrimer. The SPDP-NAC-linker (7) was synthesized as previously described in this report and was further reacted the amine groups of commercially available bifunctional PAMAM dendrimer (60% OH/40% NH$_2$, Compound 32) at pH 7.5 in DMF to afford desired dendrimer-NAC conjugate, Compound 28b. All the intermediates and final compound were characterized extensively using NMR spectroscopy, high resolution mass spectroscopy, HPLC and MALDI-TOF mass spectroscopy.

Strategy 4: D-NAC Via Carbonate Linker (without GABA Linker)

Figure 18:
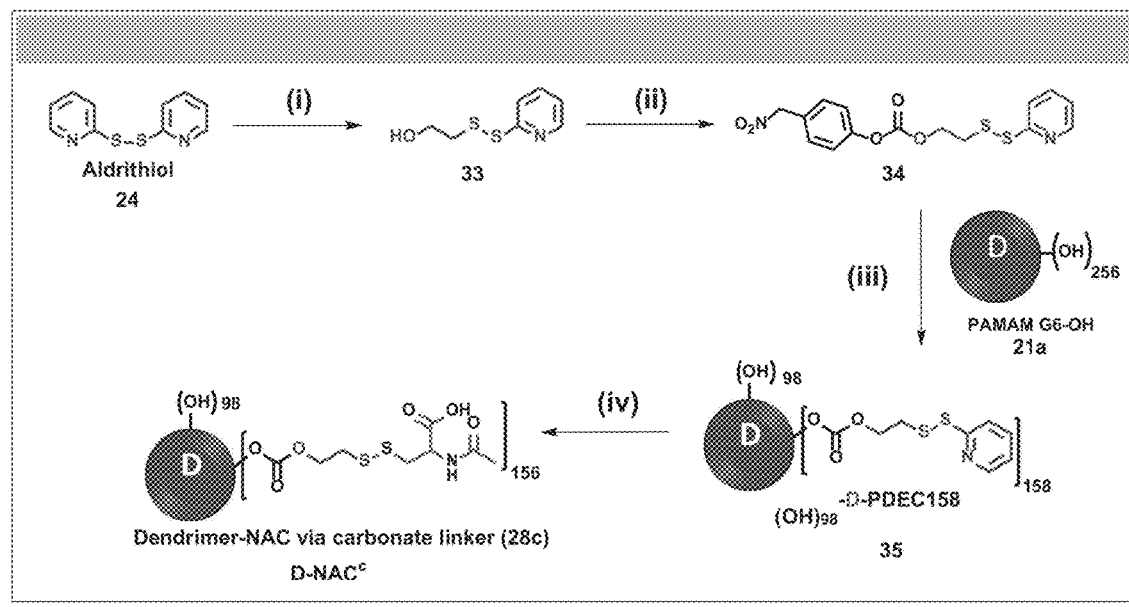
FIG. 18 Scheme 11: Key steps in synthetic pathway of D-NACc (Compound 28c) via carbonate linker. Reagents and conditions: (i) 2-mercaptoethanol, anhydrous methanol, 3h, RT, 75%; (ii) 4-nitrophenylchloroformate, pyridine, anhydrous DCM, 24h, RT, 76%; (iii) DMAP, anhydrous DMF, 48h, 40° C.; (iv)N-Acetyl-L-cysteine, anhydrous DMF, 24h, RT.

In another attempt to improve dendrimer-NAC synthesis, 2-pyridyldisulfylethyl carbonate ester (PDEC) was used as the linker to construct D-NAC$^c$ (Strategy 4). This new methodology of synthesis of D-NAC (Compound 28c) possesses several advantages. The protocol eliminates the use of SPDP cross-linker. Though SPDP is widely used in bioconjugation, it is economically not favorable for large-scale syntheses ($4,500/5-g, price according to Toronto Research Chemicals). PDEC linker was used as it can be easily synthesized using less expensive reagents. Aldrithiol was reacted with mercaptoethanol to obtain Compound 33 (Scheme 11 FIG. 18). The hydroxyl focal point of Compound 33 was reacted with 4-nitrophenylchloroformate to achieve Compound 34, which was reacted directly with PAMAM-OH to attach the linker through carbonate bonds on the dendrimer, Compound 35. Finally, NAC was introduced through disulfide exchange reaction (Compound 28c).

Strategy 5: D-NAC Via Ester Linker (without GABA Linker)

Figure 19:
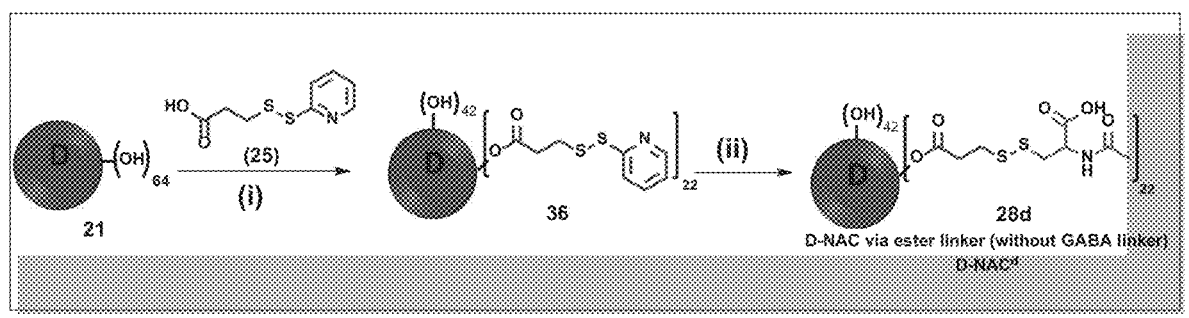
FIG. 19 Scheme 12: Key steps in synthetic pathway of D-NACd (8d) via ester linker. Reagents and conditions: (i) PyBOP, DMAP, anhydrous DMF, 2d, 0oC-RT; (ii)N-Acetyl-L-cysteine, anhydrous DMF, 24h, RT.

In order to reduce the number of steps and reagents to reduce the cost, Compound 25 was directly used as a linker. Instead of conjugating GABA-BOC-OH as described in strategy 1 and then deprotecting it to get free amines, pyridine disulfide linker (Compound 25) was directly reacted via ester bonds on the dendrimer to get Compound 36 (Scheme 12 FIG. 19). The Compound 36 was then subjected to sulfide exchange reaction with NAC to get GABA free ester linked dendrimer-NAC conjugate (D-NAC$^I$, Compound 28d). This strategy significantly reduced the number of synthetic steps in the protocol, thus reducing the time and making the synthesis process much economical.

Strategy 6: D-NAC-NAC (Direct Conjugation)

Figure 20:
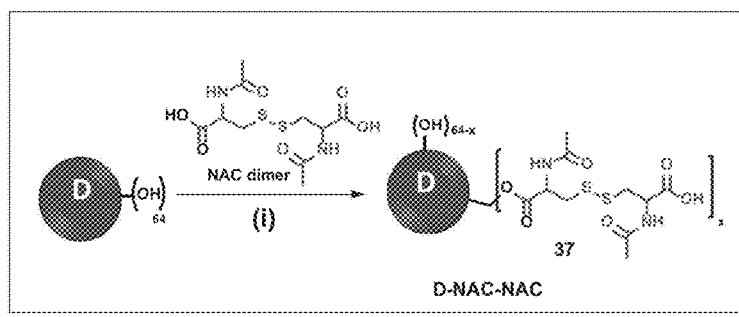
FIG. 20 Scheme 13: Key steps in synthetic pathway of D-NAC-NAC. Reagents and conditions: (i) N,N'-Diacetyl-L-cysteine, EDC, DMAP, DMF, 48h FIG. 21 Scheme 14: Key steps in synthetic pathway of D-NAC-NAC. Reagents and conditions: (i)N-Acetyl-L-cysteine, anhydrous methanol, 3h, RT, 75%; (ii) PyBOP, DMAP, anhydrous DMF, 3d, 0oC-RT; (iii)N-Acetyl-L-cysteine, anhydrous DMF, 24h, RT.

In order to increase the NAC loading while keeping the dendrimer's inherent targeting capability intact (using minimum surface hydroxyl groups for conjugation), a strategy to attach two molecules of NAC per hydroxyl site on dendrimer was designed and developed (Scheme 13 FIG. 20). This strategy has several advantages: 1) using similar number of hydroxyl groups on dendrimer, the NAC loading can be doubled; 2) half of the NAC molecules are conjugated through glutathione sensitive disulfide linkage, while the other half is linked through ester bonds which require esterase to hydrolyze and release the free drug. This can lead to sustained release of NAC. In order to construct D-NAC-NAC, N,N-Diacetyl-L-cysteine (NAC dimer) was directly conjugated on the surface of hydroxyl groups through ester linkage using EDC and DMAP to obtain D-NAC-NAC (Compound 37), where half of the NAC molecules are conjugated through ester bonds on the surface of the dendrimer and half through disulfide bond with another NAC molecule.

Strategy 7. D-NAC-NAC

Figure 21:
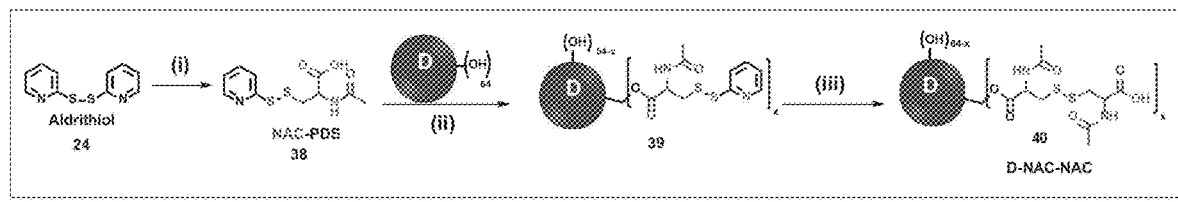

A further synthetic route was developed for D-NAC-NAC (Scheme 14 FIG. 21). NAC was reacted with aldrithiol (Compound 24) by disulfide exchange reaction to get Compound 38. The free group of NAC in Compound 38 was utilized to react with hydroxyl groups of dendrimer to form ester bonds in conjugate, Compound 39. The conjugate, Compound 39 was then reacted with another NAC molecule by second disulfide exchange reaction to get final conjugate D-NAC-NAC (Compound 40).

SSThe synthetic protocol designed here for the construction of D-NAC is highly robust and reproducible, involves industrial friendly solvents, and provides a rapid synthesis of the final conjugate with ease. The improved synthesis of D-NAC also allows production of D-NAC with other linkages and building blocks.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A dendrimer comprising a central core, one or more branching units,
and a plurality of terminal hydroxyl groups,
wherein the dendrimer is a generation 2 dendrimer having a surface density of the hydroxyl groups of at least three hydroxyl groups/nm$^2$, as measured by dynamic light scattering,
wherein the central core is prepared from one or more compounds selected from the group consisting of dipentaerythritol, azide-modified dipentaerythritol, alkyne-modified dipentaerythritol, pentaerythritol, azide-modified pentaerythritol, and alkyne-modified pentaerythritol,
wherein the one or more branching units comprise a linear or branched polyethylene glycol,
wherein one or more prophylactic, therapeutic, or diagnostic agents are encapsulated in, associated with, or conjugated to the dendrimer, and the dendrimer is formulated for systemic administration for local treatment of inflammation mediated by activated macrophages or microglia.

2. The dendrimer of claim 1, wherein the surface density of the hydroxyl groups is at least four hydroxyl groups/nm$^2$.

3. The dendrimer of claim 1, wherein the surface density of the hydroxyl groups is between about 4 and about 15 hydroxyl groups/nm$^2$.

4. The dendrimer of claim 1, wherein the dendrimer has a molecular weight between about 500 Daltons and about 100,000 Daltons.

5. The dendrimer of claim 1, wherein the dendrimer has a molecular weight between about 500 Daltons and about 50,000 Daltons.

6. The dendrimer of claim 1, wherein the dendrimer has a molecular weight between about 1,000 Daltons and about 10,000 Daltons.

7. The dendrimer of claim 1, wherein the dendrimer has a hydrodynamic diameter between about 1 nm and about 15 nm.

8. The dendrimer of claim 1, wherein the dendrimer has a hydrodynamic diameter between about 1 nm and about 5 nm.

9. The dendrimer of claim 1, wherein the dendrimer has a hydrodynamic diameter between about 1 nm and about 2 nm.

10. The dendrimer of claim 1, wherein the central core is prepared from alkyne-modified dipentaerythritol.

11. The dendrimer of claim 1, wherein the one or more branching units are prepared from a linear or branched polyethylene glycol of the following formula:

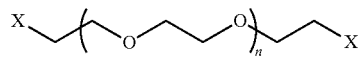

wherein:

n is 1-300; and

X is selected from the group consisting of amine, acid, aldehyde, alcohol, acetylene, allyl, acrylate, azide, tosyl, mesylate, thiol, N-hydroxy succinimide activated acid, and maleimide.

12. The dendrimer of claim 1, wherein the dendrimer is of the following formula:
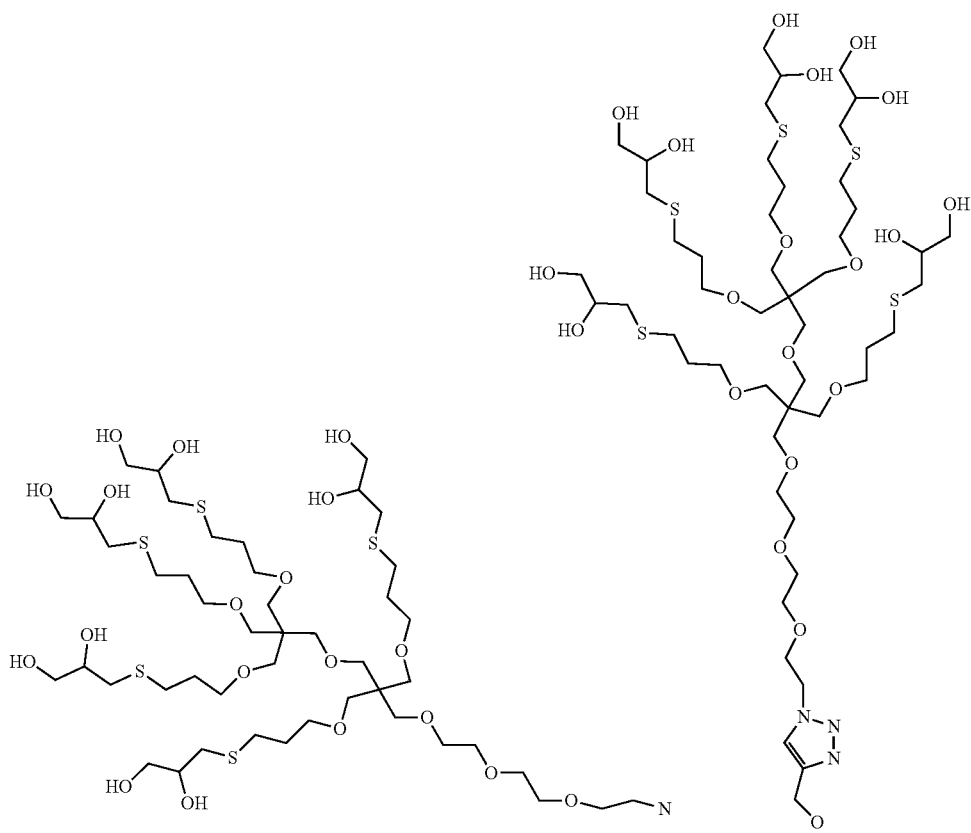

-continued
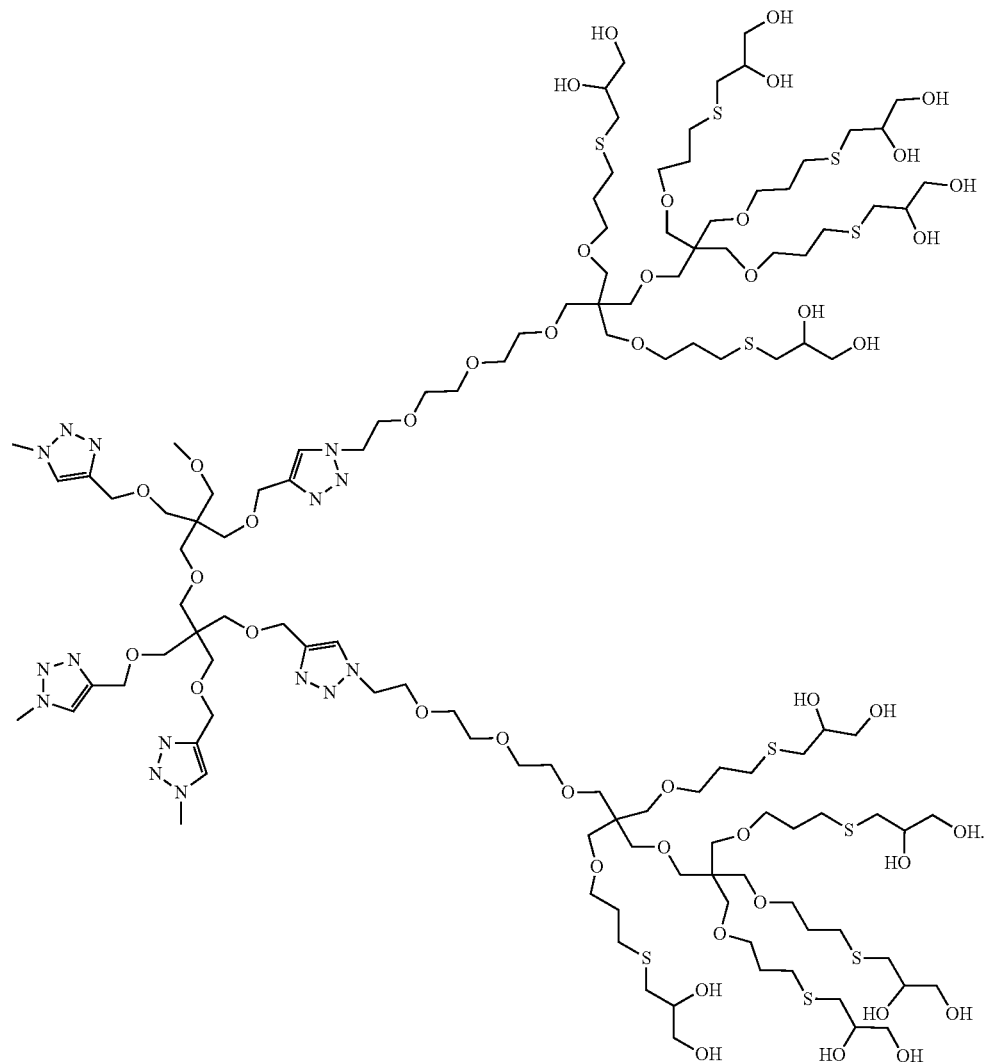

-continued

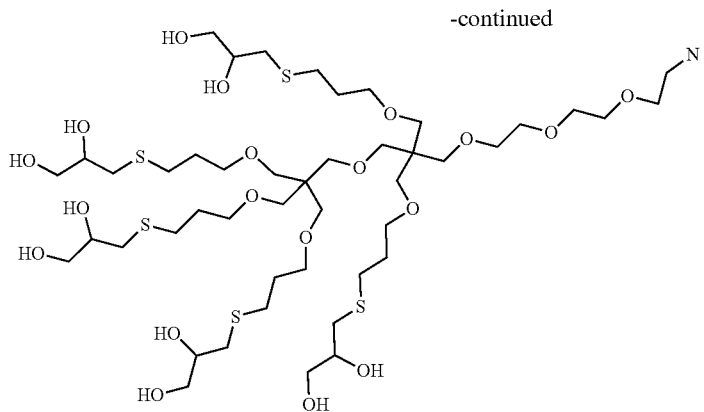
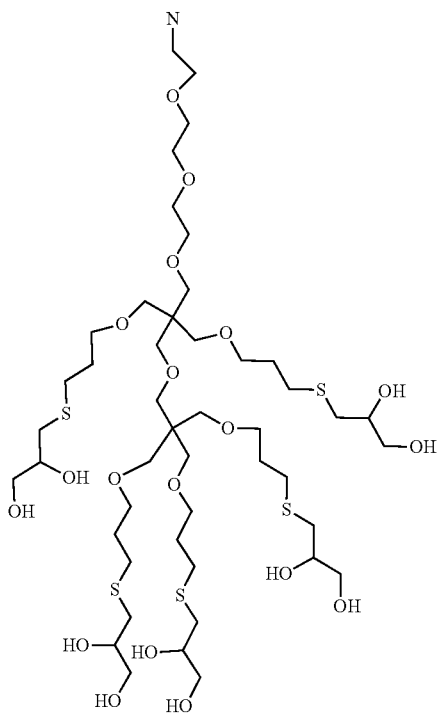

13. The dendrimer of claim 1, wherein the dendrimer is in the form of a dendron.

14. The dendrimer of claim 1, comprising multiple dendrimers organized into tectodendrimers.

15. The dendrimer of claim 1, comprising one or more prophylactic, therapeutic, or diagnostic agents conjugated to the dendrimer.

16. The dendrimer of claim 1, wherein the one or more prophylactic, therapeutic, or diagnostic agents are encapsulated in, associated with, or conjugated to the dendrimer at a concentration of between about 0.01% and about 30%.

17. The dendrimer of claim 1, wherein the one or more prophylactic, therapeutic, or diagnostic agents are covalently conjugated to the dendrimer, via one or more spacers.

18. The dendrimer of claim 1, wherein the one or more prophylactic, therapeutic, or diagnostic agents are covalently conjugated to the dendrimer via one or more linkages selected from the group consisting of disulfide, ester, ether, thioester, carbamate, carbonate, hydrazine, and amide linkages.

19. The dendrimer of claim 17, wherein the spacer is a prophylactic, therapeutic, or diagnostic agent.

20. The dendrimer of claim 19, wherein the spacer is N-acetyl cysteine.

21. The dendrimer of claim 1, wherein the one or more therapeutic agents are selected from the group consisting of anti-inflammatory drugs, chemotherapeutics, vasodilators, and anti-infective agents.

22. A method for treating, preventing, or imaging one or more diseases, conditions, or injuries of the eye, the brain or the nervous system comprising administering to a subject in need thereof the dendrimers of claim 1, wherein the dendrimers are in an amount effective to treat or alleviate one or more symptoms of the one or more diseases, conditions, or injuries of the eye, the brain or the nervous system.

23. The method of claim 22, wherein the one or more diseases, conditions, or injuries of the eye, the brain or the nervous system are diseases, conditions, and injuries associated with activated microglia and astrocytes.

24. The method of claim 22, wherein the dendrimers are in an amount effective to target activated microglia and astrocytes.

25. The method of claim 22, wherein the dendrimers are in an amount effective to treat or alleviate one or more symptoms of one or more diseases, conditions, or injuries of the brain or nervous system.

26. The method of claim 22, wherein the dendrimers are administered intravenously.

27. The dendrimer of claim 16, wherein the dendrimer is complexed or conjugated to one or more therapeutic, prophylactic, or diagnostic agents at a concentration of between about 1% and about 20%.

28. The dendrimer of claim 1, wherein the activated macrophages are resident macrophage cells of the central nervous system.

* * * * *

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Synthetic Primer

<400> SEQUENCE: 1
ccagtgtggg aagctgtctt                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2
aagcaaaaga ggaggcaaca                                              20
```

```
<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
tccagttgcc ttcttgggac                                              20

<210> SEQ ID NO 4
<211> LENGTH: 22
<212> TYPE: DNA
<213> ORGANISM: Artificial Sequence
<220> FEATURE:
<223> OTHER INFORMATION: Synthetic Primer

<400> SEQUENCE: 4
gtgtaattaa gcctccgact tg                                           22

<210> SEQ ID NO 5
<211> LENGTH: 24
<212> TYPE: DNA
<213> ORGANISM: Artificial Sequence
<220> FEATURE:
<223> OTHER INFORMATION: Synthetic Primer

<400> SEQUENCE: 5
tcatggaagt gaacccaact cttg                                         24

<210> SEQ ID NO 6
<211> LENGTH: 23
<212> TYPE: DNA
<213> ORGANISM: Artificial Sequence
<220> FEATURE:
<223> OTHER INFORMATION: Synthetic Primer

<400> SEQUENCE: 6
tcagtccctg gcttatggtt acc                                          23

<210> SEQ ID NO 7
<211> LENGTH: 17
<212> TYPE: DNA
<213> ORGANISM: Artificial Sequence
<220> FEATURE:
<223> OTHER INFORMATION: Synthetic Primer

<400> SEQUENCE: 7
tgtagggctt ccaaggt                                                 17

<210> SEQ ID NO 8
<211> LENGTH: 19
<212> TYPE: DNA
<213> ORGANISM: Artificial Sequence
<220> FEATURE:
<223> OTHER INFORMATION: Synthetic Primer

<400> SEQUENCE: 8
gaaagagtct ctgcagctc                                               19

<210> SEQ ID NO 9
<211> LENGTH: 25
<212> TYPE: DNA
<213> ORGANISM: Artificial Sequence
<220> FEATURE:
<223> OTHER INFORMATION: Synthetic Primer
```

<400> SEQUENCE: 9
tgtcgtggag tctactggtg tcttc                                    25

<210> SEQ ID NO 10
<211> LENGTH: 21
<212> TYPE: DNA
<213> ORGANISM: Artificial Sequence
<220> FEATURE:
<223> OTHER INFORMATION: Synthetic Primer

<400> SEQUENCE: 10
cgtggttcac acccatcaca a                                        21

<210> SEQ ID NO 11
<211> LENGTH: 20
<212> TYPE: DNA
<213> ORGANISM: Artificial Sequence
<220> FEATURE:
<223> OTHER INFORMATION: Synthetic Primer

<400> SEQUENCE: 11
tagtagcaaa cccgcaagtg                                          20

<210> SEQ ID NO 12
<211> LENGTH: 22
<212> TYPE: DNA
<213> ORGANISM: Artificial Sequence
<220> FEATURE:
<223> OTHER INFORMATION: Synthetic Primer

<400> SEQUENCE: 12
ctgaagagaa cctgggagta ga                                       22

<210> SEQ ID NO 13
<211> LENGTH: 20
<212> TYPE: DNA
<213> ORGANISM: Artificial Sequence
<220> FEATURE:
<223> OTHER INFORMATION: Synthetic Primer

<400> SEQUENCE: 13
tgccaaccct acaacaagag                                          20

<210> SEQ ID NO 14
<211> LENGTH: 20
<212> TYPE: DNA
<213> ORGANISM: Artificial Sequence
<220> FEATURE:
<223> OTHER INFORMATION: Synthetic Primer

<400> SEQUENCE: 14
aaagttctca ggccgtcatc                                          20

<210> SEQ ID NO 15
<211> LENGTH: 22
<212> TYPE: DNA
<213> ORGANISM: Artificial Sequence
<220> FEATURE:
<223> OTHER INFORMATION: Synthetic Primer

<400> SEQUENCE: 15
catcaaggag ctgaggaaag ag                                       22

<210> SEQ ID NO 16
<211> LENGTH: 20

```
<212> TYPE: DNA
<213> ORGANISM: Artificial Sequence
<220> FEATURE:
<223> OTHER INFORMATION: Synthetic Primer

<400> SEQUENCE: 16
ccttggaagg tgcagattga                                            20

<210> SEQ ID NO 17
<211> LENGTH: 22
<212> TYPE: DNA
<213> ORGANISM: Artificial Sequence
<220> FEATURE:
<223> OTHER INFORMATION: Synthetic Primer

<400> SEQUENCE: 17
tgacgacatc aagaaggtgg tg                                         22

<210> SEQ ID NO 18
<211> LENGTH: 21
<212> TYPE: DNA
<213> ORGANISM: Artificial Sequence
<220> FEATURE:
<223> OTHER INFORMATION: Synthetic Primer

<400> SEQUENCE: 18
gaaggtggag gagtgggtgt c                                          21
```